(12) United States Patent
Fraley et al.

(10) Patent No.: US 12,152,050 B2
(45) Date of Patent: *Nov. 26, 2024

(54) RNA-EDITING OLIGONUCLEOTIDES AND USES THEREOF

(71) Applicant: Korro Bio, Inc., Cambridge, MA (US)

(72) Inventors: Andrew W. Fraley, Arlington, MA (US); Steven Robinette, Fremont, NH (US); Nessan Bermingham, Boston, MA (US); Mallikarjuna Reddy Putta, Lexington, MA (US)

(73) Assignee: KORRO BIO, INC., Cambridge, MA (US)

( * ) Notice: Subject to any disclaimer, the term of this patent is extended or adjusted under 35 U.S.C. 154(b) by 36 days.

This patent is subject to a terminal disclaimer.

(21) Appl. No.: 17/932,359

(22) Filed: Sep. 15, 2022

(65) Prior Publication Data

US 2023/0146891 A1 May 11, 2023

Related U.S. Application Data

(62) Division of application No. 16/749,500, filed on Jan. 22, 2020, now Pat. No. 11,479,575.

(60) Provisional application No. 62/900,011, filed on Sep. 13, 2019, provisional application No. 62/822,527, filed on Mar. 22, 2019, provisional application No. 62/795,359, filed on Jan. 22, 2019.

(51) Int. Cl.
*C07H 19/16* (2006.01)
*C07H 19/06* (2006.01)
*C07H 21/00* (2006.01)
*C12N 15/11* (2006.01)

(52) U.S. Cl.
CPC ............ *C07H 19/16* (2013.01); *C07H 19/06* (2013.01); *C07H 21/00* (2013.01); *C12N 15/11* (2013.01)

(58) Field of Classification Search
None
See application file for complete search history.

(56) References Cited

U.S. PATENT DOCUMENTS

| | | |
|---|---|---|
| 5,399,676 A | 3/1995 | Froehler |
| 5,414,096 A | 5/1995 | Tino et al. |
| 6,673,611 B2 | 1/2004 | Thompson et al. |
| 6,878,805 B2 | 4/2005 | Manoharan et al. |
| 9,650,627 B1 | 5/2017 | Rosenthal et al. |
| 10,113,163 B2 | 10/2018 | Liu et al. |
| 10,925,973 B2 | 2/2021 | Kopecek et al. |
| 11,453,878 B2 | 9/2022 | Fraley et al. |
| 11,479,575 B2 | 10/2022 | Fraley et al. |
| 2005/0272075 A1 | 12/2005 | Jacobsen et al. |
| 2011/0065774 A1 | 3/2011 | Manoharan |
| 2015/0315594 A1 | 11/2015 | Prakash et al. |
| 2017/0166900 A1 | 6/2017 | Lindhorst et al. |
| 2017/0233731 A1 | 8/2017 | Tellers et al. |
| 2019/0070213 A1 | 3/2019 | Aznarez et al. |
| 2020/0385713 A1 | 12/2020 | Fraley et al. |
| 2021/0206868 A1 | 7/2021 | Subramanian et al. |
| 2023/0104978 A1 | 4/2023 | Fraley et al. |

FOREIGN PATENT DOCUMENTS

| | | |
|---|---|---|
| WO | 0220773 A2 | 3/2002 |
| WO | 2015172889 A1 | 11/2015 |
| WO | 2016094845 A2 | 6/2016 |
| WO | 2016097212 A1 | 6/2016 |
| WO | 2017010556 A1 | 1/2017 |
| WO | 2017050306 A1 | 3/2017 |
| WO | 2017146186 A1 | 8/2017 |
| WO | 2017220751 A1 | 12/2017 |
| WO | 2018041973 A1 | 3/2018 |
| WO | 2018134301 A1 | 7/2018 |
| WO | WO-2018/170333 A1 | 9/2018 |
| WO | WO-2018/191388 A1 | 10/2018 |
| WO | WO-2018/213708 A1 | 11/2018 |
| WO | 2019060746 A1 | 3/2019 |
| WO | 2019111957 A1 | 6/2019 |
| WO | 2019152416 A1 | 8/2019 |
| WO | 2019158475 A1 | 8/2019 |
| WO | 2019219581 A1 | 11/2019 |
| WO | 2020001793 A1 | 1/2020 |
| WO | 2020074001 A1 | 4/2020 |
| WO | 2020092448 A1 | 5/2020 |
| WO | 2020154342 A1 | 7/2020 |
| WO | 2020154343 A1 | 7/2020 |
| WO | 2020154344 A1 | 7/2020 |
| WO | 2020157008 A1 | 8/2020 |
| WO | 2020165077 A1 | 8/2020 |
| WO | 2021231830 A1 | 11/2021 |
| WO | 2021243023 A1 | 12/2021 |

OTHER PUBLICATIONS

Schneider et al., Journal of the American Chemical Society, 1990, vol. 112(1), 453-5. (Year: 1990).*
Zhou et al., Chemical Science, 2013, vol. 4(9), pp. 3693-3698. (Year: 2013).*
Schlegel et al., Journal of the American Chemical Society, 2017, vol. 139(25), pp. 8537-8546. (Year: 2017).*
Merkle et al., "Precise RNA editing by recruiting endogenous ADARs with antisense oligonucleotides." Nature Biotechnology 37: 133-138 (2019).
Agapkina et al., "Structure-Activity Relationship Studies of HIV-1 Integrase Oligonucleotide Inhibitors," ACS Med. Chem. Lett., 2011, 2:532-537.
Damha et al., "Hybrids of RNA and Arabinonucleic Acids (ANA and 2'F-ANA) are Substrates of Ribonuclease H," J Am Chem Soc, 1998, 120:12976-12977.
Davydova et al, "Aptamers Against Pathogenic Microorganisms," Crit Rev Microbiol., 2016, 42(6):847-865.

(Continued)

*Primary Examiner* — Traviss C McIntosh, III
(74) *Attorney, Agent, or Firm* — MARSHALL, GERSTEIN & BORUN LLP

(57) ABSTRACT

The present disclosure features useful compositions and methods to treat disorders for which deamination of an adenosine in an mRNA produces a therapeutic result, e.g., in a subject in need thereof.

17 Claims, No Drawings

Specification includes a Sequence Listing.

(56) References Cited

OTHER PUBLICATIONS

Egli et al., "Synthesis, Improved Antisense Activity and Structural Rationale for the Divergent RNA Affinities of 3'-Fluoro Hexitol Nucleic Acid (FHNA and Ara-FHNA) Modified Oligonucleotides," J. Am. Chem. Soc., 2011, 133:16642-16649.
Ferrari et al., "Characterization of Antisense Oligonucleotides Comprising 2'-Deoxy-2'-Fluoro-B-D-Arabinonucleic Acid (FANA): Specificity, Potency, and Duration of Activity," Ann. N.Y. Acad. Sci., 2006, 1082:91-102.
File History of U.S. Appl. No. 16/749,500, filed Jan. 22, 2020, Inventors: Andrew Fraley et al.
File History of U.S. Appl. No. 16/749,601, filed Jan. 22, 2020, Inventors: Andrew Fraley et al.
File History of U.S. Appl. No. 16/749,608, filed Jan. 22, 2020, Inventors: Andrew Fraley et al.
File History of U.S. Appl. No. 17/817,874, filed Aug. 5, 2022, Inventors: Andrew Fraley et al.
Gotfredsen et al., "Novel Oligodeoxynucleotide Analogues Containing a 2-O-Methylarabinonucleoside," Tetrahedron Letters, 1994, 35(37):6941-6944.
Herdewijn, "Nucleic Acids with a Six-Membered 'Carbohydrate' Mimic in the Backbone," Chemistry & Biodiversity, 2010, 7: 1-59.
International Search Report and Written Opinion for PCT/US2020/014510, dated Jun. 16, 2020, Applicant: Korro Bio, Inc.
International Search Report and Written Opinion for PCT/US2020/014511, dated May 1, 2020, Applicant: Korro Bio, Inc.
International Search Report and Written Opinion for PCT/US2020/014512, dated May 7, 2020, Applicant: Korro Bio, Inc.
Kashida et al., "Acyclic artificial nucleic acids with phosphodiester bonds exhibit unique functions," Polymer Journal, 2016, 48:781-786.
Kolb et al., "Hexitol Nucleic Acid-Containing Aptamers are Efficient Ligands of HIV-1 TAR RNA," Biochemistry, 2005, 44:2926-2933.
Le et al., "Antisense oligonucleotide modified with serinol nucleic acid (SNA) induces exon skipping in mdx myotubes," RSC Adv., 2017, 7:34049-34052.
Le et al., "Evaluation of anhydrohexitol nucleic acid, cyclohexenyl nucleic acid and D-altritol nucleic acid-modified 2'-O-methyl RNA mixmer antisense oligonucleotides for exon skipping in vitro," Chem Commun., 2016, 52:13467-13470.
Min et al., "Oligonucleotides Comprised of Alternating 2'-Deoxy-2'-fluro --D-arabinonucleosides and D-2'-deoxyribonucleosides (2'F-ANA/DNA 'Altimers') Induce Efficient RNA Cleavage mediated by RNase H," Bioorganic & Med Chem Letters, 2002, 12:2651-2654.
Murayama et al., "Highly Stable Duplex Formation by Artificial Nucleic Acids Acyclic Threoninol Nucleic Acid (aTNA) and Serinol Nucleic Acid (SNA) with Acyclic Scaffolds," Chem. Eur. J., 2013, 19:14151-14158.
Partial European Search Report in European Application No. 20744578.4 dated Jan. 16, 2023.
Partial European Search Report in European Application No. 20745581.7, dated Jan. 16, 2023.
Partial European Search Report in European Application No. 20745855.5, dated Jan. 17, 2023.
PubChem-CID-44607981, Feb. 11, 2010, 10 pages.
PubChem-CID-60143838, Aug. 27, 2012, p. 2.
Schneider et al., "Oligonucleotides Containing Flexible Nucleoside Analogues," J. Am. Chem. Soc., 1990, 112:453-455.
Taylor et al., "Catalysts from synthetic genetic polymers," Nature, 2015, 518:427-430.
Venkateswarlu et al., "Effects of C2'-Substitution on Arabinonucleic Acid Structure and Conformation," J Am Chem Soc, 1999, 121:5609-5610.
Vogel et al., "Improving site-directed RNA editing in vitro and in cell culture by chemical modification of the guideRNA," Agnew Chem Int Ed Engl, 2014, 53(24):6267-6271.
Wang et al., "Cyclohexene Nucleic Acids (CeNA): Serum Stable Oligonucleotides that Activate RNase H and Increase Duplex Stability with Complementary RNA," J. Am. Chem. Soc., 2000, 122:8595-8602.
Wang et al., "Selective Recognition of RNA Substrates by ADAR Deaminase Domains," Biochemistry, 2018, 57 (10):1640-1651.
Watts et al., "Differential stability of 2'F-ANA.RNA and ANA.RNA hybrid duplexes: roles of structure, pseudohydrogen bonding, hydration, ion uptake and flexibility," Nucleic Acids Res, 2010, 38(7): 2498-2511.
Zhou et al., "A "sugar-deficient" G-quadruplex: incorporation of aTNA in G4 structures," Chem Sci, 2013, 4: 3693-3698.
Zhou et al., Fine Tuning of Electrostatics around the Internucleotidic Phosphate through Incorporation of Modified 2', 4'-Carbocyclic-LNAs and -ENAs Leads to Significant Modulation of Antisense Properties, Journal of Organic Chemistry, 2008, 74(1):118-134.
Zhang et al., A Simple Glycol Nucleic Acid, J. Am. Chem. Soc., 127(12): 4174-4175, (Mar. 2005).
Bao et al., Antisense oligonucleotide modified with serinolnucleic acid (SNA) induces exon skipping in mdx myotubes, RSC Advances, 7(54): 34049-34052, (2017).
Cleaves et al., 227 Views of RNA: Is RNA Unique in Its Chemical Isomer Space?, Astrobiology, 15(7): 538-558, (Jul. 2015).
Doherty et al., Rational Design of RNA Editing Guide Strands: Cytidine Analogs at the Orphan Position, J. Am. Chem. Soc., 143(18): 6865-6876, (May 2021).
Beigelman et al., "Synthesis of 2-modified nucleotides and their incorporation into hammerhead ribozymes," Nucleic Acid Research 23(21):4434-4442 (1995).
International Search Report and Written Opinion in PCT/US2021/034521, dated Nov. 1, 2021, 12 pages.
International Search Report and Written Opinion issued in PCT/US2021/032394, mailed Sep. 21, 2021, 9 pages.
Nabel et al., "Nucleic acid determinants for selective deamination of DNA over RNA by activation-induced deaminase," PNAS, 110(35):14225-14230 (2013).
Robaldo et al., "Activity of Core-Modified 10-23 DNAzymes against HCV," ChemMedChem 9:2172-2177 (2014).
Tanna et al., "Stargardt disease: clinical features, molecular genetics, animal models and therapeutic options," British Journal of Ophthalmology Epub 101:25-30 (2017).

* cited by examiner

SEQUENCE LISTING

```
Sequence total quantity: 78
SEQ ID NO: 1                  moltype = RNA  length = 20
FEATURE                       Location/Qualifiers
misc_feature                  1..20
                              note = Synthetic Construct
source                        1..20
                              mol_type = other RNA
                              organism = synthetic construct
SEQUENCE: 1
ggtgaatagt ataacaatat                                                      20

SEQ ID NO: 2                  moltype = RNA  length = 20
FEATURE                       Location/Qualifiers
misc_feature                  1..20
                              note = Synthetic Construct
source                        1..20
                              mol_type = other RNA
                              organism = synthetic construct
SEQUENCE: 2
atgttgttat agtatccacc                                                      20

SEQ ID NO: 3                  moltype = RNA  length = 45
FEATURE                       Location/Qualifiers
misc_feature                  1..45
                              note = Synthetic Construct
source                        1..45
                              mol_type = other RNA
                              organism = synthetic construct
SEQUENCE: 3
ggtgaatagt ataacaatat gctaaatgtt gttatagtat ccacc                          45

SEQ ID NO: 4                  moltype = RNA  length = 20
FEATURE                       Location/Qualifiers
misc_feature                  1..20
                              note = Synthetic Construct
source                        1..20
                              mol_type = other RNA
                              organism = synthetic construct
SEQUENCE: 4
ggtgaagagg agaacaatat                                                      20

SEQ ID NO: 5                  moltype = RNA  length = 20
FEATURE                       Location/Qualifiers
misc_feature                  1..20
                              note = Synthetic Construct
source                        1..20
                              mol_type = other RNA
                              organism = synthetic construct
SEQUENCE: 5
atgttgttct cgtctccacc                                                      20

SEQ ID NO: 6                  moltype = RNA  length = 45
FEATURE                       Location/Qualifiers
misc_feature                  1..45
                              note = Synthetic Construct
source                        1..45
                              mol_type = other RNA
                              organism = synthetic construct
SEQUENCE: 6
ggtgaagagg agaacaatat gctaaatgtt gttctcgtct ccacc                          45

SEQ ID NO: 7                  moltype = RNA  length = 25
FEATURE                       Location/Qualifiers
misc_feature                  1..25
                              note = Synthetic Construct
source                        1..25
                              mol_type = other RNA
                              organism = synthetic construct
SEQUENCE: 7
ggtgtcgaga agaggagaac aatat                                                25

SEQ ID NO: 8                  moltype = RNA  length = 25
FEATURE                       Location/Qualifiers
misc_feature                  1..25
                              note = Synthetic Construct
source                        1..25
                              mol_type = other RNA
                              organism = synthetic construct
```

```
SEQUENCE: 8
atgttgttct cgtctcctcg acacc                                              25

SEQ ID NO: 9           moltype = RNA   length = 55
FEATURE                Location/Qualifiers
misc_feature           1..55
                       note = Synthetic Construct
source                 1..55
                       mol_type = other RNA
                       organism = synthetic construct
SEQUENCE: 9
ggtgtcgaga agaggagaac aatatgctaa atgttgttct cgtctcctcg acacc             55

SEQ ID NO: 10          moltype = RNA   length = 22
FEATURE                Location/Qualifiers
misc_feature           1..22
                       note = Synthetic Construct
source                 1..22
                       mol_type = other RNA
                       organism = synthetic construct
SEQUENCE: 10
gggtggaata gtataacaat at                                                 22

SEQ ID NO: 11          moltype = RNA   length = 22
FEATURE                Location/Qualifiers
misc_feature           1..22
                       note = Synthetic Construct
source                 1..22
                       mol_type = other RNA
                       organism = synthetic construct
SEQUENCE: 11
atgttgttat agtatcccac ct                                                 22

SEQ ID NO: 12          moltype = RNA   length = 48
FEATURE                Location/Qualifiers
misc_feature           1..48
                       note = Synthetic Construct
source                 1..48
                       mol_type = other RNA
                       organism = synthetic construct
SEQUENCE: 12
gggtggaata gtataacaat atgctaaatg ttgttatagt atcccacc                     48

SEQ ID NO: 13          moltype = RNA   length = 20
FEATURE                Location/Qualifiers
misc_feature           1..20
                       note = Synthetic Construct
source                 1..20
                       mol_type = other RNA
                       organism = synthetic construct
SEQUENCE: 13
gtggaatagt ataacaatat                                                    20

SEQ ID NO: 14          moltype = RNA   length = 20
FEATURE                Location/Qualifiers
misc_feature           1..20
                       note = Synthetic Construct
source                 1..20
                       mol_type = other RNA
                       organism = synthetic construct
SEQUENCE: 14
atgttgttat agtatcccac                                                    20

SEQ ID NO: 15          moltype = RNA   length = 45
FEATURE                Location/Qualifiers
misc_feature           1..45
                       note = Synthetic Construct
source                 1..45
                       mol_type = other RNA
                       organism = synthetic construct
SEQUENCE: 15
gtggaatagt ataacaatat gctaaatgtt gttatagtat cccac                        45

SEQ ID NO: 16          moltype = RNA   length = 25
FEATURE                Location/Qualifiers
misc_feature           1..25
                       note = Synthetic Construct
```

```
source                    1..25
                          mol_type = other RNA
                          organism = synthetic construct
SEQUENCE: 16
ggtgtcgaga atagtataac aatat                                      25

SEQ ID NO: 17             moltype = RNA  length = 25
FEATURE                   Location/Qualifiers
misc_feature              1..25
                          note = Synthetic Construct
source                    1..25
                          mol_type = other RNA
                          organism = synthetic construct
SEQUENCE: 17
atgttgttat agtatcctcg acacc                                      25

SEQ ID NO: 18             moltype = RNA  length = 55
FEATURE                   Location/Qualifiers
misc_feature              1..55
                          note = Synthetic Construct
source                    1..55
                          mol_type = other RNA
                          organism = synthetic construct
SEQUENCE: 18
ggtgtcgaga atagtataac aatatgctaa atgttgttat agtatcctcg acacc     55

SEQ ID NO: 19             moltype = RNA  length = 22
FEATURE                   Location/Qualifiers
misc_feature              1..22
                          note = Synthetic Construct
source                    1..22
                          mol_type = other RNA
                          organism = synthetic construct
SEQUENCE: 19
gggtggaata gtataacaat at                                         22

SEQ ID NO: 20             moltype = RNA  length = 22
FEATURE                   Location/Qualifiers
misc_feature              1..22
                          note = Synthetic Construct
source                    1..22
                          mol_type = other RNA
                          organism = synthetic construct
SEQUENCE: 20
atgttgttat agtatcccac ct                                         22

SEQ ID NO: 21             moltype = RNA  length = 49
FEATURE                   Location/Qualifiers
misc_feature              1..49
                          note = Synthetic Construct
source                    1..49
                          mol_type = other RNA
                          organism = synthetic construct
SEQUENCE: 21
gggtggaata gtataacaat atgctaaatg ttgttatagt atcccacct            49

SEQ ID NO: 22             moltype = RNA  length = 18
FEATURE                   Location/Qualifiers
misc_feature              1..18
                          note = Synthetic Construct
source                    1..18
                          mol_type = other RNA
                          organism = synthetic construct
SEQUENCE: 22
gggtggaata gtatacca                                              18

SEQ ID NO: 23             moltype = RNA  length = 18
FEATURE                   Location/Qualifiers
misc_feature              1..18
                          note = Synthetic Construct
source                    1..18
                          mol_type = other RNA
                          organism = synthetic construct
SEQUENCE: 23
tggtatagta tcccacct                                              18
```

```
SEQ ID NO: 24           moltype = RNA  length = 40
FEATURE                 Location/Qualifiers
misc_feature            1..40
                        note = Synthetic Construct
source                  1..40
                        mol_type = other RNA
                        organism = synthetic construct
SEQUENCE: 24
gggtggaata gtataccatt cgtggtatag tatcccacct                                40

SEQ ID NO: 25           moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 25
gtgggtggaa tagtatacca                                                     20

SEQ ID NO: 26           moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 26
tggtatagta tcccacctac                                                     20

SEQ ID NO: 27           moltype = RNA  length = 44
FEATURE                 Location/Qualifiers
misc_feature            1..44
                        note = Synthetic Construct
source                  1..44
                        mol_type = other RNA
                        organism = synthetic construct
SEQUENCE: 27
gtgggtggaa tagtatacca ttcgtggtat agtatcccac ctac                          44

SEQ ID NO: 28           moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 28
tgggtggaat agtatacca                                                      19

SEQ ID NO: 29           moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 29
tggtatagta tcccaccta                                                      19

SEQ ID NO: 30           moltype = RNA  length = 42
FEATURE                 Location/Qualifiers
misc_feature            1..42
                        note = Synthetic Construct
source                  1..42
                        mol_type = other RNA
                        organism = synthetic construct
SEQUENCE: 30
tgggtggaat agtataccat tcgtggtata gtatcccacc ta                            42

SEQ ID NO: 31           moltype = RNA  length = 17
FEATURE                 Location/Qualifiers
misc_feature            1..17
                        note = Synthetic Construct
source                  1..17
                        mol_type = other RNA
                        organism = synthetic construct
```

```
SEQUENCE: 31
ggtggaatag tatacca                                                      17

SEQ ID NO: 32           moltype = RNA  length = 17
FEATURE                 Location/Qualifiers
misc_feature            1..17
                        note = Synthetic Construct
source                  1..17
                        mol_type = other RNA
                        organism = synthetic construct
SEQUENCE: 32
tggtatagta tcccacc                                                      17

SEQ ID NO: 33           moltype = RNA  length = 38
FEATURE                 Location/Qualifiers
misc_feature            1..38
                        note = Synthetic Construct
source                  1..38
                        mol_type = other RNA
                        organism = synthetic construct
SEQUENCE: 33
ggtggaatag tataccattc gtggtatagt atcccacc                                38

SEQ ID NO: 34           moltype = RNA  length = 16
FEATURE                 Location/Qualifiers
misc_feature            1..16
                        note = Synthetic Construct
source                  1..16
                        mol_type = other RNA
                        organism = synthetic construct
SEQUENCE: 34
gtggaatagt atacca                                                       16

SEQ ID NO: 35           moltype = RNA  length = 16
FEATURE                 Location/Qualifiers
misc_feature            1..16
                        note = Synthetic Construct
source                  1..16
                        mol_type = other RNA
                        organism = synthetic construct
SEQUENCE: 35
tggtatagta tcccac                                                       16

SEQ ID NO: 36           moltype = RNA  length = 36
FEATURE                 Location/Qualifiers
misc_feature            1..36
                        note = Synthetic Construct
source                  1..36
                        mol_type = other RNA
                        organism = synthetic construct
SEQUENCE: 36
gtggaatagt ataccattcg tggtatagta tcccac                                 36

SEQ ID NO: 37           moltype = RNA  length = 45
FEATURE                 Location/Qualifiers
misc_feature            1..45
                        note = Synthetic Construct
source                  1..45
                        mol_type = other RNA
                        organism = synthetic construct
SEQUENCE: 37
ggtgaatagt ataacaatat gctaaatgtt gttatagtat ccacc                       45

SEQ ID NO: 38           moltype = RNA  length = 45
FEATURE                 Location/Qualifiers
misc_feature            1..45
                        note = Synthetic Construct
source                  1..45
                        mol_type = other RNA
                        organism = synthetic construct
SEQUENCE: 38
ggtgaagagg agaacaatat gctaaatgtt gttctcgtct ccacc                       45

SEQ ID NO: 39           moltype = RNA  length = 55
FEATURE                 Location/Qualifiers
misc_feature            1..55
                        note = Synthetic Construct
```

```
                        source          1..55
                                        mol_type = other RNA
                                        organism = synthetic construct
SEQUENCE: 39
ggtgtcgaga agaggagaac aatatgctaa atgttgttct cgtctcctcg acacc            55

SEQ ID NO: 40           moltype = RNA   length = 55
FEATURE                 Location/Qualifiers
misc_feature            1..55
                        note = Synthetic Construct
misc_feature            1..3
                        note = n is a 2'-O-methyl nucleotide
misc_feature            5..6
                        note = n is a 2'-O-methyl nucleotide
misc_feature            20
                        note = n is a 2'-O-methyl nucleotide
misc_feature            23
                        note = n is a 2'-O-methyl nucleotide
misc_feature            25
                        note = n is a 2'-O-methyl nucleotide
misc_feature            27..28
                        note = n is a 2'-O-methyl nucleotide
misc_feature            32
                        note = n is a 2'-O-methyl nucleotide
misc_feature            34..35
                        note = n is a 2'-O-methyl nucleotide
misc_feature            37..41
                        note = n is a 2'-O-methyl nucleotide
misc_feature            43..49
                        note = n is a 2'-O-methyl nucleotide
misc_feature            52
                        note = n is a 2'-O-methyl nucleotide
misc_feature            54..55
                        note = n is a 2'-O-methyl nucleotide
source                  1..55
                        mol_type = other RNA
                        organism = synthetic construct
SEQUENCE: 40
nnngnngaga agaggagaan aanangnnaa angnngnnnn ngnnnnnnng anann            55

SEQ ID NO: 41           moltype = RNA   length = 49
FEATURE                 Location/Qualifiers
misc_feature            1..49
                        note = Synthetic Construct
source                  1..49
                        mol_type = other RNA
                        organism = synthetic construct
SEQUENCE: 41
gggtggaata gtataacaat atgctaaatg ttgttatagt atcccacct                   49

SEQ ID NO: 42           moltype = RNA   length = 45
FEATURE                 Location/Qualifiers
misc_feature            1..45
                        note = Synthetic Construct
source                  1..45
                        mol_type = other RNA
                        organism = synthetic construct
SEQUENCE: 42
gtggaatagt ataacaatat gctaaatgtt gttatagtat cccac                       45

SEQ ID NO: 43           moltype = RNA   length = 55
FEATURE                 Location/Qualifiers
misc_feature            1..55
                        note = Synthetic Construct
source                  1..55
                        mol_type = other RNA
                        organism = synthetic construct
SEQUENCE: 43
ggtgtcgaga atagtataac aatatgctaa atgttgttat agtatcctcg acacc            55

SEQ ID NO: 44           moltype = RNA   length = 49
FEATURE                 Location/Qualifiers
misc_feature            1..49
                        note = Synthetic Construct
source                  1..49
                        mol_type = other RNA
                        organism = synthetic construct
SEQUENCE: 44
gggtggaata gtataacaat atgctaaatg ttgttatagt atcccacct                   49
```

```
SEQ ID NO: 45          moltype = RNA   length = 40
FEATURE                Location/Qualifiers
misc_feature           1..40
                       note = Synthetic Construct
source                 1..40
                       mol_type = other RNA
                       organism = synthetic construct
SEQUENCE: 45
gggtggaata gtataccatt cgtggtatag tatcccacct                              40

SEQ ID NO: 46          moltype = RNA   length = 44
FEATURE                Location/Qualifiers
misc_feature           1..44
                       note = Synthetic Construct
source                 1..44
                       mol_type = other RNA
                       organism = synthetic construct
SEQUENCE: 46
gtgggtggaa tagtatacca ttcgtggtat agtatcccac ctac                         44

SEQ ID NO: 47          moltype = RNA   length = 42
FEATURE                Location/Qualifiers
misc_feature           1..42
                       note = Synthetic Construct
source                 1..42
                       mol_type = other RNA
                       organism = synthetic construct
SEQUENCE: 47
tgggtggaat agtataccat tcgtggtata gtatcccacc ta                           42

SEQ ID NO: 48          moltype = RNA   length = 38
FEATURE                Location/Qualifiers
misc_feature           1..38
                       note = Synthetic Construct
source                 1..38
                       mol_type = other RNA
                       organism = synthetic construct
SEQUENCE: 48
ggtggaatag taccattc gtggtatagt atcccacc                                  38

SEQ ID NO: 49          moltype = RNA   length = 36
FEATURE                Location/Qualifiers
misc_feature           1..36
                       note = Synthetic Construct
source                 1..36
                       mol_type = other RNA
                       organism = synthetic construct
SEQUENCE: 49
gtggaatagt ataccattcg tggtatagta tcccac                                  36

SEQ ID NO: 50          moltype = DNA   length = 19
FEATURE                Location/Qualifiers
misc_feature           1..19
                       note = Synthetic Construct
source                 1..19
                       mol_type = other DNA
                       organism = synthetic construct
SEQUENCE: 50
acatgaggat cacccatgt                                                     19

SEQ ID NO: 51          moltype = RNA   length = 50
FEATURE                Location/Qualifiers
misc_feature           1..50
                       note = Synthetic Construct
modified_base          1
                       mod_base = OTHER
                       note = 2-O-methylcytidine
modified_base          2
                       mod_base = OTHER
                       note = 2-O-methyladenosine
modified_base          3
                       mod_base = OTHER
                       note = 2'-O-methyluridine
modified_base          4
                       mod_base = OTHER
                       note = 2-O-methyladenosine
```

```
modified_base          5
                       mod_base = OTHER
                       note = 2-O-methyladenosine
modified_base          46..47
                       mod_base = OTHER
                       note = 2'-O-methyluridine
modified_base          48..50
                       mod_base = OTHER
                       note = 2-O-methylcytidine
source                 1..50
                       mol_type = other RNA
                       organism = synthetic construct
SEQUENCE: 51
cataattctt gtgtctactg tacagaatac tgccgccagc tggatttccc           50

SEQ ID NO: 52          moltype = RNA  length = 50
FEATURE                Location/Qualifiers
misc_feature           1..50
                       note = Synthetic Construct
modified_base          1
                       mod_base = OTHER
                       note = 2'-O-methylcytidine
modified_base          2
                       mod_base = OTHER
                       note = 2'-O-methyladenosine
modified_base          3
                       mod_base = OTHER
                       note = 2'-O-methyluridine
modified_base          4..5
                       mod_base = OTHER
                       note = 2'-O-methyladenosine
modified_base          36
                       mod_base = OTHER
                       note = (S)-(-)-GNA-cytidine
modified_base          46..47
                       mod_base = OTHER
                       note = 2'-O-methyluridine
modified_base          48..50
                       mod_base = OTHER
                       note = 2'-O-methylcytidine
source                 1..50
                       mol_type = other RNA
                       organism = synthetic construct
SEQUENCE: 52
cataattctt gtgtctactg tacagaatac tgccgccagc tggatttccc           50

SEQ ID NO: 53          moltype = RNA  length = 50
FEATURE                Location/Qualifiers
misc_feature           1..50
                       note = Synthetic Construct
modified_base          1
                       mod_base = OTHER
                       note = 2'-O-methylcytidine
modified_base          2
                       mod_base = OTHER
                       note = 2'-O-methyladenosine
modified_base          3
                       mod_base = OTHER
                       note = 2'-O-methyluridine
modified_base          4..5
                       mod_base = OTHER
                       note = 2'-O-methyladenosine
modified_base          4..5
                       mod_base = OTHER
                       note = 2'-O-methyladenosine
modified_base          37
                       mod_base = OTHER
                       note = (S)-(-)-GNA-cytidine
modified_base          46..47
                       mod_base = OTHER
                       note = 2'-O-methyluridine
modified_base          48..50
                       mod_base = OTHER
                       note = 2'-O-methylcytidine
source                 1..50
                       mol_type = other RNA
                       organism = synthetic construct
```

```
SEQUENCE: 53
cataattctt gtgtctactg tacagaatac tgccgccagc tggatttccc                50

SEQ ID NO: 54           moltype = RNA   length = 50
FEATURE                 Location/Qualifiers
misc_feature            1..50
                        note = Synthetic Construct
modified_base           1
                        mod_base = OTHER
                        note = 2'-O-methylcytidine
modified_base           2
                        mod_base = OTHER
                        note = 2'-O-methyladenosine
modified_base           3
                        mod_base = OTHER
                        note = 2'-O-methyluridine
modified_base           4..5
                        mod_base = OTHER
                        note = 2'-O-methyladenosine
modified_base           36..37
                        mod_base = OTHER
                        note = (S)-(-)-GNA-cytidine
modified_base           46..47
                        mod_base = OTHER
                        note = 2'-O-methyluridine
modified_base           48..50
                        mod_base = OTHER
                        note = 2'-O-methylcytidine
source                  1..50
                        mol_type = other RNA
                        organism = synthetic construct
SEQUENCE: 54
cataattctt gtgtctactg tacagaatac tgccgccagc tggatttccc                50

SEQ ID NO: 55           moltype = RNA   length = 50
FEATURE                 Location/Qualifiers
misc_feature            1..50
                        note = Synthetic Construct
modified_base           1
                        mod_base = OTHER
                        note = 2'-O-methylcytidine
modified_base           2
                        mod_base = OTHER
                        note = 2'-O-methyladenosine
modified_base           3
                        mod_base = OTHER
                        note = 2'-O-methyluridine
modified_base           4..5
                        mod_base = OTHER
                        note = 2'-O-methyladenosine
modified_base           36
                        mod_base = OTHER
                        note = (R)-(+)-GNA-cytidine
modified_base           46..47
                        mod_base = OTHER
                        note = 2'-O-methyluridine
modified_base           48..50
                        mod_base = OTHER
                        note = 2'-O-methylcytidine
source                  1..50
                        mol_type = other RNA
                        organism = synthetic construct
SEQUENCE: 55
cataattctt gtgtctactg tacagaatac tgccgccagc tggatttccc                50

SEQ ID NO: 56           moltype = RNA   length = 50
FEATURE                 Location/Qualifiers
misc_feature            1..50
                        note = Synthetic Construct
modified_base           1
                        mod_base = OTHER
                        note = 2'-O-methylcytidine
modified_base           2
                        mod_base = OTHER
                        note = 2'-O-methyladenosine
modified_base           3
                        mod_base = OTHER
                        note = 2'-O-methyluridine
```

```
modified_base            4..5
                         mod_base = OTHER
                         note = 2'-O-methyladenosine
modified_base            37
                         mod_base = OTHER
                         note = (R)-(+)-GNA-cytidine
modified_base            46..47
                         mod_base = OTHER
                         note = 2'-O-methyluridine
modified_base            48..50
                         mod_base = OTHER
                         note = 2'-O-methylcytidine
source                   1..50
                         mol_type = other RNA
                         organism = synthetic construct
SEQUENCE: 56
cataattctt gtgtctactg tacagaatac tgccgccagc tggatttccc            50

SEQ ID NO: 57            moltype = RNA  length = 50
FEATURE                  Location/Qualifiers
misc_feature             1..50
                         note = Synthetic Construct
modified_base            1
                         mod_base = OTHER
                         note = 2'-O-methylcytidine
modified_base            2
                         mod_base = OTHER
                         note = 2'-O-methyladenosine
modified_base            3
                         mod_base = OTHER
                         note = 2'-O-methyluridine
modified_base            4..5
                         mod_base = OTHER
                         note = 2'-O-methyladenosine
modified_base            36
                         mod_base = OTHER
                         note = SNA-cytidine
modified_base            46..47
                         mod_base = OTHER
                         note = 2'-O-methyluridine
modified_base            48..50
                         mod_base = OTHER
                         note = 2'-O-methylcytidine
source                   1..50
                         mol_type = other RNA
                         organism = synthetic construct
SEQUENCE: 57
cataattctt gtgtctactg tacagaatac tgccgccagc tggatttccc            50

SEQ ID NO: 58            moltype = RNA  length = 50
FEATURE                  Location/Qualifiers
misc_feature             1..50
                         note = Synthetic Construct
modified_base            1
                         mod_base = OTHER
                         note = 2'-O-methylcytidine
modified_base            2
                         mod_base = OTHER
                         note = 2'-O-methyladenosine
modified_base            3
                         mod_base = OTHER
                         note = 2'-O-methyluridine
modified_base            4..5
                         mod_base = OTHER
                         note = 2'-O-methyladenosine
modified_base            4..5
                         mod_base = OTHER
                         note = 2'-O-methyladenosine
modified_base            37
                         mod_base = OTHER
                         note = SNA-cytidine
modified_base            46..47
                         mod_base = OTHER
                         note = 2'-O-methyluridine
modified_base            48..50
                         mod_base = OTHER
                         note = 2'-O-methylcytidine
```

```
source                      1..50
                            mol_type = other RNA
                            organism = synthetic construct
SEQUENCE: 58
cataattctt gtgtctactg tacagaatac tgccgccagc tggatttccc            50

SEQ ID NO: 59               moltype = RNA  length = 50
FEATURE                     Location/Qualifiers
misc_feature                1..50
                            note = Synthetic Construct
modified_base               1
                            mod_base = OTHER
                            note = 2'-O-methylcytidine
modified_base               2
                            mod_base = OTHER
                            note = 2'-O-methyladenosine
modified_base               3
                            mod_base = OTHER
                            note = 2'-O-methyluridine
modified_base               4..5
                            mod_base = OTHER
                            note = 2'-O-methyladenosine
modified_base               36
                            mod_base = OTHER
                            note = FNA-cytidine
modified_base               46..47
                            mod_base = OTHER
                            note = 2'-O-methyluridine
modified_base               48..50
                            mod_base = OTHER
                            note = 2'-O-methylcytidine
source                      1..50
                            mol_type = other RNA
                            organism = synthetic construct
SEQUENCE: 59
cataattctt gtgtctactg tacagaatac tgccgccagc tggatttccc            50

SEQ ID NO: 60               moltype = RNA  length = 50
FEATURE                     Location/Qualifiers
misc_feature                1..50
                            note = Synthetic Construct
modified_base               1
                            mod_base = OTHER
                            note = 2'-O-methylcytidine
modified_base               2
                            mod_base = OTHER
                            note = 2'-O-methyladenosine
modified_base               3
                            mod_base = OTHER
                            note = 2'-O-methyluridine
modified_base               4..5
                            mod_base = OTHER
                            note = 2'-O-methyladenosine
modified_base               37
                            mod_base = OTHER
                            note = FNA-cytidine
modified_base               46..47
                            mod_base = OTHER
                            note = 2'-O-methyluridine
modified_base               48..50
                            mod_base = OTHER
                            note = 2'-O-methylcytidine
source                      1..50
                            mol_type = other RNA
                            organism = synthetic construct
SEQUENCE: 60
cataattctt gtgtctactg tacagaatac tgccgccagc tggatttccc            50

SEQ ID NO: 61               moltype = RNA  length = 50
FEATURE                     Location/Qualifiers
misc_feature                1..50
                            note = Synthetic Construct
modified_base               1
                            mod_base = OTHER
                            note = 2'-O-methylcytidine
modified_base               2
                            mod_base = OTHER
                            note = 2'-O-methyladenosine
```

```
modified_base          3
                       mod_base = OTHER
                       note = 2'-O-methyluridine
modified_base          4..5
                       mod_base = OTHER
                       note = 2'-O-methyladenosine
modified_base          9..10
                       mod_base = OTHER
                       note = 2'-O-methyluridine
modified_base          14
                       mod_base = OTHER
                       note = 2'-O-methyluridine
modified_base          15
                       mod_base = OTHER
                       note = 2'-O-methylcytidine
modified_base          19
                       mod_base = OTHER
                       note = 2'-O-methyluridine
modified_base          20
                       mod_base = OTHER
                       note = 2'-O-methylguanosine
modified_base          24
                       mod_base = OTHER
                       note = 2'-O-methyladenosine
modified_base          25
                       mod_base = OTHER
                       note = 2'-O-methylguanosine
modified_base          29
                       mod_base = OTHER
                       note = 2'-O-methyladenosine
modified_base          30
                       mod_base = OTHER
                       note = 2'-O-methylcytidine
modified_base          34
                       mod_base = OTHER
                       note = 2'-O-methylcytidine
modified_base          35
                       mod_base = OTHER
                       note = 2'-O-methylguanosine
modified_base          39
                       mod_base = OTHER
                       note = 2'-O-methylguanosine
modified_base          40
                       mod_base = OTHER
                       note = 2'-O-methylcytidine
modified_base          43
                       mod_base = OTHER
                       note = 2'-O-methylguanosine
modified_base          44
                       mod_base = OTHER
                       note = 2'-O-methyladenosine
modified_base          46..47
                       mod_base = OTHER
                       note = 2'-O-methyluridine
modified_base          48..50
                       mod_base = OTHER
                       note = 2'-O-methylcytidine
source                 1..50
                       mol_type = other RNA
                       organism = synthetic construct
SEQUENCE: 61
cataattctt gtgtctactg tacagaatac tgccgccagc tggatttccc           50

SEQ ID NO: 62          moltype = RNA   length = 50
FEATURE                Location/Qualifiers
misc_feature           1..50
                       note = Synthetic Construct
modified_base          1
                       mod_base = OTHER
                       note = 2'-O-methylcytidine
modified_base          2
                       mod_base = OTHER
                       note = 2'-O-methyladenosine
modified_base          3
                       mod_base = OTHER
                       note = 2'-O-methyluridine
modified_base          4..5
                       mod_base = OTHER
                       note = 2'-O-methyladenosine
```

```
modified_base          4..5
                       mod_base = OTHER
                       note = 2'-O-methyladenosine
modified_base          9..10
                       mod_base = OTHER
                       note = 2'-O-methyluridine
modified_base          14
                       mod_base = OTHER
                       note = 2'-O-methyluridine
modified_base          15
                       mod_base = OTHER
                       note = 2'-O-methylcytidine
modified_base          19
                       mod_base = OTHER
                       note = 2'-O-methyluridine
modified_base          20
                       mod_base = OTHER
                       note = 2'-O-methylguanosine
modified_base          24
                       mod_base = OTHER
                       note = 2'-O-methyladenosine
modified_base          25
                       mod_base = OTHER
                       note = 2'-O-methylguanosine
modified_base          29
                       mod_base = OTHER
                       note = 2'-O-methyladenosine
modified_base          30
                       mod_base = OTHER
                       note = 2'-O-methylcytidine
modified_base          34
                       mod_base = OTHER
                       note = 2'-O-methylcytidine
modified_base          35
                       mod_base = OTHER
                       note = 2'-O-methylguanosine
modified_base          36
                       mod_base = OTHER
                       note = (S)-(-)-GNA-cytidine
modified_base          39
                       mod_base = OTHER
                       note = 2'-O-methylguanosine
modified_base          40
                       mod_base = OTHER
                       note = 2'-O-methylcytidine
modified_base          43
                       mod_base = OTHER
                       note = 2'-O-methylguanosine
modified_base          44
                       mod_base = OTHER
                       note = 2'-O-methyladenosine
modified_base          46..47
                       mod_base = OTHER
                       note = 2'-O-methyluridine
modified_base          48..50
                       mod_base = OTHER
                       note = 2'-O-methylcytidine
source                 1..50
                       mol_type = other RNA
                       organism = synthetic construct
SEQUENCE: 62
cataattctt gtgtctactg tacagaatac tgccgccagc tggatttccc            50

SEQ ID NO: 63         moltype = RNA   length = 50
FEATURE               Location/Qualifiers
misc_feature          1..50
                      note = Synthetic Construct
modified_base         1
                      mod_base = OTHER
                      note = 2'-O-methylcytidine
modified_base         2
                      mod_base = OTHER
                      note = 2'-O-methyladenosine
modified_base         3
                      mod_base = OTHER
                      note = 2'-O-methyluridine
modified_base         4..5
                      mod_base = OTHER
                      note = 2'-O-methyladenosine
```

| | | |
|---|---|---|
| modified_base | 9..10 | |
| | mod_base = OTHER | |
| | note = 2'-O-methyluridine | |
| modified_base | 14 | |
| | mod_base = OTHER | |
| | note = 2'-O-methyluridine | |
| modified_base | 15 | |
| | mod_base = OTHER | |
| | note = 2'-O-methylcytidine | |
| modified_base | 19 | |
| | mod_base = OTHER | |
| | note = 2'-O-methyluridine | |
| modified_base | 20 | |
| | mod_base = OTHER | |
| | note = 2'-O-methylguanosine | |
| modified_base | 24 | |
| | mod_base = OTHER | |
| | note = 2'-O-methyladenosine | |
| modified_base | 25 | |
| | mod_base = OTHER | |
| | note = 2'-O-methylguanosine | |
| modified_base | 25 | |
| | mod_base = OTHER | |
| | note = 2'-O-methylguanosine | |
| modified_base | 29 | |
| | mod_base = OTHER | |
| | note = 2'-O-methyladenosine | |
| modified_base | 30 | |
| | mod_base = OTHER | |
| | note = 2'-O-methylcytidine | |
| modified_base | 34 | |
| | mod_base = OTHER | |
| | note = 2'-O-methylcytidine | |
| modified_base | 35 | |
| | mod_base = OTHER | |
| | note = 2'-O-methylguanosine | |
| modified_base | 37 | |
| | mod_base = OTHER | |
| | note = (S)-(-)-GNA-cytidine | |
| modified_base | 39 | |
| | mod_base = OTHER | |
| | note = 2'-O-methylguanosine | |
| modified_base | 40 | |
| | mod_base = OTHER | |
| | note = 2'-O-methylcytidine | |
| modified_base | 43 | |
| | mod_base = OTHER | |
| | note = 2'-O-methylguanosine | |
| modified_base | 44 | |
| | mod_base = OTHER | |
| | note = 2'-O-methyladenosine | |
| modified_base | 46..47 | |
| | mod_base = OTHER | |
| | note = 2'-O-methyluridine | |
| modified_base | 48..50 | |
| | mod_base = OTHER | |
| | note = 2'-O-methylcytidine | |
| source | 1..50 | |
| | mol_type = other RNA | |
| | organism = synthetic construct | |
| SEQUENCE: 63 | | |
| cataattctt gtgtctactg tacagaatac tgccgccagc tggatttccc | | 50 |
| | | |
| SEQ ID NO: 64 | moltype = RNA   length = 50 | |
| FEATURE | Location/Qualifiers | |
| misc_feature | 1..50 | |
| | note = Synthetic Construct | |
| modified_base | 1 | |
| | mod_base = OTHER | |
| | note = 2'-O-methylcytidine | |
| modified_base | 2 | |
| | mod_base = OTHER | |
| | note = 2'-O-methyladenosine | |
| modified_base | 3 | |
| | mod_base = OTHER | |
| | note = 2'-O-methyluridine | |
| modified_base | 4..5 | |
| | mod_base = OTHER | |
| | note = 2'-O-methyladenosine | |

```
modified_base        9..10
                     mod_base = OTHER
                     note = 2'-O-methyluridine
modified_base        14
                     mod_base = OTHER
                     note = 2'-O-methyluridine
modified_base        15
                     mod_base = OTHER
                     note = 2'-O-methylcytidine
modified_base        19
                     mod_base = OTHER
                     note = 2'-O-methyluridine
modified_base        20
                     mod_base = OTHER
                     note = 2'-O-methylguanosine
modified_base        24
                     mod_base = OTHER
                     note = 2'-O-methyladenosine
modified_base        25
                     mod_base = OTHER
                     note = 2'-O-methylguanosine
modified_base        29
                     mod_base = OTHER
                     note = 2'-O-methyladenosine
modified_base        30
                     mod_base = OTHER
                     note = 2'-O-methylcytidine
modified_base        34
                     mod_base = OTHER
                     note = 2'-O-methylcytidine
modified_base        35
                     mod_base = OTHER
                     note = 2'-O-methylguanosine
modified_base        36..37
                     mod_base = OTHER
                     note = (S)-(-)-GNA-cytidine
modified_base        39
                     mod_base = OTHER
                     note = 2'-O-methylguanosine
modified_base        40
                     mod_base = OTHER
                     note = 2'-O-methylcytidine
modified_base        43
                     mod_base = OTHER
                     note = 2'-O-methylguanosine
modified_base        44
                     mod_base = OTHER
                     note = 2'-O-methyladenosine
modified_base        46..47
                     mod_base = OTHER
                     note = 2'-O-methyluridine
modified_base        48..50
                     mod_base = OTHER
                     note = 2'-O-methylcytidine
source               1..50
                     mol_type = other RNA
                     organism = synthetic construct
SEQUENCE: 64
cataattctt gtgtctactg tacagaatac tgccgccagc tggatttccc                50

SEQ ID NO: 65        moltype = RNA   length = 50
FEATURE              Location/Qualifiers
misc_feature         1..50
                     note = Synthetic Construct
modified_base        1
                     mod_base = OTHER
                     note = 2'-O-methylcytidine
modified_base        2
                     mod_base = OTHER
                     note = 2'-O-methyladenosine
modified_base        3
                     mod_base = OTHER
                     note = 2'-O-methyluridine
modified_base        4..5
                     mod_base = OTHER
                     note = 2'-O-methyladenosine
modified_base        9..10
                     mod_base = OTHER
                     note = 2'-O-methyluridine
```

```
modified_base      14
                   mod_base = OTHER
                   note = 2'-O-methyluridine
modified_base      15
                   mod_base = OTHER
                   note = 2'-O-methylcytidine
modified_base      19
                   mod_base = OTHER
                   note = 2'-O-methyluridine
modified_base      20
                   mod_base = OTHER
                   note = 2'-O-methylguanosine
modified_base      24
                   mod_base = OTHER
                   note = 2'-O-methyladenosine
modified_base      25
                   mod_base = OTHER
                   note = 2'-O-methylguanosine
modified_base      29
                   mod_base = OTHER
                   note = 2'-O-methyladenosine
modified_base      30
                   mod_base = OTHER
                   note = 2'-O-methylcytidine
modified_base      34
                   mod_base = OTHER
                   note = 2'-O-methylcytidine
modified_base      35
                   mod_base = OTHER
                   note = 2'-O-methylguanosine
modified_base      36
                   mod_base = OTHER
                   note = (R)-(+)-GNA-cytidine
modified_base      39
                   mod_base = OTHER
                   note = 2'-O-methylguanosine
modified_base      40
                   mod_base = OTHER
                   note = 2'-O-methylcytidine
modified_base      43
                   mod_base = OTHER
                   note = 2'-O-methylguanosine
modified_base      44
                   mod_base = OTHER
                   note = 2'-O-methyladenosine
modified_base      46..47
                   mod_base = OTHER
                   note = 2'-O-methyluridine
modified_base      48..50
                   mod_base = OTHER
                   note = 2'-O-methylcytidine
source             1..50
                   mol_type = other RNA
                   organism = synthetic construct
SEQUENCE: 65
cataattctt gtgtctactg tacagaatac tgccgccagc tggatttccc                50

SEQ ID NO: 66      moltype = RNA   length = 50
FEATURE            Location/Qualifiers
misc_feature       1..50
                   note = Synthetic Construct
modified_base      1
                   mod_base = OTHER
                   note = 2'-O-methylcytidine
modified_base      2
                   mod_base = OTHER
                   note = 2'-O-methyladenosine
modified_base      3
                   mod_base = OTHER
                   note = 2'-O-methyluridine
modified_base      4..5
                   mod_base = OTHER
                   note = 2'-O-methyladenosine
modified_base      9..10
                   mod_base = OTHER
                   note = 2'-O-methyluridine
modified_base      14
                   mod_base = OTHER
                   note = 2'-O-methyluridine
```

```
modified_base          15
                       mod_base = OTHER
                       note = 2'-O-methylcytidine
modified_base          19
                       mod_base = OTHER
                       note = 2'-O-methyluridine
modified_base          20
                       mod_base = OTHER
                       note = 2'-O-methylguanosine
modified_base          24
                       mod_base = OTHER
                       note = 2'-O-methyladenosine
modified_base          25
                       mod_base = OTHER
                       note = 2'-O-methylguanosine
modified_base          29
                       mod_base = OTHER
                       note = 2'-O-methyladenosine
modified_base          30
                       mod_base = OTHER
                       note = 2'-O-methylcytidine
modified_base          34
                       mod_base = OTHER
                       note = 2'-O-methylcytidine
modified_base          35
                       mod_base = OTHER
                       note = 2'-O-methylguanosine
modified_base          37
                       mod_base = OTHER
                       note = (R)-(+)-GNA-cytidine
modified_base          39
                       mod_base = OTHER
                       note = 2'-O-methylguanosine
modified_base          40
                       mod_base = OTHER
                       note = 2'-O-methylcytidine
modified_base          43
                       mod_base = OTHER
                       note = 2'-O-methylguanosine
modified_base          44
                       mod_base = OTHER
                       note = 2'-O-methyladenosine
modified_base          46..47
                       mod_base = OTHER
                       note = 2'-O-methyluridine
modified_base          48..50
                       mod_base = OTHER
                       note = 2'-O-methylcytidine
source                 1..50
                       mol_type = other RNA
                       organism = synthetic construct
SEQUENCE: 66
cataattctt gtgtctactg tacagaatac tgccgccagc tggatttccc          50

SEQ ID NO: 67          moltype = RNA   length = 50
FEATURE                Location/Qualifiers
misc_feature           1..50
                       note = Synthetic Construct
modified_base          1
                       mod_base = OTHER
                       note = 2'-O-methylcytidine
modified_base          2
                       mod_base = OTHER
                       note = 2'-O-methyladenosine
modified_base          3
                       mod_base = OTHER
                       note = 2'-O-methyluridine
modified_base          4..5
                       mod_base = OTHER
                       note = 2'-O-methyladenosine
modified_base          9..10
                       mod_base = OTHER
                       note = 2'-O-methyluridine
modified_base          14
                       mod_base = OTHER
                       note = 2'-O-methyluridine
modified_base          15
                       mod_base = OTHER
                       note = 2'-O-methylcytidine
```

| | | |
|---|---|---|
| modified_base | 19 | |
| | mod_base = OTHER | |
| | note = 2'-O-methyluridine | |
| modified_base | 20 | |
| | mod_base = OTHER | |
| | note = 2'-O-methylguanosine | |
| modified_base | 24 | |
| | mod_base = OTHER | |
| | note = 2'-O-methyladenosine | |
| modified_base | 25 | |
| | mod_base = OTHER | |
| | note = 2'-O-methylguanosine | |
| modified_base | 29 | |
| | mod_base = OTHER | |
| | note = 2'-O-methyladenosine | |
| modified_base | 30 | |
| | mod_base = OTHER | |
| | note = 2'-O-methylcytidine | |
| modified_base | 34 | |
| | mod_base = OTHER | |
| | note = 2'-O-methylcytidine | |
| modified_base | 35 | |
| | mod_base = OTHER | |
| | note = 2'-O-methylguanosine | |
| modified_base | 36 | |
| | mod_base = OTHER | |
| | note = SNA-cytidine | |
| modified_base | 39 | |
| | mod_base = OTHER | |
| | note = 2'-O-methylguanosine | |
| modified_base | 40 | |
| | mod_base = OTHER | |
| | note = 2'-O-methylcytidine | |
| modified_base | 43 | |
| | mod_base = OTHER | |
| | note = 2'-O-methylguanosine | |
| modified_base | 44 | |
| | mod_base = OTHER | |
| | note = 2'-O-methyladenosine | |
| modified_base | 46..47 | |
| | mod_base = OTHER | |
| | note = 2'-O-methyluridine | |
| modified_base | 48..50 | |
| | mod_base = OTHER | |
| | note = 2'-O-methylcytidine | |
| source | 1..50 | |
| | mol_type = other RNA | |
| | organism = synthetic construct | |
| SEQUENCE: 67 | | |
| cataattctt gtgtctactg tacagaatac tgccgccagc tggatttccc | | 50 |
| | | |
| SEQ ID NO: 68 | moltype = RNA  length = 50 | |
| FEATURE | Location/Qualifiers | |
| misc_feature | 1..50 | |
| | note = Synthetic Construct | |
| modified_base | 1 | |
| | mod_base = OTHER | |
| | note = 2'-O-methylcytidine | |
| modified_base | 2 | |
| | mod_base = OTHER | |
| | note = 2'-O-methyladenosine | |
| modified_base | 3 | |
| | mod_base = OTHER | |
| | note = 2'-O-methyluridine | |
| modified_base | 4..5 | |
| | mod_base = OTHER | |
| | note = 2'-O-methyladenosine | |
| modified_base | 9..10 | |
| | mod_base = OTHER | |
| | note = 2'-O-methyluridine | |
| modified_base | 14 | |
| | mod_base = OTHER | |
| | note = 2'-O-methyluridine | |
| modified_base | 15 | |
| | mod_base = OTHER | |
| | note = 2'-O-methylcytidine | |
| modified_base | 19 | |
| | mod_base = OTHER | |
| | note = 2'-O-methyluridine | |

```
modified_base      20
                   mod_base = OTHER
                   note = 2'-O-methylguanosine
modified_base      24
                   mod_base = OTHER
                   note = 2'-O-methyladenosine
modified_base      25
                   mod_base = OTHER
                   note = 2'-O-methylguanosine
modified_base      29
                   mod_base = OTHER
                   note = 2'-O-methyladenosine
modified_base      30
                   mod_base = OTHER
                   note = 2'-O-methylcytidine
modified_base      34
                   mod_base = OTHER
                   note = 2'-O-methylcytidine
modified_base      35
                   mod_base = OTHER
                   note = 2'-O-methylguanosine
modified_base      37
                   mod_base = OTHER
                   note = SNA-cytidine
modified_base      39
                   mod_base = OTHER
                   note = 2'-O-methylguanosine
modified_base      40
                   mod_base = OTHER
                   note = 2'-O-methylcytidine
modified_base      43
                   mod_base = OTHER
                   note = 2'-O-methylguanosine
modified_base      44
                   mod_base = OTHER
                   note = 2'-O-methyladenosine
modified_base      46..47
                   mod_base = OTHER
                   note = 2'-O-methyluridine
modified_base      48..50
                   mod_base = OTHER
                   note = 2'-O-methylcytidine
source             1..50
                   mol_type = other RNA
                   organism = synthetic construct
SEQUENCE: 68
cataattctt gtgtctactg tacagaatac tgccgccagc tggatttccc              50

SEQ ID NO: 69      moltype = RNA   length = 50
FEATURE            Location/Qualifiers
misc_feature       1..50
                   note = Synthetic Construct
modified_base      1
                   mod_base = OTHER
                   note = 2'-O-methylcytidine
modified_base      2
                   mod_base = OTHER
                   note = 2'-O-methyladenosine
modified_base      3
                   mod_base = OTHER
                   note = 2'-O-methyluridine
modified_base      4..5
                   mod_base = OTHER
                   note = 2'-O-methyladenosine
modified_base      9..10
                   mod_base = OTHER
                   note = 2'-O-methyluridine
modified_base      14
                   mod_base = OTHER
                   note = 2'-O-methyluridine
modified_base      15
                   mod_base = OTHER
                   note = 2'-O-methylcytidine
modified_base      19
                   mod_base = OTHER
                   note = 2'-O-methyluridine
modified_base      20
                   mod_base = OTHER
                   note = 2'-O-methylguanosine
```

```
modified_base      24
                   mod_base = OTHER
                   note = 2'-O-methyladenosine
modified_base      25
                   mod_base = OTHER
                   note = 2'-O-methylguanosine
modified_base      29
                   mod_base = OTHER
                   note = 2'-O-methyladenosine
modified_base      30
                   mod_base = OTHER
                   note = 2'-O-methylcytidine
modified_base      34
                   mod_base = OTHER
                   note = 2'-O-methylcytidine
modified_base      35
                   mod_base = OTHER
                   note = 2'-O-methylguanosine
modified_base      36
                   mod_base = OTHER
                   note = FNA-cytidine
modified_base      39
                   mod_base = OTHER
                   note = 2'-O-methylguanosine
modified_base      40
                   mod_base = OTHER
                   note = 2'-O-methylcytidine
modified_base      43
                   mod_base = OTHER
                   note = 2'-O-methylguanosine
modified_base      44
                   mod_base = OTHER
                   note = 2'-O-methyladenosine
modified_base      46..47
                   mod_base = OTHER
                   note = 2'-O-methyluridine
modified_base      48..50
                   mod_base = OTHER
                   note = 2'-O-methylcytidine
source             1..50
                   mol_type = other RNA
                   organism = synthetic construct
SEQUENCE: 69
cataattctt gtgtctactg tacagaatac tgccgccagc tggatttccc                 50

SEQ ID NO: 70      moltype = RNA   length = 50
FEATURE            Location/Qualifiers
misc_feature       1..50
                   note = Synthetic Construct
modified_base      1
                   mod_base = OTHER
                   note = 2'-O-methylcytidine
modified_base      2
                   mod_base = OTHER
                   note = 2'-O-methyladenosine
modified_base      3
                   mod_base = OTHER
                   note = 2'-O-methyluridine
modified_base      4..5
                   mod_base = OTHER
                   note = 2'-O-methyladenosine
modified_base      9..10
                   mod_base = OTHER
                   note = 2'-O-methyluridine
modified_base      14
                   mod_base = OTHER
                   note = 2'-O-methyluridine
modified_base      15
                   mod_base = OTHER
                   note = 2'-O-methylcytidine
modified_base      19
                   mod_base = OTHER
                   note = 2'-O-methyluridine
modified_base      20
                   mod_base = OTHER
                   note = 2'-O-methylguanosine
modified_base      24
                   mod_base = OTHER
                   note = 2'-O-methyladenosine
```

```
modified_base            25
                         mod_base = OTHER
                         note = 2'-O-methylguanosine
modified_base            29
                         mod_base = OTHER
                         note = 2'-O-methyladenosine
modified_base            30
                         mod_base = OTHER
                         note = 2'-O-methylcytidine
modified_base            34
                         mod_base = OTHER
                         note = 2'-O-methylcytidine
modified_base            35
                         mod_base = OTHER
                         note = 2'-O-methylguanosine
modified_base            37
                         mod_base = OTHER
                         note = FNA-cytidine
modified_base            39
                         mod_base = OTHER
                         note = 2'-O-methylguanosine
modified_base            40
                         mod_base = OTHER
                         note = 2'-O-methylcytidine
modified_base            43
                         mod_base = OTHER
                         note = 2'-O-methylguanosine
modified_base            44
                         mod_base = OTHER
                         note = 2'-O-methyladenosine
modified_base            46..47
                         mod_base = OTHER
                         note = 2'-O-methyluridine
modified_base            48..50
                         mod_base = OTHER
                         note = 2'-O-methylcytidine
source                   1..50
                         mol_type = other RNA
                         organism = synthetic construct
SEQUENCE: 70
cataattctt gtgtctactg tacagaatac tgccgccagc tggatttccc                50

SEQ ID NO: 71            moltype = AA  length = 16
FEATURE                  Location/Qualifiers
source                   1..16
                         mol_type = protein
                         organism = Homo sapiens
SEQUENCE: 71
AAVALLPAVL LALLAP                                                     16

SEQ ID NO: 72            moltype = AA  length = 11
FEATURE                  Location/Qualifiers
REGION                   1..11
                         note = Synthetic Construct
source                   1..11
                         mol_type = protein
                         organism = synthetic construct
SEQUENCE: 72
AALLPVLLAA P                                                          11

SEQ ID NO: 73            moltype = AA  length = 13
FEATURE                  Location/Qualifiers
source                   1..13
                         mol_type = protein
                         organism = Human immunodeficiency virus type 1
SEQUENCE: 73
GRKKRRQRRR PPQ                                                        13

SEQ ID NO: 74            moltype = AA  length = 16
FEATURE                  Location/Qualifiers
source                   1..16
                         mol_type = protein
                         organism = Drosophila melanogaster
SEQUENCE: 74
RQIKIWFQNR RMKWKK                                                     16

SEQ ID NO: 75            moltype = DNA  length = 32
FEATURE                  Location/Qualifiers
misc_feature             1..32
                         note = Synthetic Construct
```

```
source                  1..32
                        mol_type = other DNA
                        organism = synthetic construct
SEQUENCE: 75
acagtatcca tttattatgt aatgcttctt ag                                      32

SEQ ID NO: 76           moltype = DNA  length = 22
FEATURE                 Location/Qualifiers
misc_feature            1..22
                        note = Synthetic Construct
source                  1..22
                        mol_type = other DNA
                        organism = synthetic construct
SEQUENCE: 76
tgaaaggagc gccttctaga ac                                                 22

SEQ ID NO: 77           moltype = RNA  length = 88
FEATURE                 Location/Qualifiers
source                  1..88
                        mol_type = genomic RNA
                        organism = Homo sapiens
SEQUENCE: 77
cagagtgtta ctcagaattg ggaaatccag ctagcggcag tattctgtac agtagacaca        60
agaattatgt acgcctttta tcaaagac                                           88

SEQ ID NO: 78           moltype = RNA  length = 50
FEATURE                 Location/Qualifiers
misc_feature            1..50
                        note = Synthetic Construct
source                  1..50
                        mol_type = other RNA
                        organism = synthetic construct
SEQUENCE: 78
cataattctt gtgtctactg tacagaatac tgccgccagc tggatttccc                   50
```

RNA-EDITING OLIGONUCLEOTIDES AND USES THEREOF

This application is a divisional of U.S. application Ser. No. 16/749,500, filed Jan. 22, 2020, which claims priority to U.S. Provisional Application Nos. 62/795,359, filed Jan. 22, 2019; 62/822,527, filed Mar. 22, 2019; and 62/900,011 filed Sep. 13, 2019, each of which is incorporated by reference herein in its entirety for any purpose.

REFERENCE TO SEQUENCE LISTING

The present application contains a Sequence Listing which has been submitted electronically in XML format and is hereby incorporated by reference in its entirety. Said XML copy, created on Sep. 6, 2022, is named "2022-09-06_01249-0005-01US_ST26" and is 265,415 bytes in size.

BACKGROUND

Adenosine deaminases acting on RNA (ADAR) are enzymes which bind to double-stranded RNA (dsRNA) and convert adenosine to inosine through deamination. In RNA, inosine functions similarly to guanosine for translation and replication. Thus, conversion of adenosine to inosine in an mRNA can result in a codon change that may lead to changes to the encoded protein and its functions. There are three known ADAR proteins expressed in humans, ADAR1, ADAR2, and ADAR3. ADAR1 and ADAR2 are expressed throughout the body whereas ADAR3 is expressed only in the brain. ADAR1 and ADAR2 are catalytically active, while ADAR3 is thought to be inactive.

Synthetic single-stranded oligonucleotides have been shown capable of utilizing the ADAR proteins to edit target RNAs by deaminating particular adenosines in the target RNA. The oligonucleotides are complementary to the target RNA with the exception of at least one mismatch opposite the adenosine to be deaminated. However, the previously disclosed methods have not been shown to have the required selectivity and/or stability to allow for their use as therapies. Accordingly, new oligonucleotides capable of utilizing the ADAR proteins to selectively edit target RNAs in a therapeutically effective manner are needed.

SUMMARY OF THE INVENTION

The present invention features useful compositions and methods to deaminate adenosine in target mRNAs, e.g., an adenosine which may be deaminated to produce a therapeutic result, e.g., in a subject in need thereof.

Adenosine deaminases that act on RNA (ADARs) are editing enzymes that recognize certain structural motifs of double-stranded RNA (dsRNA) and edit adenosine to inosine, resulting in recoding of amino acid codons that may lead to changes to the encoded protein and its function. The nucleobases surrounding the editing site, especially the one immediately 5' of the editing site and one immediately 3' to the editing site, which together with the editing site are termed the triplet, play an important role in the deamination of adenosine. A preference for U at the 5' position and G at the 3' position relative to the editing site, was revealed from the analysis of yeast RNAs efficiently edited by overexpressed human ADAR2 and ADAR1. See Wang et al., (2018) Biochemistry, 57: 1640-1651, Eifler et al., (2013) Biochemistry, 52: 7857-7869, and Eggington et al., (2011) Nat. Commun., 319: 1-9. Recruiting ADAR to specific sites of selected transcripts and deamination of adenosine regardless of neighboring bases holds great promise for the treatment of disease. Based on structural and modeling studies of the editing site of dsRNA/ADAR complexes, several structural features that could be incorporated into guide oligonucleotides have been identified whose properties could increase the recruitment of ADAR and increase the efficiency of editing of target RNA. Novel oligonucleotides with chemical modifications such as glycol nucleic acids (GNA), flexible nucleic acids (FNA) and serinol nucleic acids (SNA) capable of recruiting ADAR proteins and deaminating adenosine with different surrounding base compositions in target RNA are shown. In addition, structure-activity relationship (SAR) studies revealed that a 2'-O-methyl (2'-OMe) modification of the ribose of some, but not all, nucleosides in the guide oligonucleotide, in addition to triplet modifications, are compatible with efficient ADAR engagement and editing.

Exemplary embodiments of the invention are described in the enumerated paragraphs below.

E1. An oligonucleotide including the structure:

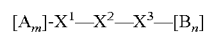

$[A_m]-X^1—X^2—X^3—[B_n]$ wherein each of A and B is a nucleotide;

m and n are each, independently, an integer from 1 to 50;

$X^1$, $X^2$, and $X^3$ are each, independently, a nucleotide, wherein at least one of $X^1$, $X^2$, or $X^3$ has the structure of any one of Formula I-VI:

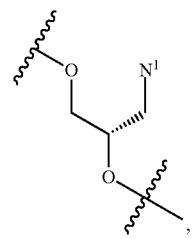

Formula I

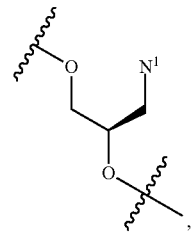

Formula II

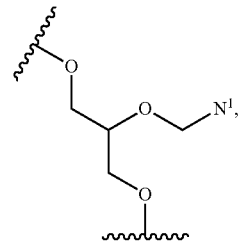

Formula III

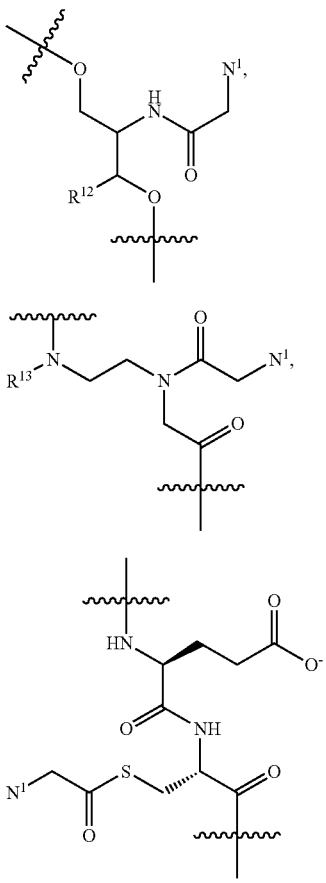

wherein $N^1$ is hydrogen or a nucleobase;
$R^{12}$ is hydrogen, hydroxy, fluoro, halogen, $C_1$-$C_6$ alkyl, $C_1$-$C_6$ heteroalkyl, or $C_1$-$C_6$ alkoxy;
$R^{13}$ is hydrogen or $C_1$-$C_6$ alkyl,
wherein at least one of $X^1$, $X^2$, or $X^3$ has the structure of any one of Formula I-IV.

E2. The oligonucleotide of E1, wherein at least 80% (e.g., at least 85%, at least 90%, at least 95%, at least 99%, or 100%) of the nucleotides of $[A_m]$ and/or $[B_n]$ include a nucleobase, a sugar, and an internucleoside linkage.

E3. The oligonucleotide of any one of E1 to E2, wherein $X^1$ includes an adenine nucleobase, $X^2$ includes a cytosine or uracil nucleobase or does not include a nucleobase, and $X^3$ includes an adenine nucleobase; $X^1$ includes an adenine nucleobase, $X^2$ includes a cytosine or uracil nucleobase or does not include a nucleobase, and $X^3$ includes a guanine or hypoxanthine nucleobase; $X^1$ includes an adenine nucleobase, $X^2$ includes a cytosine or uracil nucleobase or does not include a nucleobase, and $X^3$ includes a uracil nucleobase; $X^1$ includes an adenine nucleobase, $X^2$ includes a cytosine or uracil nucleobase or does not include a nucleobase, and $X^3$ includes a cytosine nucleobase; $X^1$ includes a guanine or hypoxanthine nucleobase, $X^2$ includes a cytosine or uracil nucleobase or does not include a nucleobase, and $X^3$ includes an adenine nucleobase; $X^1$ includes a guanine or hypoxanthine nucleobase, $X^2$ includes a cytosine or uracil nucleobase or does not include a nucleobase, and $X^3$ includes a guanine or hypoxanthine nucleobase; $X^1$ includes a guanine or hypoxanthine nucleobase, $X^2$ includes a cytosine or uracil nucleobase or does not include a nucleobase, and $X^3$ includes a uracil nucleobase; $X^1$ includes a guanine or hypoxanthine nucleobase, $X^2$ includes a cytosine or uracil nucleobase or does not include a nucleobase, and $X^3$ includes a cytosine nucleobase; $X^1$ includes a uracil nucleobase, $X^2$ includes a cytosine or uracil nucleobase or does not include a nucleobase, and $X^3$ includes an adenine nucleobase; $X^1$ includes a uracil nucleobase, $X^2$ includes a cytosine or uracil nucleobase or does not include a nucleobase, and $X^3$ includes a guanine or hypoxanthine nucleobase; $X^1$ includes a uracil nucleobase, $X^2$ includes a cytosine or uracil nucleobase or does not include a nucleobase, and $X^3$ includes a uracil nucleobase; $X^1$ includes a uracil nucleobase, $X^2$ includes a cytosine or uracil nucleobase or does not include a nucleobase, and $X^3$ includes a cytosine nucleobase; $X^1$ includes a cytosine nucleobase, $X^2$ includes a cytosine or uracil nucleobase or does not include a nucleobase, and $X^3$ includes an adenine nucleobase; $X^1$ includes a cytosine nucleobase, $X^2$ includes a cytosine or uracil nucleobase or does not include a nucleobase, and $X^3$ includes a guanine or hypoxanthine nucleobase; $X^1$ includes a cytosine nucleobase, $X^2$ includes a cytosine or uracil nucleobase or does not include a nucleobase, and $X^3$ includes a uracil nucleobase; or $X^1$ includes a cytosine nucleobase, $X^2$ includes a cytosine or uracil nucleobase or does not include a nucleobase, and $X^3$ includes a cytosine nucleobase.

E4. The oligonucleotide of any one of E1 to E3, wherein $R^{12}$ is hydrogen, halogen, $C_1$-$C_6$ alkyl, or $C_1$-$C_6$ heteroalkyl.

E5. The oligonucleotide of any one of E1 to E4, wherein the halogen is fluoro.

E6. The oligonucleotide of any one of E1 to E5, wherein $R^{12}$ is hydrogen or $C_1$-$C_6$ alkyl (e.g., $CH_3$); E7. The oligonucleotide of any one of E1 to E5, wherein $R^{12}$ is hydrogen.

E8. The oligonucleotide of any one of E1 to E7, wherein at least one of $X^1$, $X^2$, and $X^3$ has the structure of Formula I, and $N^1$ is a nucleobase.

E9. The oligonucleotide of E8, wherein $X^1$ has the structure of Formula I, and $N^1$ is a nucleobase.

E10. The oligonucleotide of E8 or E9, wherein $X^2$ has the structure of Formula I, and $N^1$ is a nucleobase.

E11. The oligonucleotide of any one of E1 to E7, wherein at least one of $X^1$, $X^2$, and $X^3$ has the structure of Formula II, and $N^1$ is a nucleobase.

E12. The oligonucleotide of E11, wherein $X^1$ has the structure of Formula II, and $N^1$ is a nucleobase.

E13. The oligonucleotide of E11 or E12, wherein $X^2$ has the structure of Formula II, and $N^1$ is a nucleobase.

E14. The oligonucleotide of any one of E1 to E7, wherein at least one of $X^1$, $X^2$, and $X^3$ has the structure of Formula IV, and $N^1$ is a nucleobase.

E15. The oligonucleotide of E14, wherein $X^1$ has the structure of Formula IV, and $N^1$ is a nucleobase.

E16. The oligonucleotide of E14 or E15, wherein $X^2$ has the structure of Formula IV, and $N^1$ is a nucleobase.

E17. The oligonucleotide of any one of E1 to E7, wherein at least one of $X^1$, $X^2$, and $X^3$ has the structure of Formula III, and $N^1$ is a nucleobase.

E18. The oligonucleotide of E17, wherein $X^1$ has the structure of Formula III, and $N^1$ is a nucleobase.

E19. The oligonucleotide of E17 or E18, wherein $X^2$ has the structure of Formula III, and $N^1$ is a nucleobase.

E20. The oligonucleotide of any one of E1 to E9 and E11 to E19, wherein $X^2$ does not have the structure of Formula I.

E21. The oligonucleotide of any one of E1 to E20, wherein $X^3$ does not have the structure of Formula I.

E22. The oligonucleotide of any one of E1 to E12 and E14 to E21, wherein $X^2$ does not have the structure of Formula II.

E23. The oligonucleotide of any one of E1 to E22, wherein $X^3$ does not have the structure of Formula II.

E24. The oligonucleotide of any one of E1 to E15 and E17 to E23, wherein $X^2$ does not have the structure of Formula IV.

E25. The oligonucleotide of any one of E1 to E7, wherein $X^2$ has the structure of Formula I or Formula II.

E26. The oligonucleotide of any one of E1 to E25, wherein
when $X^1$ has the structure of any one of Formulas I to VI, each of $X^2$ and $X^3$ is, independently, a ribonucleotide, a 2'-O—$C_1$-$C_6$ alkyl-nucleotide, a 2'-amino-nucleotide, an arabinonucleic acid-nucleotide, a bicyclic-nucleotide, a 2'-F-nucleotide, 2'-O-methoxyethyl-nucleotide, a constrained ethyl-nucleotide, a LNA-nucleotide, or a DNA-nucleotide; when $X^2$ has the structure of any one of Formulas I to VI, each of $X^1$ and $X^3$ is, independently, a ribonucleotide, a 2'-O—$C_1$-$C_6$ alkyl-nucleotide, a 2'-amino-nucleotide, an arabinonucleic acid-nucleotide, a bicyclic-nucleotide, a 2'-F-nucleotide, 2'-O-methoxyethyl-nucleotide, a constrained ethyl-nucleotide, a LNA-nucleotide, or a DNA-nucleotide; when $X^3$ has the structure of any one of Formulas I to VI, each of $X^1$ and $X^2$ is, independently, a ribonucleotide, a 2'-O—$C_1$-$C_6$ alkyl-nucleotide, a 2'-amino-nucleotide, an arabinonucleic acid-nucleotide, a bicyclic-nucleotide, a 2'-F-nucleotide, 2'-O-methoxyethyl-nucleotide, a constrained ethyl-nucleotide, a LNA-nucleotide, or a DNA-nucleotide; when $X^1$ and $X^2$ each have the structure of any one of Formulas I to VI, $X^3$ is a ribonucleotide, a 2'-O—$C_1$-$C_6$ alkyl-nucleotide, a 2'-amino-nucleotide, an arabinonucleic acid-nucleotide, a bicyclic-nucleotide, a 2'-F-nucleotide, 2'-O-methoxyethyl-nucleotide, a constrained ethyl-nucleotide, a LNA-nucleotide, or a DNA-nucleotide; when $X^1$ and $X^3$ each have the structure of any one of Formulas I to VI, $X^2$ is a ribonucleotide, a 2'-O—$C_1$-$C_6$ alkyl-nucleotide, a 2'-amino-nucleotide, an arabinonucleic acid-nucleotide, a bicyclic-nucleotide, a 2'-F-nucleotide, 2' methoxyethyl-nucleotide, a constrained ethyl-nucleotide, a LNA-nucleotide, or a DNA-nucleotide; and when $X^2$ and $X^3$ each have the structure of any one of Formulas I to VI, $X^1$ is a ribonucleotide, a 2'-O—$C_1$-$C_8$ alkyl-nucleotide, a 2'-amino-nucleotide, an arabinonucleic acid-nucleotide, a bicyclic-nucleotide, a 2'-F-nucleotide, 2'-O-methoxyethyl-nucleotide, a constrained ethyl-nucleotide, a LNA-nucleotide, or a DNA-nucleotide.

E27. The oligonucleotide of E26, wherein when $X^1$ has the structure of any one of Formulas I to VI, each of $X^2$ and $X^3$ is, independently, a ribonucleotide, a 2'-F-nucleotide, 2'-O-methoxyethyl-nucleotide, or a DNA-nucleotide; when $X^2$ has the structure of any one of Formulas I to VI, each of $X^1$ and $X^3$ is, independently, a ribonucleotide, a 2'-F-nucleotide, 2'-O-methoxyethyl-nucleotide, or a DNA-nucleotide; when $X^3$ has the structure of any one of Formulas I to VI, each of $X^1$ and $X^2$ is, independently, a ribonucleotide, a 2'-F-nucleotide, 2'-O-methoxyethyl-nucleotide, or a DNA-nucleotide; when $X^1$ and $X^2$ each have the structure of any one of Formulas I to VI, $X^3$ is a ribonucleotide, a 2'-F-nucleotide, 2'-O-methoxyethyl-nucleotide, or a DNA-nucleotide; when $X^1$ and $X^3$ each have the structure of any one of Formulas I to VI, $X^2$ is a ribonucleotide, a 2'-F-nucleotide, 2'-O-methoxyethyl-nucleotide, or a DNA-nucleotide; and when $X^2$ and $X^3$ each have the structure of any one of Formulas I to VI, $X^1$ is a ribonucleotide, a 2'-F-nucleotide, 2'-O-methoxyethyl-nucleotide, or a DNA-nucleotide.

E28. The oligonucleotide of E27, wherein when $X^1$ has the structure of any one of Formulas I to VI, each of $X^2$ and $X^3$ is a ribonucleotide; when $X^2$ has the structure of any one of Formulas I to VI, each of $X^1$ and $X^3$ is a ribonucleotide; when $X^3$ has the structure of any one of Formulas I to VI, each of $X^1$ and $X^2$ is a ribonucleotide; when $X^1$ and $X^2$ each have the structure of any one of Formulas I to VI, $X^3$ is a ribonucleotide; when $X^1$ and $X^3$ each have the structure of any one of Formulas I to VI, $X^2$ is a ribonucleotide; and when $X^2$ and $X^3$ each have the structure of any one of Formulas I to VI, $X^1$ is a ribonucleotide.

E29. The oligonucleotide of any one of E1 to E28, wherein $X^1$ includes a hypoxanthine nucleobase.

E30. The oligonucleotide of any one of E1 to E28, wherein $X^1$ includes a uracil nucleobase.

E31. The oligonucleotide of any one of E1 to E28, wherein $X^1$ includes a cytosine nucleobase.

E32. The oligonucleotide of any one of E1 to E31, wherein $X^3$ includes a hypoxanthine nucleobase.

E33. The oligonucleotide of any one of E1 to E31, wherein $X^3$ includes a guanine nucleobase.

E34. The oligonucleotide of any one of E1 to E31, wherein $X^3$ includes an adenine nucleobase E35. The oligonucleotide of any one of E1 to E34, wherein $X^2$ includes a cytosine nucleobase.

E36. The oligonucleotide of any one of E1 to E34, wherein $X^2$ includes a uracil nucleobase.

E37. The oligonucleotide of any one of E1 to E34, wherein $X^2$ does not include a nucleobase.

E38. The oligonucleotide of any one of E1 to E34, wherein $X^2$ includes a nucleobase having the structure:

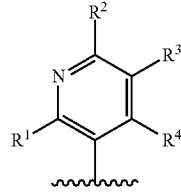

wherein $R^1$ is hydrogen, trifluoromethyl, optionally substituted amino, hydroxyl, or optionally substituted $C_1$-$C_6$ alkoxy;

$R^2$ is hydrogen, optionally substituted amino, or optionally substituted $C_1$-$C_6$ alkyl; and $R^3$ and $R^4$ are, independently, hydrogen, halogen, or optionally substituted $C_1$-$C_6$ alkyl, or a salt thereof.

E39. The oligonucleotide of any one of E1 to E38, wherein $X^2$ is not a 2'-O-methyl-nucleotide.

E40. The oligonucleotides of any one of E1 to E39, wherein $X^1$, $X^2$, and $X^3$ are not 2'-O-methyl-nucleotides.

E41. The oligonucleotide of any one of E1 to E40, wherein $[A_m]$ includes at least one nuclease resistant nucleotide.

E42. The oligonucleotide of any one of E1 to E41, wherein $[A_m]$ includes at least one 2'-O—$C_1$-$C_6$ alkyl-nucleotide, at least one 2'-amino-nucleotide, at least one arabino nucleic acid-nucleotide, at least one bicyclic-nucleotide, at least one 2'-F-nucleotide, at least one 2'-O-methoxyethyl-nucleotide, at least one constrained ethyl (cEt)-nucleotide, at least one LNA-nucleotide, and/or at least one DNA-nucleotide.

E43. The oligonucleotide of E42, wherein $[A_m]$ includes at least one 2'-O-methyl-nucleotide, at least one 2'-F-nucleotide, at least one 2'-O-methoxyethyl-nucleotide, at least one cEt-nucleotide, at least one LNA-nucleotide, and/or at least one DNA-nucleotide.

E44. The oligonucleotide of any one of E1 to E43, wherein $[A_m]$ includes at least five terminal 2'-O-methyl-nucleotides.

E45. The oligonucleotide of any one of E1 to E44, wherein $[A_m]$ includes at least one phosphorothioate linkage.

E46. The oligonucleotide of any one of E1 to E45, wherein $[A_m]$ includes at least four terminal phosphorothioate linkages.

E47. The oligonucleotide of E45 or E46, wherein at least one phosphorothioate linkage is stereopure.

E48. The oligonucleotide of any one of E1 to E57, wherein $[B_n]$ includes at least one nuclease resistant nucleotide.

E49. The oligonucleotide of any one of E1 to E48, wherein $[B_n]$ includes at least one at least one 2'-O—$C_1$-$C_6$ alkyl-nucleotide, at least one 2'-amino-nucleotide, at least one arabino nucleic acid-nucleotide, at least one bicyclic-nucleotide, at least one 2'-F-nucleotide, at least one 2'-O-methoxyethyl-nucleotide, at least one cEt-nucleotide, at least one LNA-nucleotide, and/or at least one DNA-nucleotide.

E50. The oligonucleotide of E49, wherein $[B_n]$ includes at least one 2'-O-methyl-nucleotide, at least one 2'-F-nucleotide, at least one 2'-O-methoxyethyl-nucleotide, at least one cEt-nucleotide, at least one LNA-nucleotide, and/or at least one DNA-nucleotide.

E51. The oligonucleotide of any one of E1 to E50, wherein $[B_n]$ includes at least five terminal 2'-O-methyl-nucleotides.

E52. The oligonucleotide of any one of E1 to E51, wherein $[B_n]$ includes at least one phosphorothioate linkage.

E53. The oligonucleotide of any one of E1 to E52, wherein $[B_n]$ includes at least four terminal phosphorothioate linkages.

E54. The oligonucleotide of E50 or E53, wherein at least one phosphorothioate linkage is stereopure.

E55. The oligonucleotide of any one of E1 to E54, wherein at least 20% (e.g., at least 30%, at least 40%, at least 50%, at least 60%, at least 70%, at least 80%, at least 90%, or 100%) of the nucleotides of $[A_m]$ and $[B_n]$ combined are 2'-O-methyl-nucleotides.

E56. The oligonucleotide of any one of E1 to E55, wherein the oligonucleotide further includes a 5'-cap structure.

E57. The oligonucleotide of E56, wherein the 5'-cap structure is a 2,2,7-trimethylguanosine cap.

E58. The oligonucleotide of any one of E1 to E57, wherein the oligonucleotide includes at least one alternative nucleobase.

E59. The oligonucleotide of E58, wherein the alternative nucleobase is 5-methylcytosine, 5-hydroxycytosine, 5-methoxycytosine, $N^4$-methylcytosine, $N^3$-methylcytosine, $N^4$-ethylcytosine, pseudoisocytosine, 5-fluorocytosine, 5-bromocytosine, 5-iodocytosine, 5-aminocytosine, 5-ethynylcytosine, 5-propynylcytosine, pyrrolocytosine, 5-aminomethylcytosine, 5-hydroxymethylcytosine, naphthyridine, 5-methoxyuracil, pseudouracil, dihydrouracil, 2-thiouracil, 4-thiouracil, 2-thiothymine, 4-thiothymine, 5,6-dihydrothymine, 5-halouracil, 5-propynyluracil, 5-aminomethyluracil, 5-hydroxymethyluracil, hypoxanthine, 7-deazaguanine, 8-aza-7-deazaguanine, 7-aza-2,6-diaminopurine, thienoguanine, $N^1$-methylguanine, $N^2$-methylguanine, 6-thioguanine, 8-methoxyguanine, 8-allyloxyguanine, 7-aminomethyl-7-deazaguanine, 7-methylguanine, imidazopyridopyrimidine, 7-deazaadenine, 3-deazaadenine, 8-aza-7-deazaadenine, 8-aza-7-deazaadenine, $N^1$-methyladenine, 2-methyladenine, $N^6$-methyladenine, 7-methyladenine, 8-methyladenine, or 8-azidoadenine.

E60. The oligonucleotide of E58, wherein the alternative nucleobase is 2-amino-purine, 2,6-diamino-purine, 3-deazaadenine, 7-deaza-adenine, 7-methyl-adenine, 8-azido-adenine, 8-methyl-adenine, 5-hydroxymethyl-cytosine, 5-methyl-cytosine, pyrrolo-cytosine, 7-aminomethyl-7-deaza-guanine, 7-deaza-guanine, 7-methyl-guanine, 8-aza-7-deaza-guanine, thieno-guanine, hypoxanthine, 4-thio-uracil, 5-methoxy-uracil, dihydro-uracil, or pseudouracil.

E61. The oligonucleotide of E58, wherein the alternative nucleobase is 5-methyl-cytosine or 2-amino-purine.

E62. The oligonucleotide of any one of E1 to E61, wherein the 5'-terminal nucleotide is a 2'-amino-nucleotide.

E63. The oligonucleotide of any one of E1 to E62, wherein A and B combined consist of 18 to 80 nucleotides (e.g., 27 to 71, 36 to 62, 45 to 53, or 47 to 51 nucleotides).

E64. The oligonucleotide of any one of E1 to E63, wherein m is 5 to 40 (e.g., 8 to 36, 12 to 32, 16 to 28, 20 to 24, or 30 to 40).

E65. The oligonucleotide of any one of E1 to E64, wherein n is 5 to 40 (e.g., 7 to 17, 8 to 36, 12 to 32, 16 to 28, or 20 to 24).

E66. The oligonucleotide of E1, wherein m and n are each, independently, an integer from 5 to 40; at least one of $X^1$, $X^2$, and $X^3$ has the structure of Formula I, Formula II, Formula III, or Formula IV, wherein $N^1$ is a nucleobase and each of $X^1$, $X^2$, and $X^3$ that does not have the structure of Formula I, Formula II, Formula III, or Formula IV is a ribonucleotide; $[A_m]$ and $[B_n]$ each include at least five terminal 2'-O-methyl-nucleotides and at least four terminal phosphorothioate linkages; and at least 20% of the nucleotides of $[A_m]$ and $[B_n]$ combined are 2'-O-methyl-nucleotides.

E67. The oligonucleotide of E66, wherein $X^1$ includes an adenine nucleobase, $X^2$ includes a cytosine, 5-methylcytosine, uracil, or thymine nucleobase or does not include a nucleobase, and $X^3$ includes an adenine nucleobase; $X^1$ includes an adenine nucleobase, $X^2$ includes a cytosine, 5-methylcytosine, uracil, or thymine nucleobase or does not include a nucleobase, and $X^3$ includes a guanine or hypoxanthine nucleobase; $X^1$ includes an adenine nucleobase, $X^2$ includes a cytosine, 5-methylcytosine, uracil, or thymine nucleobase or does not include a nucleobase, and $X^3$ includes a uracil or thymine nucleobase; $X^1$ includes an adenine nucleobase, $X^2$ includes a cytosine, 5-methylcytosine, uracil, or thymine nucleobase or does not include a nucleobase, and $X^3$ includes a cytosine or 5-methylcytosine nucleobase; $X^1$ includes a guanine or hypoxanthine nucleobase, $X^2$ includes a cytosine, 5-methylcytosine, uracil, or thymine nucleobase or does not include a nucleobase, and $X^3$ includes an adenine nucleobase; $X^1$ includes a guanine or hypoxanthine nucleobase, $X^2$ includes a cytosine, 5-methylcytosine, uracil, or thymine nucleobase or does not include a nucleobase, and $X^3$ includes a guanine or hypoxanthine nucleobase; $X^1$ includes a guanine or hypoxanthine nucleobase, $X^2$ includes a cytosine, 5-methylcytosine, uracil, or thymine nucleobase or does not include a nucleobase, and $X^3$ includes a uracil or thymine nucleobase; $X^1$ includes a guanine or hypoxanthine nucleobase, $X^2$ includes a cytosine, 5-methylcytosine, uracil, or thymine nucleobase or does not include a nucleobase, and $X^3$ includes a cytosine or 5-methylcytosine nucleobase; $X^1$ includes a uracil or thymine nucleobase, $X^2$ includes a cytosine, 5-methylcytosine, uracil, or thymine nucleobase or does not include a nucleobase, and $X^3$ includes an adenine nucleobase; $X^1$ includes a uracil or thymine nucleobase, $X^2$ includes a cytosine, 5-methylcytosine, uracil, or thymine nucleobase or does not include a nucleobase, and $X^3$ includes a guanine or hypoxanthine nucleobase; $X^1$ includes a uracil or thymine nucleobase, $X^2$ includes a cytosine, 5-methylcytosine, uracil, or thymine nucleobase or does not include a nucleobase, and $X^3$ includes a uracil or thymine nucleobase; $X^1$ includes a uracil or thymine nucleobase, $X^2$ includes a cytosine, 5-methylcytosine, uracil, or thymine nucleobase or does not include a nucleobase, and $X^3$ includes a cytosine or 5-methylcytosine nucleobase; $X^1$ includes a cytosine or 5-methylcytosine nucleobase, $X^2$ includes a cytosine, 5-methylcytosine, uracil, or thymine nucleobase or does not include a nucleobase, and $X^3$ includes an adenine nucleobase; $X^1$ includes a cytosine or 5-methylcytosine nucleobase, $X^2$ includes a cytosine, 5-methylcytosine, uracil, or thymine nucleobase or does not include a nucleobase, and $X^3$ includes a guanine or hypoxanthine nucleobase; $X^1$ includes a cytosine or 5-methylcytosine nucleobase, $X^2$ includes a cytosine, 5-methylcytosine, uracil, or thymine nucleobase or does not include a nucleobase, and $X^3$ includes a uracil or thymine nucleobase; or $X^1$ includes a cytosine or 5-methylcytosine nucleobase, $X^2$ includes a cytosine, 5-methylcytosine, uracil, or thymine nucleobase or does not include a nucleobase, and $X^3$ includes a cytosine or 5-methylcytosine nucleobase.

E68. The oligonucleotide of any one of E1 to E67, wherein the oligonucleotide further includes one or more adenosine deaminase acting on RNA (ADAR)-recruiting domains.

E69. The oligonucleotide of E68, wherein the oligonucleotide includes one ADAR-recruiting domain.

E70. The oligonucleotide of E69, wherein the ADAR-recruiting domain is at the 5' end of the oligonucleotide.

E71. The oligonucleotide of E69, wherein the ADAR-recruiting domain is at the 3' end of said oligonucleotide.

E72. The oligonucleotide of E68, wherein the oligonucleotide includes a first ADAR-recruiting domain and a second ADAR-recruiting domain.

E73. The oligonucleotide of E72, wherein the first ADAR-recruiting domain is at the 5' end of said oligonucleotide, wherein the second ADAR-recruiting domain is at the 3' end of said oligonucleotide.

E74. The oligonucleotide of any one of E68 to 73, wherein the oligonucleotide includes the structure of Formula VII:

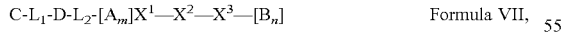   Formula VII, wherein:
[A$_m$]-X$^1$—X$^2$—X$^3$—[B$_n$] is the oligonucleotide of any one of E1 to E67;
C is a single-stranded oligonucleotide of 10-50 linked nucleosides in length;
L$_1$ is a loop region; and
D is a single-stranded oligonucleotide of 10-50 linked nucleosides in length;
L$_2$ is an optional linker;
wherein the oligonucleotide includes a duplex structure formed by C and D of between 10-50 linked nucleosides in length, wherein the duplex structure includes at least one mismatch between nucleotides of C and nucleotides of D, and wherein C or D includes at least one alternative nucleobase.

E75. The oligonucleotide of E74, wherein C and D include at least one alternative nucleobase.

E76. The oligonucleotide of E74 or E75, wherein L$_1$ includes linked nucleosides.

E77. The oligonucleotide of E76, wherein L$_1$ consists of linked nucleosides.

E78. The oligonucleotide of any one of E74 to E77, wherein L$_1$ includes at least one alternative nucleobase, at least one alternative internucleoside linkage, and/or at least one alternative sugar moiety.

E79. The oligonucleotide of any one of E74 to E77, wherein C or D includes at least one alternative internucleoside linkage and/or at least one alternative sugar moiety.

E80. The oligonucleotide of E75 to E78, wherein C and D each independently includes at least one alternative internucleoside linkage and/or at least one alternative sugar moiety.

E81. The oligonucleotide of any one of E68 to E73, wherein the oligonucleotide includes the structure of Formula VIII:

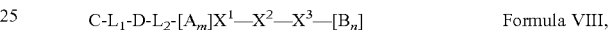   Formula VIII, wherein:
[A$_m$]-X$^1$—X$^2$—X$^3$—[B$_n$] is the oligonucleotide of any one of E1 to E67;
C is a single-stranded oligonucleotide of 10-50 linked nucleosides in length;
L$_1$ is a loop region that does not consist of linked nucleosides; and
D is a single-stranded oligonucleotide of 10-50 linked nucleosides in length;
L$_2$ is an optional linker,
wherein the oligonucleotide includes a duplex structure formed by C and D of between 10-50 linked nucleosides in length, and wherein the duplex structure includes at least one mismatch between nucleotides of C and nucleotides of D.

E82. The oligonucleotide of E81, wherein L$_1$ has the structure of Formula IX:

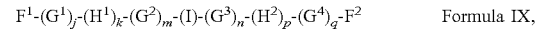   Formula IX, wherein F$^1$ is a bond between the loop region and C; F$^2$ is a bond between D and [A$_m$] or between D and, optionally, the linker; G$^1$, G$^2$, G$^3$, and G$^4$ each, independently, is selected from optionally substituted C$_1$-C$_2$ alkyl, optionally substituted C$_1$-C$_3$ heteroalkyl, O, S, and NR$^N$; R$^N$ is hydrogen, optionally substituted C$_{1-4}$ alkyl, optionally substituted C$_{2-4}$ alkenyl, optionally substituted C$_{2-4}$ alkynyl, optionally substituted C$_{2-6}$ heterocyclyl, optionally substituted C$_{6-12}$ aryl, or optionally substituted C$_{1-7}$ heteroalkyl; C$^1$ and C$^2$ are each, independently, selected from carbonyl, thiocarbonyl, sulphonyl, or phosphoryl; j, k, m, n, p, and q are each, independently, 0 or 1; and l is optionally substituted C$_{1-10}$ alkyl, optionally substituted C$_{2-10}$ alkenyl, optionally substituted C$_{2-10}$ alkynyl, optionally substituted C$_{2-6}$ heterocyclyl, optionally substituted C$_6$-12 aryl, optionally substituted C$_2$-C$_{10}$ polyethylene glycol, or optionally substituted C$_{1-10}$ heteroalkyl, or a chemical bond linking F$^1$-(G$^1$)$_j$-(H$^1$)$_k$-(G$^2$)$_m$-(I)-(G$^3$)$_n$-(H$^2$)$_p$-(G$^4$)$_q$-F$^2$.

E83. The oligonucleotide of E81 or E82, wherein L$_1$ includes a carbohydrate-containing linking moiety.

E84. The oligonucleotide of any one of E81 to E83, wherein the C or D includes at least one alternative nucleobase, at least one alternative internucleoside linkage, and/or at least one alternative sugar moiety.

E85. The oligonucleotide of any one of E81 to E83, wherein C and D each includes at least one alternative nucleobase, at least one alternative internucleoside linkage, and/or at least one alternative sugar moiety.

E86. The oligonucleotide of any one of E68 to E73, wherein the oligonucleotide includes the structure of Formula X:

$$C\text{-}L_1\text{-}D\text{-}L_2\text{-}[A_m]X^1\text{—}X^2\text{—}X^3\text{—}[B_n] \quad \text{Formula X,}$$

wherein:
[$A_m$]$X^1$—$X^2$—$X^3$—[$B_n$] is the oligonucleotide of any one of E1 to E67;
C is a single-stranded oligonucleotide of 10-50 linked nucleosides in length;
$L_1$ is a loop region including at least one alternative nucleobase or at least one alternative internucleoside linkage; and
D is a single-stranded oligonucleotide of 10-50 linked nucleosides in length;
$L_2$ is an optional linker,
wherein the oligonucleotide includes a duplex structure formed by C and D of between 10-50 linked nucleosides in length, and wherein the duplex structure includes at least one mismatch between nucleotides of C and nucleotides of D.

E87. The oligonucleotide of E86, wherein $L_1$ includes at least one alternative nucleobase and at least one alternative internucleoside linkage.

E88. The oligonucleotide of any one of E68 to E73, wherein the oligonucleotide includes the structure of Formula XI:

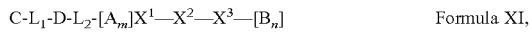
$$C\text{-}L_1\text{-}D\text{-}L_2\text{-}[A_m]X^1\text{—}X^2\text{—}X^3\text{—}[B_n] \quad \text{Formula XI,}$$

wherein:
[$A_m$]-$X^1$—$X^2$—$X^3$—[$B_n$] is the oligonucleotide of any one of E1 to E67;
C is a single-stranded oligonucleotide of 10-50 linked nucleosides in length;
$L_1$ is a loop region including at least one alternative sugar moiety, wherein the alternative sugar moiety is selected from the group consisting of a 2'-O—$C_1$-$C_6$ alkyl-sugar moiety, a 2'-amino-sugar moiety, a 2'-fluoro-sugar moiety, a 2'-O-MOE sugar moiety, an arabino nucleic acid (ANA) sugar moiety, a deoxyribose sugar moiety, and a bicyclic nucleic acid; and
D is a single-stranded oligonucleotide of 10-50 linked nucleosides in length;
$L_2$ is an optional linker,
wherein the oligonucleotide includes a duplex structure formed by C and D of between 10-50 linked nucleosides in length, and wherein the duplex structure includes at least one mismatch between nucleotides of C and nucleotides of D.

E89. The oligonucleotide of E87, wherein the bicyclic sugar moiety is selected from an oxy-LNA sugar moiety, a thio-LNA sugar moiety, an amino-LNA sugar moiety, a cEt sugar moiety, and an ethylene-bridged (ENA) sugar moiety, and an LNA sugar moiety.

E90. The oligonucleotide of E88 or E89, wherein the ANA sugar moiety is a 2'-fluoro-ANA sugar moiety.

E91. The oligonucleotide of any one of E86 to E90, wherein C or D include at least one alternative nucleobase, at least one alternative internucleoside linkage, and/or at least one alternative sugar moiety.

E92. The oligonucleotide of any one of E86 to E90, wherein C and D each includes at least one alternative nucleobase, at least one alternative internucleoside linkage, and/or at least one alternative sugar moiety.

E93. The oligonucleotide of any one of E74 to E92, wherein C is complementary to at least 5 contiguous nucleobases of D.

E94. The oligonucleotide of any one of E74 to E92, wherein at least 80% (e.g., at least 85%, at least 90%, at least 95%, at least 99%, or 100%) of the nucleobases of C are complementary to the nucleobases of D.

E95. The oligonucleotide of any one of E74 to E92, wherein C includes a nucleobase sequence having at least 80% sequence identity to a nucleobase sequence set forth in any one of SEQ ID NO. 1, 4, 7, 10, 13, 16, 19, 22, 25, 28, 31, and 34.

E96. The oligonucleotide of any one of E74 to E95, wherein D includes a nucleobase sequence having at least 80% sequence identity to a nucleobase sequence set forth in any one of SEQ ID NOs. 2, 5, 8, 11, 14, 17, 20, 23, 26, 29, 32, and 35.

E97. The oligonucleotide of any one of E74 to E96, wherein C-$L_1$-D includes a nucleobase sequence having at least 80% sequence identity to a nucleobase sequence set forth in any one of SEQ ID NOs. 3, 6, 9, 12, 15, 18, 21, 24, 27, 30, 33, and 36.

E98. The oligonucleotide of any one of E74 to E80, E84 to E87, E91, and E92, wherein the at least one alternative nucleobase is selected from the group consisting of 5-methylcytosine, 5-hydroxycytosine, 5-methoxycytosine, $N^4$-methylcytosine, $N^3$-methylcytosine, $N^4$-ethylcytosine, pseudoisocytosine, 5-fluorocytosine, 5-bromocytosine, 5-iodocytosine, 5-aminocytosine, 5-ethynylcytosine, 5-propynylcytosine, pyrrolocytosine, 5-aminomethylcytosine, 5-hydroxymethylcytosine, naphthyridine, 5-methoxyuracil, pseudouracil, dihydrouracil, 2-thiouracil, 4-thiouracil, 2-thiothymine, 4-thiothymine, 5,6-dihydrothymine, 5-halouracil, 5-propynyluracil, 5-aminomethyluracil, 5-hydroxymethyluracil, hypoxanthine, 7-deazaguanine, 8-aza-7-deazaguanine, 7-aza-2,6-diaminopurine, thienoguanine, $N^1$-methylguanine, $N^2$-methylguanine, 6-thioguanine, 8-methoxyguanine, 8-allyloxyguanine, 7-aminomethyl-7-deazaguanine, 7-methylguanine, imidazopyridopyrimidine, 7-deazaadenine, 3-deazaadenine, 8-aza-7-deazaadenine, 8-aza-7-deazaadenine, $N^1$-methyladenine, 2-methyladenine, $N^6$-methyladenine, 7-methyladenine, 8-methyladenine, or 8-azidoadenine.

E99. The oligonucleotide of any one of E74 to E80, E84 to E87, E91, or E92, wherein the at least one alternative nucleobase is selected from the group consisting of 2-aminopurine, 2,6-diamino-purine, 3-deaza-adenine, 7-deaza-adenine, 7-methyl-adenine, 8-azido-adenine, 8-methyl-adenine, 5-hydroxymethyl-cytosine, 5-methyl-cytosine, pyrrolo-cytosine, 7-aminomethyl-7-deaza-guanine, 7-deaza-guanine, 7-methyl-guanine, 8-aza-7-deaza-guanine, thienoguanine, hypoxanthine, 4-thio-uracil, 5-methoxy-uracil, dihydro-uracil, or pseudouracil.

E100. The oligonucleotide of any one of E74 to E80, E84 to E87, E91, or E92, wherein the at least one alternative internucleoside linkage is selected from the group consisting of a phosphorothioate internucleoside linkage, a 2'-alkoxy internucleoside linkage, and an alkyl phosphate internucleoside linkage.

E101. The oligonucleotide of E100, wherein the at least one alternative internucleoside linkage is at least one phosphorothioate internucleoside linkage.

E102. The oligonucleotide of any one of E79, E81, E84, E85, E89, or E92, wherein the at least one alternative sugar moiety is selected from the group consisting of a 2'-O-alkyl-sugar moiety, a 2'-O-methyl-sugar moiety, a 2'-amino-sugar moiety, a 2'-fluoro-sugar moiety, a 2'-O-MOE sugar moiety, an ANA sugar moiety, a deoxyribose sugar moiety, and a bicyclic nucleic acid.

E103. The oligonucleotide of E102, wherein the bicyclic sugar moiety is selected from an oxy-LNA sugar moiety, a thio-LNA sugar moiety, an amino-LNA sugar moiety, a cEt sugar moiety, and an ethylene-bridged (ENA) sugar moiety, and an LNA sugar moiety.

E104. The oligonucleotide of E102 or E103, wherein the ANA sugar moiety is a 2'-fluoro-ANA sugar moiety.

E105. The oligonucleotide of E102, wherein the at least one alternative sugar moiety is a 2'-O-methyl-sugar moiety, a 2'-fluoro-sugar moiety, or a 2'-O-MOE sugar moiety.

E106. The oligonucleotide of any one of E75 to E105, wherein the at least one mismatch is a paired A to C mismatch, a paired G to G mismatch, or a paired C to A mismatch.

E107. The oligonucleotide of E106, wherein the oligonucleotide includes at least two mismatches between nucleotides of C and nucleotides of D.

E108. The oligonucleotide of E107, wherein the at least two mismatches are separated by at least three linked nucleosides.

E109. The oligonucleotide of E108, wherein the at least two mismatches are separated by three linked nucleosides.

E110. The oligonucleotide of any one of E74 to E109, wherein the at least one mismatch includes a nucleoside having an alternative nucleobase.

E111. The oligonucleotide of E110, wherein the alternative nucleobase has the structure:

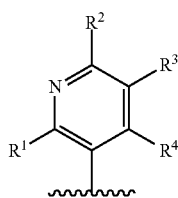

wherein $R^1$ is hydrogen, trifluoromethyl, optionally substituted amino, hydroxyl, or optionally substituted $C_1$-$C_6$ alkoxy;

$R^2$ is hydrogen, optionally substituted amino, or optionally substituted $C_1$-$C_6$ alkyl; and $R^3$ and $R^4$ are, independently, hydrogen, halogen, or optionally substituted $C_1$-$C_6$ alkyl, or a salt thereof.

E112. The oligonucleotide of any one of E74 to E111, wherein C-$L_1$-D is an ADAR-recruiting domain.

E113. The oligonucleotide of any one of E69 to E73 or E112, wherein the one or more ADAR-recruiting domains are glutamate ionotropic receptor AMPA type subunit 2 (GluR2) ADAR-recruiting domains.

E114. The oligonucleotide of E113, wherein the GluR2 ADAR-recruiting domain has the nucleotide sequence of SEQ ID NO. 37.

E115. The oligonucleotide of E114, wherein the oligonucleotide includes the structure of Formula XII:

Formula XII

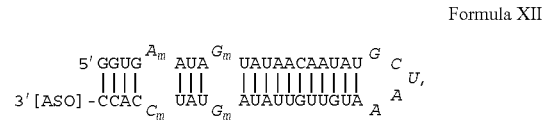

wherein [ASO] includes the oligonucleotide of any one of E1 to E67, wherein m designates a mismatched nucleotide.

E116. The oligonucleotide of E113, wherein the GluR2 ADAR-recruiting domain has the nucleotide sequence of SEQ ID NO. 38.

E117. The oligonucleotide of E116, wherein the oligonucleotide includes the structure of Formula XIII:

Formula XIII

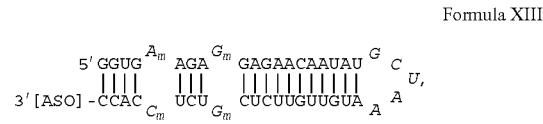

wherein [ASO] includes the oligonucleotide of any one of E1 to E67, wherein m designates a mismatched nucleotide.

E118. The oligonucleotide of E113, wherein the GluR2 ADAR-recruiting domain has the nucleotide sequence of SEQ ID NO. 39.

E119. The oligonucleotide of E118, wherein the oligonucleotide includes the structure of Formula XIV:

Formula XIV

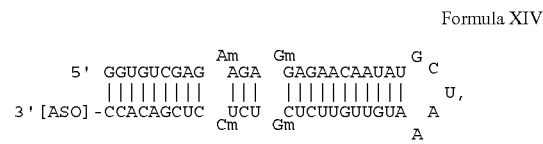

wherein [ASO] includes the oligonucleotide of any one of E1 to E67, wherein m designates a mismatched nucleotide.

E120. The oligonucleotide of E117, wherein the GluR2 ADAR-recruiting domain has the nucleotide sequence of SEQ ID NO. 40.

E121. The oligonucleotide of any one of E68 to E73 or E112 to E120, wherein the one or more ADAR-recruiting domains include at least one nuclease-resistant nucleotide.

E122. The oligonucleotide of E121, wherein the nuclease-resistant nucleotide is a 2'-O-methyl-nucleotide.

E123. The oligonucleotide of any one of E68 to E73 or E118 to E122, wherein the one or more ADAR-recruiting domains include at least one alternative internucleoside linkage.

E124. The oligonucleotide of E123, wherein the alternative internucleoside linkage is a phosphorothioate internucleoside linkage.

E125. The oligonucleotide of any one of E121 to E124, wherein the oligonucleotide includes the structure of Formula XV:

Formula XV

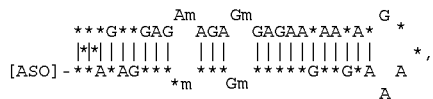

wherein [ASO] includes the oligonucleotide of any one of E1 to E67, wherein * is a 2'-O-methyl nucleotide, wherein s is a phosphorothioate internucleoside linkage, wherein m designates a mismatched nucleotide.

E126. The oligonucleotide of E113, wherein the GluR2 ADAR-recruiting domain has the nucleotide sequence of SEQ ID NO. 41.

E127. The oligonucleotide of E126, wherein the oligonucleotide includes the structure of Formula XVI:

Formula XVI

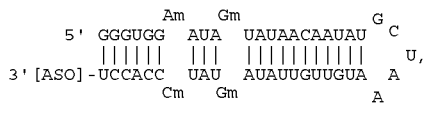

wherein [ASO] includes the oligonucleotide of any one of E1 to E67, wherein m designates a mismatched nucleotide.

E128. The oligonucleotide of E113, wherein the GluR2 ADAR-recruiting domain has the nucleotide sequence of SEQ ID NO. 42.

E129. The oligonucleotide of E128, wherein the oligonucleotide includes the structure of Formula XVII:

Formula XVII

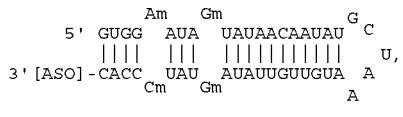

wherein [ASO] includes the oligonucleotide of any one of E1 to E67, wherein m designates a mismatched nucleotide.

E130. The oligonucleotide of E113, wherein the GluR2 ADAR-recruiting domain has the nucleotide sequence of SEQ ID NO. 43.

E131. The oligonucleotide of E130, wherein the oligonucleotide includes the structure of Formula XVIII:

Formula XVIII

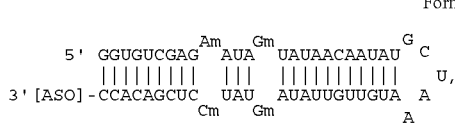

wherein [ASO] includes the oligonucleotide of any one of E1 to E67, wherein m designates a mismatched nucleotide.

E132. The oligonucleotide of E113, wherein the GluR2 ADAR-recruiting domain has the nucleotide sequence of SEQ ID NO. 44.

E133. The oligonucleotide of E132, wherein the oligonucleotide includes the structure of Formula XIX:

Formula XIX

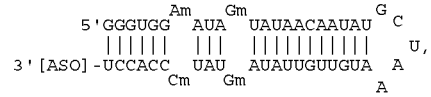

wherein [ASO] includes the oligonucleotide of any one of E1 to E67, wherein m designates a mismatched nucleotide.

E134. The oligonucleotide of E113, wherein the GluR2 ADAR-recruiting domain has the nucleotide sequence of SEQ ID NO. 45.

E135. The oligonucleotide of E134, wherein the oligonucleotide includes the structure of Formula XX:

Formula XX

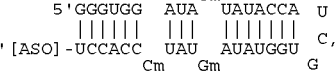

wherein [ASO] includes the oligonucleotide of any one of E1 to E67, wherein m designates a mismatched nucleotide.

E136. The oligonucleotide of E113, wherein the GluR2 ADAR-recruiting domain has the nucleotide sequence of SEQ ID NO. 46.

E137. The oligonucleotide of E136, wherein the oligonucleotide includes the structure of Formula XXI:

Formula XXI

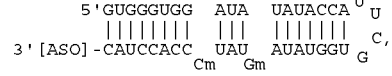

wherein [ASO] includes the oligonucleotide of any one of E1 to E67, wherein m designates a mismatched nucleotide.

E138. The oligonucleotide of E113, wherein the GluR2 ADAR-recruiting domain has the nucleotide sequence of SEQ ID NO. 47.

E139. The oligonucleotide of E138, wherein the oligonucleotide includes the structure of Formula XXII:

Formula XXII

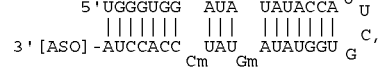

wherein [ASO] includes the oligonucleotide of any one of E1 to E67, wherein m designates a mismatched nucleotide.

E140. The oligonucleotide of E113, wherein the GluR2 ADAR-recruiting domain has the nucleotide sequence of SEQ ID NO. 48.

E141. The oligonucleotide of E140, wherein the oligonucleotide includes the structure of Formula XXIII:

```
                                                    Formula XXIII
     5'GGUGG A_m  AUA G_m  UAUACCA U
          |||||    |||    ||||||| U
     3'[ASO]-CCACC C_m  UAU G_m  AUAUGGU G C,
``` wherein [ASO] includes the oligonucleotide of any one of E1 to E67, wherein m designates a mismatched nucleotide.

E142. The oligonucleotide of E113, wherein the GluR2 ADAR-recruiting domain has the nucleotide sequence of SEQ ID NO. 49.

E143. The oligonucleotide of E142, wherein the oligonucleotide includes the structure of Formula XXIV:

```
                                                    Formula XXIV
     5'GUGG A_m  AUA G_m  UAUACCA U
         ||||     |||    ||||||| U
     3'[ASO]-CACC C_m  UAU G_m  AUAUGGU G C,
``` wherein [ASO] includes the oligonucleotide of any one of E1 to E67, wherein m designates a mismatched nucleotide.

E144. The oligonucleotide of any one of E68 to E73, wherein the one or more ADAR-recruiting domains are Z-DNA ADAR-recruiting domains.

E145. The oligonucleotide of any one of E68 to E73, wherein the one or more ADAR-recruiting domains are MS2 ADAR-recruiting domains.

E146. The oligonucleotide of E145, wherein the MS2 ADAR-recruiting domain has the nucleotide sequence of SEQ ID NO. 50.

E147. A conjugate including an oligonucleotide of any one of E1 to E146 conjugated to a targeting moiety.

E148. The conjugate of E147, wherein the targeting moiety is a lipid, a sterol, a carbohydrate, and/or a peptide.

E149. The conjugate of E148, wherein the oligonucleotide is conjugated to a sterol.

E150. The conjugate of E149, wherein the sterol is cholesterol.

E151. The conjugate of any one of E148 to E150, wherein the oligonucleotide is conjugated to a carbohydrate.

E152. The conjugate of E151, wherein the carbohydrate is N-acetylgalactosamine.

E153. The conjugate of any one of E148 to E152, wherein the oligonucleotide is conjugated to a peptide.

E154. The conjugate of E153, wherein the peptide is a cell-penetrating peptide.

E155. The conjugate of any one of E148 to E154, wherein the oligonucleotide is conjugated to a lipid.

E156. The conjugate of E155, wherein the lipid is litho-cholic acid, docosahexaenoic acid, or docosanoic acid.

E157. A complex including:
an oligonucleotide of any one of E1 to E146 or a conjugate of any one of E147 to E156; and
an mRNA,
wherein the oligonucleotide or conjugate and mRNA are hybridized to each other and the complex includes a first mismatch at an adenosine of the mRNA.

E158. The complex of E157, wherein the complex includes a second mismatch that is four nucleotides 5' to the first mismatch.

E159. The complex of E157 or E158, wherein the complex includes one, two, three, four, five, six, seven, or eight mismatches.

E160. The complex of any one of E157 to E159, wherein the mRNA includes an adenosine which may be deaminated to produce a therapeutic result.

E161. The complex of any one of E157 to E159, wherein the mRNA includes a guanosine to adenosine mutation compared to the corresponding natural mRNA.

E162. The complex of E161, wherein the guanosine to adenosine mutation is a missense or nonsense mutation.

E163. The complex of any one of E157 to E162, wherein the first mismatch is at an adenosine in a start codon of the mRNA.

E164. The complex of any one of E157 to E162, wherein the first mismatch is at an adenosine in a stop codon of the mRNA.

E165. The complex of E164, wherein the stop codon is a premature stop codon.

E166. A method of producing a complex of any one of E157 to E165, the method including contacting a cell with an oligonucleotide of any one of E1 to E146 or a conjugate of any one of E147 to E156.

E167. A method for deamination of an adenosine in an mRNA, the method including contacting a cell with an oligonucleotide of any one of E1 to E146 or a conjugate of any one of E147 to E156.

E168. A method of treating a disorder in a subject in need thereof, the method including administering to the subject an effective amount of an oligonucleotide of any one of E1 to E146 or a conjugate of any one of E147 to E156.

E169. The method of E168, wherein the disorder is cystic fibrosis, albinism, alpha-1-antitrypsin deficiency, Alzheimer disease, amyotrophic lateral sclerosis, asthma, 11-thalassemia, Cadasil syndrome, Charcot-Marie-Tooth disease, chronic obstructive pulmonary disease, distal spinal muscular atrophy, Duchenne/Becker muscular, dystrophy, dystrophic epidermolysis bullosa, epidermylosis bullosa, Fabry disease, Factor V Leiden associated disorders, familial adenomatous, polyposis, galactosemia, Gaucher's disease, glucose-6-phosphate dehydrogenase deficiency, haemophilia, hereditary hematochromatosis, Hunter syndrome, Huntington's disease, Hurler syndrome, inflammatory bowel disease, inherited polyagglutination syndrome, Leber congenital amaurosis, Lesch-Nyhan syndrome, Lynch syndrome, Marfan syndrome, mucopolysaccharidosis, muscular dystrophy, myotonic dystrophy types I and II, neurofibromatosis, Niemann-Pick disease type A, B and C, NY-ESO-1 related cancer, Parkinson's disease, Peutz-Jeghers syndrome, phenylketonuria, Pompe's disease, primary ciliary disease, prothrombin mutation related disorders (e.g., prothrombin G20210A mutation), pulmonary hypertension, retinitis pigmentosa, Sandhoff disease, severe combined immune deficiency syndrome, sickle cell anemia, spinal muscular atrophy, Stargardt's Disease, Tay-Sachs disease, Usher syndrome, X-linked immunodeficiency, Sturge-Weber syndrome, Rett syndrome, or cancer.

E170. The method of any one of E167 to E169, wherein the method further includes administering an ADAR fusion protein to the cell or to the subject.

E171. The method of E170, wherein the ADAR fusion protein is administered to the cell or to the subject using an expression vector construct including a polynucleotide encoding an ADAR fusion protein.

E172. The method of E170 or E171, wherein the ADAR fusion protein includes a deaminase domain of ADAR fused to an MS2 bacteriophage coat protein.

E173. The method of E172, wherein the deaminase domain of ADAR is a deaminase domain of ADAR1.

E174. The method of E172, wherein the deaminase domain of ADAR is a deaminase domain of ADAR2.

E175. The method of E168 to E174, wherein administering includes parenteral administration, intrathecal administration, or intracranial administration.

Chemical Terms

The terminology employed herein is for the purpose of describing particular embodiments and is not intended to be limiting.

For any of the following chemical definitions, a number following an atomic symbol indicates that total number of atoms of that element that are present in a particular chemical moiety. As will be understood, other atoms, such as H atoms, or substituent groups, as described herein, may be present, as necessary, to satisfy the valences of the atoms. For example, an unsubstituted $C_2$ alkyl group has the formula —$CH_2CH_3$. When used with the groups defined herein, a reference to the number of carbon atoms includes the divalent carbon in acetal and ketal groups but does not include the carbonyl carbon in acyl, ester, carbonate, or carbamate groups. A reference to the number of oxygen, nitrogen, or sulfur atoms in a heteroaryl group only includes those atoms that form a part of a heterocyclic ring.

When a particular substituent may be present multiple times in the same structure, each instance of the substituent may be independently selected from the list of possible definitions for that substituent.

The term "alkyl," as used herein, refers to a branched or straight-chain monovalent saturated aliphatic hydrocarbon radical of 1 to 20 carbon atoms (e.g., 1 to 16 carbon atoms, 1 to 10 carbon atoms, 1 to 6 carbon atoms, or 1 to 3 carbon atoms).

An alkylene is a divalent alkyl group. The term "alkenyl," as used herein, alone or in combination with other groups, refers to a straight chain or branched hydrocarbon residue having a carbon-carbon double bond and having 2 to 20 carbon atoms (e.g., 2 to 16 carbon atoms, 2 to 10 carbon atoms, 2 to 6 carbon atoms, or 2 carbon atoms).

The term "halogen," as used herein, means a fluorine (fluoro), chlorine (chloro), bromine (bromo), or iodine (iodo) radical.

The term "heteroalkyl," as used herein, refers to an alkyl group, as defined herein, in which one or more of the constituent carbon atoms have been replaced by nitrogen, oxygen, or sulfur. In some embodiments, the heteroalkyl group can be further substituted with 1, 2, 3, or 4 substituent groups as described herein for alkyl groups. Examples of heteroalkyl groups are an "alkoxy" which, as used herein, refers alkyl-O— (e.g., methoxy and ethoxy). A heteroalkylene is a divalent heteroalkyl group. The term "heteroalkenyl," as used herein, refers to an alkenyl group, as defined herein, in which one or more of the constituent carbon atoms have been replaced by nitrogen, oxygen, or sulfur. In some embodiments, the heteroalkenyl group can be further substituted with 1, 2, 3, or 4 substituent groups as described herein for alkenyl groups. Examples of heteroalkenyl groups are an "alkenoxy" which, as used herein, refers alkenyl-O—. A heteroalkenylene is a divalent heteroalkenyl group. The term "heteroalkynyl," as used herein, refers to an alkynyl group, as defined herein, in which one or more of the constituent carbon atoms have been replaced by nitrogen, oxygen, or sulfur. In some embodiments, the heteroalkynyl group can be further substituted with 1, 2, 3, or 4 substituent groups as described herein for alkynyl groups. Examples of heteroalkynyl groups are an "alkynoxy" which, as used herein, refers alkynyl-O—. A heteroalkynylene is a divalent heteroalkynyl group.

The term "hydroxy," as used herein, represents an —OH group.

The alkyl, heteroalkyl groups may be substituted or unsubstituted. When substituted, there will generally be 1 to 4 substituents present, unless otherwise specified. Substituents include, for example: alkyl (e.g., unsubstituted and substituted, where the substituents include any group described herein, e.g., aryl, halo, hydroxy), aryl (e.g., substituted and unsubstituted phenyl), carbocyclyl (e.g., substituted and unsubstituted cycloalkyl), halo (e.g., fluoro), hydroxyl, heteroalkyl (e.g., substituted and unsubstituted methoxy, ethoxy, or thioalkoxy), heteroaryl, heterocyclyl, amino (e.g., $NH_2$ or mono- or dialkyl amino), azido, cyano, nitro, or thiol. Aryl, carbocyclyl (e.g., cycloalkyl), heteroaryl, and heterocyclyl groups may also be substituted with alkyl (unsubstituted and substituted such as arylalkyl (e.g., substituted and unsubstituted benzyl)).

Compounds of the invention can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates, or mixtures of diastereoisomeric racemates. The optically active forms can be obtained for example by resolution of the racemates, by asymmetric synthesis or asymmetric chromatography (chromatography with a chiral adsorbent or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art. "Racemate" or "racemic mixture" means a compound containing two enantiomers, wherein such mixtures exhibit no optical activity; i.e., they do not rotate the plane of polarized light. "Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide 35 of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99%, or 99.9% by weight relative to the other stereoisomers. When a single enantiomer is named or depicted by structure, the depicted or named enantiomer is at least 60%, 70%, 80%, 90%, 99%, or 99.9% by weight optically pure. When a single diastereomer is named or depicted by structure, the depicted or named diastereomer is at least 60%, 70%, 80%, 90%, 99%, or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99%, or 99.9% by mole fraction pure relative to the other stereoisomers. When a single enantiomer is named or depicted by structure, the depicted or named enantiomer is at least 60%, 70%, 80%, 90%, 99%, or 99.9% by mole fraction pure. When a single diastereomer is named or depicted by structure, the depicted or named diastereomer is at least 60%, 70%, 80%, 90%, 99%, or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound, or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s), or mixtures of diastereomers in which one or more diastereomer is enriched relative to the other diastereomers. The invention embraces all of these forms.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Definitions

For convenience, the meaning of some terms and phrases used in the specification, examples, and appended claims are provided below. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

In this application, unless otherwise clear from context, (i) the term "a" may be understood to mean "at least one"; (ii) the term "or" may be understood to mean "and/or"; and (iii) the terms "including" and "comprising" may be understood to encompass itemized components or steps whether presented by themselves or together with one or more additional components or steps.

As used herein, the terms "about" and "approximately" refer to a value that is within 10% above or below the value being described. For example, the term "about 5 nM" indicates a range of from 4.5 to 5.5 nM.

The term "at least" prior to a number or series of numbers is understood to include the number adjacent to the term "at least", and all subsequent numbers or integers that could logically be included, as clear from context. For example, the number of nucleotides in a nucleic acid molecule must be an integer. For example, "at least 18 nucleotides of a 21-nucleotide nucleic acid molecule" means that 18, 19, 20, or 21 nucleotides have the indicated property. When at least is present before a series of numbers or a range, it is understood that "at least" can modify each of the numbers in the series or range.

As used herein, "no more than" or "less than" is understood as the value adjacent to the phrase and logical lower values or integers, as logical from context, to zero. For example, an oligonucleotide with "no more than 5 unmodified nucleotides" has 5, 4, 3, 2, 1, or 0 unmodified nucleotides. When "no more than" is present before a series of numbers or a range, it is understood that "no more than" can modify each of the numbers in the series or range.

As used herein, the term "administration" refers to the administration of a composition (e.g., a compound or a preparation that includes a compound as described herein) to a subject or system. Administration to an animal subject (e.g., to a human) may be by any appropriate route, such as the one described herein.

As used herein, a "combination therapy" or "administered in combination" means that two (or more) different agents or treatments are administered to a subject as part of a defined treatment regimen for a particular disease or condition. The treatment regimen defines the doses and periodicity of administration of each agent such that the effects of the separate agents on the subject overlap. In some embodiments, the delivery of the two or more agents is simultaneous or concurrent and the agents may be co-formulated. In some embodiments, the two or more agents are not co-formulated and are administered in a sequential manner as part of a prescribed regimen. In some embodiments, administration of two or more agents or treatments in combination is such that the reduction in a symptom, or other parameter related to the disorder is greater than what would be observed with one agent or treatment delivered alone or in the absence of the other. The effect of the two treatments can be partially additive, wholly additive, or greater than additive (e.g., synergistic). Sequential or substantially simultaneous administration of each therapeutic agent can be performed by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination may be administered by intravenous injection while a second therapeutic agent of the combination may be administered orally.

"G," "C," "A," "T," and "U" each generally stand for a naturally-occurring nucleotide that contains guanine, cytosine, adenine, thymidine, and uracil as a base, respectively. However, it will be understood that the term "nucleotide" can also refer to an alternative nucleotide, as further detailed below, or a surrogate replacement moiety. The skilled person is well aware that guanine, cytosine, adenine, and uracil can be replaced by other moieties without substantially altering the base pairing properties of an oligonucleotide including a nucleotide bearing such replacement moiety. For example, without limitation, a nucleotide including inosine as its base can base pair with nucleotides containing adenine, cytosine, or uracil. Hence, nucleotides containing uracil, guanine, or adenine can be replaced in the nucleotide sequences of oligonucleotides featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the invention.

The terms "nucleobase" and "base" include the purine (e.g. adenine and guanine) and pyrimidine (e.g. uracil, thymine, and cytosine) moiety present in nucleosides and nucleotides which form hydrogen bonds in nucleic acid hybridization. In the context of the present invention, the term nucleobase also encompasses alternative nucleobases which may differ from naturally-occurring nucleobases but are functional during nucleic acid hybridization. In this context "nucleobase" refers to both naturally occurring nucleobases such as adenine, guanine, cytosine, thymidine, uracil, xanthine, and hypoxanthine, as well as alternative nucleobases. Such variants are for example described in Hirao et al (2012) Accounts of Chemical Research vol 45, page 2055 and Bergstrom (2009) Current Protocols in Nucleic Acid Chemistry Suppl. 37 1.4.1.

In a some embodiments the nucleobase moiety is modified by changing the purine or pyrimidine into a modified purine or pyrimidine, such as substituted purine or substituted pyrimidine, such as an "alternative nucleobase" selected from isocytosine, pseudoisocytosine, 5-methylcytosine, 5-thiozolo-cytosine, 5-propynyl-cytosine, 5-propynyl-uracil, 5-bromouracil, 5-thiazolo-uracil, 2-thio-uracil, pseudouracil, 1-methylpseudouracil, 5-methoxyuracil, 2'-thio-thymine, hypoxanthine, diaminopurine, 6-aminopurine, 2-aminopurine, 2,6-diaminopurine, and 2-chloro-6-aminopurine.

The nucleobase moieties may be indicated by the letter code for each corresponding nucleobase, e.g. A, T, G, C, or U, wherein each letter may optionally include alternative nucleobases of equivalent function. In some embodiments, e.g., for gapmers, 5-methylcytosine LNA nucleosides may be used.

A "sugar" or "sugar moiety," includes naturally occurring sugars having a furanose ring. A sugar also includes an "alternative sugar," defined as a structure that is capable of replacing the furanose ring of a nucleoside. In certain embodiments, alternative sugars are non-furanose (or 4'-substituted furanose) rings or ring systems or open systems. Such structures include simple changes relative to the natural furanose ring, such as a six-membered ring, or may be more complicated as is the case with the non-ring system used in peptide nucleic acid. Alternative sugars may also include sugar surrogates wherein the furanose ring has been replaced with another ring system such as, for example, a morpholino or hexitol ring system. Sugar moieties useful in the preparation of oligonucleotides having motifs include, without limitation, β-D-ribose, β-D-2'-deoxyribose, substituted sugars (such as 2', 5' and bis substituted sugars), 4'-S-sugars (such as 4'-S-ribose, 4'-S-2'-deoxyribose and 4'-S-2'-substituted ribose), bicyclic alternative sugars (such as the 2'-O—CH$_2$-4' or 2'-O—(CH$_2$)$_2$-4' bridged ribose derived bicyclic sugars) and sugar surrogates (such as when the ribose ring has been replaced with a morpholino or a hexitol ring system). The type of heterocyclic base and internucleoside linkage used at each position is variable and is not a factor in determining the motif. In most nucleosides having an alternative sugar moiety, the heterocyclic nucleobase is generally maintained to permit hybridization.

A "nucleotide," as used herein refers to a monomeric unit of an oligonucleotide or polynucleotide that includes a nucleoside and an internucleoside linkage. The internucleoside linkage may or may not include a phosphate linkage. Similarly, "linked nucleosides" may or may not be linked by phosphate linkages. Many "alternative internucleoside linkages" are known in the art, including, but not limited to, phosphorothioate and boronophosphate linkages. Alternative nucleosides include bicyclic nucleosides (BNAs) (e.g., locked nucleosides (LNAs) and constrained ethyl (cEt) nucleosides), peptide nucleosides (PNAs), phosphotriesters, phosphorothionates, phosphoramidates, and other variants of the phosphate backbone of native nucleoside, including those described herein.

An "alternative nucleotide" as used herein, refers to a nucleotide having an alternative nucleoside or an alternative sugar, and an internucleoside linkage, which may include alternative nucleoside linkages.

The term "nucleoside" refers to a monomeric unit of an oligonucleotide or a polynucleotide having a nucleobase and a sugar moiety. A nucleoside may include those that are naturally-occurring as well as alternative nucleosides, such as those described herein. The nucleobase of a nucleoside may be a naturally-occurring nucleobase or an alternative nucleobase. Similarly, the sugar moiety of a nucleoside may be a naturally-occurring sugar or an alternative sugar.

The term "alternative nucleoside" refers to a nucleoside having an alternative sugar or an alternative nucleobase, such as those described herein.

The term "nuclease resistant nucleotide" as used herein refers to nucleotides which limit nuclease degradation of oligonucleotides. Nuclease resistant nucleotides generally increase stability of oligonucleotides by being poor substrates for the nucleases. Nuclease resistant nucleotides are known in the art, e.g., 2'-O-methyl-nucleotides and 2'-fluoro-nucleotides.

The terms "oligonucleotide" and "polynucleotide" as used herein, are defined as it is generally understood by the skilled person as a molecule including two or more covalently linked nucleosides. Such covalently bound nucleosides may also be referred to as nucleic acid molecules or oligomers. Oligonucleotides are commonly made in the laboratory by solid-phase chemical synthesis followed by purification. When referring to a sequence of the oligonucleotide, reference is made to the sequence or order of nucleobase moieties, or modifications thereof, of the covalently linked nucleotides or nucleosides. The oligonucleotide of the invention may be man-made, and is chemically synthesized, and is typically purified or isolated. Oligonucleotide is also intended to include (i) compounds that have one or more furanose moieties that are replaced by furanose derivatives or by any structure, cyclic or acyclic, that may be used as a point of covalent attachment for the base moiety, (ii) compounds that have one or more phosphodiester linkages that are either modified, as in the case of phosphoramidate or phosphorothioate linkages, or completely replaced by a suitable linking moiety as in the case of formacetal or riboacetal linkages, and/or (iii) compounds that have one or more linked furanose-phosphodiester linkage moieties replaced by any structure, cyclic or acyclic, that may be used as a point of covalent attachment for the base moiety. The oligonucleotide of the invention may include one or more alternative nucleosides or nucleotides (e.g., including those described herein). It is also understood that oligonucleotide includes compositions lacking a sugar moiety or nucleobase but is still capable of forming a pairing with or hybridizing to a target sequence.

"Oligonucleotide" refers to a short polynucleotide (e.g., of 100 or fewer linked nucleosides).

The oligonucleotide may be of any length that permits deamination of an adenosine of a desired target RNA through an ADAR-mediated pathway, and may range from about 10-50 base pairs in length, e.g., about 15-50 base pairs in length or about 18-50 base pairs in length, for example, about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 base pairs in length, such as about 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

The term "gapmer" as used herein, refers to an oligonucleotide which includes a region of RNase H recruiting oligonucleotides (gap) which is flanked 5' and 3' by regions which include one or more affinity enhancing alternative nucleosides (wings or flanks). Various gapmer designs are described herein. Headmers and tailmers are oligonucleotides capable of recruiting RNase H where one of the wings is missing, i.e. only one of the ends of the oligonucleotide includes affinity enhancing alternative nucleosides. For headmers the 3' wing is missing (i.e. the 5' wing includes affinity enhancing alternative nucleosides) and for tailmers the 5' wing is missing (i.e. the 3' wing includes affinity enhancing alternative nucleosides). A "mixed wing gapmer" refers to a gapmer wherein the wing regions include at least one alternative nucleoside, such as at least one DNA nucleoside or at least one 2' substituted alternative nucleoside, such as, for example, 2'-O-alkyl-RNA, 2'-O-methyl-RNA, 2'-alkoxy-RNA, 2'-O-methoxyethyl-RNA (2'-O-MOE), 2'-amino-DNA, 2'-Fluoro-RNA, 2'-F-ANA nucleoside(s), or bicyclic nucleosides (e.g., locked nucleosides or cEt nucleosides). In some embodiments the mixed wing gapmer has one wing which includes alternative nucleosides (e.g. 5' or 3') and the other wing (3' or 5' respectfully) includes 2' substituted alternative nucleoside(s).

The term "linker" or "linking group" is a connection between two atoms that links one chemical group or segment of interest to another chemical group or segment of interest via one or more covalent bonds. Conjugate moieties can be attached to the oligonucleotide directly or through a linking moiety (e.g. linker or tether). Linkers serve to covalently connect a third region, e.g. a conjugate moiety to an oligonucleotide (e.g. the termini of region A or C). In some embodiments of the invention the conjugate or oligonucleotide conjugate of the invention may optionally, include a linker region which is positioned between the oligonucleotide and the conjugate moiety. In some embodiments, the linker between the conjugate and oligonucleotide is biocleavable. Phosphodiester containing bioscleavable linkers are described in more detail in WO 2014/076195 (herein incorporated by reference).

As used herein, the term "ADAR-recruiting domain" refers nucleotide sequences that may be covalently linked to the oligonucleotides of the instant invention and form stem-loop structures that act as recruitment and binding regions for the ADAR enzyme (e.g., an ADAR-recruiting domain). Oligonucleotides including such ADAR-recruiting domains may be referred to as 'axiomer AONs' or 'self-looping AONs.' The ADAR-recruiting domain portion may act to recruit an endogenous ADAR enzyme present in the cell. Such ADAR-recruiting domains do not require conjugated entities or presence of modified recombinant ADAR enzymes. Alternatively, the ADAR-recruiting portion may act to recruit a recombinant ADAR fusion protein that has been delivered to a cell or to a subject via an expression vector construct including a polynucleotide encoding an ADAR fusion protein. Such ADAR-fusion proteins may include the deaminase domain of ADAR1 or ADAR2 enzymes fused to another protein, e.g., to the MS2 bacteriophage coat protein. An ADAR-recruiting domain may be a nucleotide sequence based on a natural substrate (e.g., the GluR2 receptor pre-mRNA; such as a GluR2 ADAR-recruiting domain), a Z-DNA structure, or a domain known to recruit another protein which is part of an ADAR fusion protein, e.g., an MS2 ADAR-recruiting domain known to be recognized by the dsRNA binding regions of ADAR. A stem-loop structure of an ADAR-recruiting domain can be an intermolecular stem-loop structure, formed by two separate nucleic acid strands, or an intramolecular stem loop structure, formed within a single nucleic acid strand.

As used herein, the term "Z-DNA" refers to a left-handed conformation of the DNA double helix or RNA stem loop structures. Such DNA or dsRNA helices wind to the left in a zigzag pattern (as opposed to the right, like the more commonly found B-DNA form). Z-DNA is a known high-affinity ADAR binding substrate and has been shown to bind to human ADAR1 enzyme.

As used herein, and unless otherwise indicated, the term "complementary," when used to describe a first nucleotide or nucleoside sequence in relation to a second nucleotide or nucleoside sequence, refers to the ability of an oligonucleotide or polynucleotide including the first nucleotide or nucleoside sequence to hybridize and form a duplex structure under certain conditions with an oligonucleotide or polynucleotide including the second nucleotide sequence, as will be understood by the skilled person. Such conditions can, for example, be stringent conditions, where stringent conditions can include: 400 mM NaCl, 40 mM PIPES pH 6.4, 1 mM EDTA, 50° C., or 70° C., for 12-16 hours followed by washing (see, e.g., "Molecular Cloning: A Laboratory Manual, Sambrook, et al. (1989) Cold Spring Harbor Laboratory Press). Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides or nucleosides.

"Complementary" sequences, as used herein, can also include, or be formed entirely from, non-Watson-Crick base pairs and/or base pairs formed from non-natural and alternative nucleotides, in so far as the above requirements with respect to their ability to hybridize are fulfilled. Such non-Watson-Crick base pairs include, but are not limited to, G:U Wobble or Hoogstein base pairing. Complementary sequences between an oligonucleotide and a target sequence as described herein, include base-pairing of the oligonucleotide or polynucleotide including a first nucleotide sequence to an oligonucleotide or polynucleotide including a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally no more than 5, 4, 3 or 2 mismatched base pairs upon hybridization for a duplex up to 30 base pairs, while retaining the ability to hybridize under the conditions most relevant to their ultimate application, e.g., deamination of an adenosine. "Substantially complementary" can also refer to a polynucleotide that is substantially complementary to a contiguous portion of the mRNA of interest (e.g., an mRNA having a target adenosine). For example, a polynucleotide is complementary to at least a part of the mRNA of interest if the sequence is substantially complementary to a non-interrupted portion of the mRNA of interest.

As used herein, the term "region of complementarity" refers to the region on the oligonucleotide that is substantially complementary to all or a portion of a gene, primary transcript, a sequence (e.g., a target sequence; e.g., a target sequence having a target adenosine), or processed mRNA, so as to interfere with expression of the endogenous gene. Where the region of complementarity is not fully complementary to the target sequence, the mismatches can be in the internal or terminal regions of the molecule. Generally, the most tolerated mismatches are in the terminal regions, e.g., within 5, 4, 3, or 2 nucleotides of the 5'- and/or 3'-terminus of the oligonucleotide.

The phrase "contacting a cell with an oligonucleotide," such as an oligonucleotide, as used herein, includes contacting a cell by any possible means. Contacting a cell with an oligonucleotide includes contacting a cell in vitro with the oligonucleotide or contacting a cell in vivo with the oligonucleotide. The contacting may be done directly or indirectly. Thus, for example, the oligonucleotide may be put into physical contact with the cell by the individual performing the method, or alternatively, the oligonucleotide agent may be put into a situation that will permit or cause it to subsequently come into contact with the cell.

Contacting a cell in vitro may be done, for example, by incubating the cell with the oligonucleotide. Contacting a cell in vivo may be done, for example, by injecting the oligonucleotide into or near the tissue where the cell is located, or by injecting the oligonucleotide agent into another area, e.g., the bloodstream or the subcutaneous space, such that the agent will subsequently reach the tissue where the cell to be contacted is located. For example, the oligonucleotide may contain and/or be coupled to a ligand, e.g., GalNAc3, that directs the oligonucleotide to a site of interest, e.g., the liver. Combinations of in vitro and in vivo methods of contacting are also possible. For example, a cell may also be contacted in vitro with an oligonucleotide and subsequently transplanted into a subject.

In one embodiment, contacting a cell with an oligonucleotide includes "introducing" or "delivering the oligonucleotide into the cell" by facilitating or effecting uptake or absorption into the cell. Absorption or uptake of an oligonucleotide can occur through unaided diffusive or active cellular processes, or by auxiliary agents or devices. Introducing an oligonucleotide into a cell may be in vitro and/or in vivo. For example, for in vivo introduction, oligonucleotide s can be injected into a tissue site or administered systemically. In vitro introduction into a cell includes methods known in the art such as electroporation and lipofection. Further approaches are described herein below and/or are known in the art.

As used herein, "lipid nanoparticle" or "LNP" is a vesicle including a lipid layer encapsulating a pharmaceutically active molecule, such as a nucleic acid molecule, e.g., an oligonucleotide. LNP refers to a stable nucleic acid-lipid particle. LNPs typically contain a cationic, ionizable lipid, a non-cationic lipid, and a lipid that prevents aggregation of the particle (e.g., a PEG-lipid conjugate). LNPs are described in, for example, U.S. Pat. Nos. 6,858,225; 6,815, 432; 8,158,601; and 8,058,069, the entire contents of which are hereby incorporated herein by reference.

As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the oligonucleotide composition. The lipophilic material isolates the aqueous interior from an aqueous exterior, which typically does not include the oligonucleotide composition, although in some examples, it may. Liposomes also include "sterically stabilized" liposomes, a term which, as used herein, refers to liposomes including one or more specialized lipids that, when incorporated into liposomes, result in enhanced circulation lifetimes relative to liposomes lacking such specialized lipids.

"Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

"Complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other.

As used herein, the terms "effective amount," "therapeutically effective amount," and "a "sufficient amount" of an agent that results in a therapeutic effect (e.g., in a cell or a subject) described herein refer to a quantity sufficient to, when administered to the subject, including a human, effect beneficial or desired results, including clinical results, and, as such, an "effective amount" or synonym thereto depends on the context in which it is being applied. For example, in the context of treating a disorder, it is an amount of the agent that is sufficient to achieve a treatment response as compared to the response obtained without administration. The amount of a given agent will vary depending upon various factors, such as the given agent, the pharmaceutical formulation, the route of administration, the type of disease or disorder, the identity of the subject (e.g., age, sex, and/or weight) or host being treated, and the like, but can nevertheless be routinely determined by one of skill in the art. Also, as used herein, a "therapeutically effective amount" of an agent is an amount which results in a beneficial or desired result in a subject as compared to a control. As defined herein, a therapeutically effective amount of an agent may be readily determined by one of ordinary skill by routine methods known in the art. Dosage regimen may be adjusted to provide the optimum therapeutic response.

"Prophylactically effective amount," as used herein, is intended to include the amount of an oligonucleotide that, when administered to a subject having or predisposed to have a disorder, is sufficient to prevent or ameliorate the disease or one or more symptoms of the disease. Ameliorating the disease includes slowing the course of the disease or reducing the severity of later-developing disease. The "prophylactically effective amount" may vary depending on the oligonucleotide, how the agent is administered, the degree of risk of disease, and the history, age, weight, family history, genetic makeup, the types of preceding or concomitant treatments, if any, and other individual characteristics of the patient to be treated.

A "therapeutically-effective amount" or "prophylactically effective amount" also includes an amount (either administered in a single or in multiple doses) of an oligonucleotide that produces some desired local or systemic effect at a reasonable benefit/risk ratio applicable to any treatment. Oligonucleotides employed in the methods of the present invention may be administered in a sufficient amount to produce a reasonable benefit/risk ratio applicable to such treatment.

A prophylactically effective amount may also refer to, for example, an amount sufficient to, when administered to the subject, including a human, to delay the onset of one or more of the disorders described herein by at least 120 days, for example, at least 6 months, at least 12 months, at least 2 years, at least 3 years, at least 4 years, at least 5 years, at least 10 years or more, when compared with the predicted onset."

By "determining the level of a protein" is meant the detection of a protein, or an mRNA encoding the protein, by methods known in the art either directly or indirectly. "Directly determining" means performing a process (e.g., performing an assay or test on a sample or "analyzing a sample" as that term is defined herein) to obtain the physical entity or value. "Indirectly determining" refers to receiving the physical entity or value from another party or source (e.g., a third-party laboratory that directly acquired the physical entity or value). Methods to measure protein level generally include, but are not limited to, western blotting, immunoblotting, enzyme-linked immunosorbent assay (ELISA), radioimmunoassay (RIA), immunoprecipitation, immunofluorescence, surface plasmon resonance, chemiluminescence, fluorescent polarization, phosphorescence, immunohistochemical analysis, matrix-assisted laser desorption/ionization time-of-flight (MALDI-TOF) mass spectrometry, liquid chromatography (LC)-mass spectrometry, microcytometry, microscopy, fluorescence activated cell sorting (FACS), and flow cytometry, as well as assays based on a property of a protein including, but not limited to, enzymatic activity or interaction with other protein partners. Methods to measure mRNA levels are known in the art.

"Percent (%) sequence identity" with respect to a reference polynucleotide or polypeptide sequence is defined as the percentage of nucleic acids or amino acids in a candidate sequence that are identical to the nucleic acids or amino acids in the reference polynucleotide or polypeptide sequence, after aligning the sequences and introducing gaps, if necessary, to achieve the maximum percent sequence identity. Alignment for purposes of determining percent nucleic acid or amino acid sequence identity can be achieved in various ways that are within the capabilities of one of skill in the art, for example, using publicly available computer software such as BLAST, BLAST-2, or Megalign software. Those skilled in the art can determine appropriate parameters for aligning sequences, including any algorithms needed to achieve maximal alignment over the full length of the sequences being compared. For example, percent sequence identity values may be generated using the sequence comparison computer program BLAST. As an illustration, the percent sequence identity of a given nucleic acid or amino acid sequence, A, to, with, or against a given nucleic acid or amino acid sequence, B, (which can alternatively be phrased as a given nucleic acid or amino acid sequence, A that has a certain percent sequence identity to, with, or against a given nucleic acid or amino acid sequence, B) is calculated as follows:

100 multiplied by (the fraction X/Y)

where X is the number of nucleotides or amino acids scored as identical matches by a sequence alignment program (e.g., BLAST) in that program's alignment of A and B, and where Y is the total number of nucleic acids in B. It will be appreciated that where the length of nucleic acid or amino acid sequence A is not equal to the length of nucleic acid or amino acid sequence B, the percent sequence identity of A to B will not equal the percent sequence identity of B to A.

By "level" is meant a level or activity of a protein, or mRNA encoding the protein, as compared to a reference. The reference can be any useful reference, as defined herein. By a "decreased level" or an "increased level" of a protein is meant a decrease or increase in protein level, as compared to a reference (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, as compared to a reference; a decrease or an increase by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more). A level of a protein may be expressed in mass/vol (e.g., g/dL, mg/mL, µg/mL, ng/mL) or percentage relative to total protein or mRNA in a sample.

The term "pharmaceutical composition," as used herein, represents a composition containing a compound described herein formulated with a pharmaceutically acceptable excipient, and preferably manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); for intrathecal injection; for intracerebroventricular injections; for intraparenchymal injection; or in any other pharmaceutically acceptable formulation.

A "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

As used herein, the term "pharmaceutically acceptable salt" means any pharmaceutically acceptable salt of the compound of any of the compounds described herein. For example, pharmaceutically acceptable salts of any of the compounds described herein include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting a free base group with a suitable organic acid.

The compounds described herein may have ionizable groups so as to be capable of preparation as pharmaceutically acceptable salts. These salts may be acid addition salts involving inorganic or organic acids or the salts may, in the case of acidic forms of the compounds described herein, be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

By a "reference" is meant any useful reference used to compare protein or mRNA levels or activity. The reference can be any sample, standard, standard curve, or level that is used for comparison purposes. The reference can be a normal reference sample or a reference standard or level. A "reference sample" can be, for example, a control, e.g., a predetermined negative control value such as a "normal control" or a prior sample taken from the same subject; a sample from a normal healthy subject, such as a normal cell or normal tissue; a sample (e.g., a cell or tissue) from a subject not having a disease; a sample from a subject that is diagnosed with a disease, but not yet treated with a compound described herein; a sample from a subject that has been treated by a compound described herein; or a sample of a purified protein (e.g., any described herein) at a known normal concentration. By "reference standard or level" is meant a value or number derived from a reference sample. A "normal control value" is a pre-determined value indicative of non-disease state, e.g., a value expected in a healthy control subject. Typically, a normal control value is expressed as a range ("between X and Y"), a high threshold ("no higher than X"), or a low threshold ("no lower than X"). A subject having a measured value within the normal control value for a particular biomarker is typically referred to as "within normal limits" for that biomarker. A normal reference standard or level can be a value or number derived from a normal subject not having a disease or disorder; a subject that has been treated with a compound described herein. In preferred embodiments, the reference sample, standard, or level is matched to the sample subject sample by at least one of the following criteria: age, weight, sex, disease stage, and overall health. A standard curve of levels of a purified protein, e.g., any described herein, within the normal reference range can also be used as a reference.

As used herein, the term "subject" refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the terms "treat," "treated," or "treating" mean both therapeutic treatment and prophylactic or preventative measures wherein the object is to prevent or slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment.

As used herein, the terms "variant" and "derivative" are used interchangeably and refer to naturally-occurring, synthetic, and semi-synthetic analogues of a compound, peptide, protein, or other substance described herein. A variant or derivative of a compound, peptide, protein, or other substance described herein may retain or improve upon the biological activity of the original material.

The details of one or more embodiments of the invention are set forth in the description below. Other features, objects, and advantages of the invention will be apparent from the description and from the claims.

DETAILED DESCRIPTION

The present inventors have found modified oligonucleotides may be utilized to deaminate target adenosines in mRNAs. Accordingly, the invention features useful compositions and methods to deaminate target adenosines on mRNA, e.g., an adenosine which may be deaminated to produce a therapeutic result, e.g., in a subject in need thereof.

I. Disorders

The invention also provides an oligonucleotide of the invention for use in a method for making a change in a target RNA sequence in a mammalian, preferably human cell, as described herein. Similarly, the invention provides the use of an oligonucleotide construct of the invention in the manufacture of a medicament for making a change in a target RNA sequence in a mammalian, preferably human cell, as described herein.

The invention also relates to a method for the deamination of at least one specific target adenosine present in a target RNA sequence in a cell, said method including the steps of: providing said cell with an oligonucleotide described herein; allowing uptake by the cell of the oligonucleotide; allowing annealing of the oligonucleotide to the target RNA sequence; allowing a mammalian ADAR enzyme including a natural dsRNA binding domain as found in the wild type enzyme to deaminate said target adenosine in the target RNA sequence to an inosine; and optionally identifying the presence of the inosine in the RNA sequence.

Hence, the invention also relates to oligonucleotides and methods wherein two adenosines that are next to each other are co-deaminated by an RNA editing enzyme such as ADAR. In this particular case, the UAA stop codon is converted into a UII Trp-encoding codon. Other examples of modifications resulting from deamination of target adenosines within a target codon are provided in Tables 1 and 2 below.

TABLE 1

| Target Codon | Amino Acid Encoded by Target Codon | Modified Codon | Amino Acid Encoded by Modified Codon |
|---|---|---|---|
| AAA | Lys | IAA | Glu |
|  |  | AIA | Arg |
|  |  | IIA | Gly |
|  |  | AII | Arg |
|  |  | IAI | Glu |
|  |  | III | Gly |
| AAC | Asn | IAC | Asp |
|  |  | AIC | Ser |
|  |  | IIC | Gly |
| AAG | Lys | IAG | Glu |
|  |  | AIG | Arg |
|  |  | IIG | Gly |
| AAU | Arg | IAU | Asp |
|  |  | AIU | Ser |
|  |  | IIU | Gly |
| ACA | Thr | ICA | Ala |
|  |  | ICI | Ala |
| ACC | Thr | ICC | Ala |
| ACG | Thr | ICG | Ala |
| ACU | Thr | ICU | Ala |
| AGA | Arg | IGA | Gly |
|  |  | IGI | Gly |
| AGC | Ser | IGC | Gly |
| AGG | Arg | IGG | Gly |
| AGU | Ser | IGU | Gly |
| AUA | Ile | IUA | Asp |
|  |  | AUI | Met |
|  |  | IUI | Val |
| AUC | Ile | IUC | Val |
| AUG | Met | IUG | Val |
| AUU | Ile | IUU | Val |
| CAA | Gln | CIA | Arg |
|  |  | CII | Arg |
| CAC | His | CIC | Arg |
| CAG | Gln | CIG | Arg |
| CAU | His | CIU | Arg |
| GAA | Glu | GIA | Gly |
|  |  | GII | Gly |
| GAC | Asp | GIC | Gly |
| GAG | Glu | GIG | Gly |
| GAU | Asp | GIU | Gly |
| UAA | Stop | UII | Trp |
| UGA | Stop | UGI | Trp |
| UAC | Tyr | UIC | Cys |
| UAG | Stop | UIG | Trp |
| UAU | Tyr | UIU | Cys |

TABLE 2

Target Codon Base Composition and Resulting Modified Codon

| Target Codon | Modified Codon |
|---|---|
| AAA | AIA |
| AAC | AIC |
| AAG | AIG |
| AAU | AIU |
| CAA | CIA |
| CAC | CIC |
| CAG | CIG |

TABLE 2-continued

Target Codon Base Composition and Resulting Modified Codon

| Target Codon | Modified Codon |
|---|---|
| CAU | CIU |
| GAA | GIA |
| GAC | GIC |
| GAG | GIG |
| GAU | GIU |
| UAA | UIA |
| UAC | UIC |
| UAG | UIG |
| UAU | UIU |

Because the deamination of the adenosine to an inosine may result in a protein that is no longer suffering from the mutated A at the target position, the identification of the deamination into inosine may be a functional read-out, for instance an assessment on whether a functional protein is present, or even the assessment that a disease that is caused by the presence of the adenosine is (partly) reversed. The functional assessment for each of the diseases mentioned herein will generally be according to methods known to the skilled person. When the presence of a target adenosine causes aberrant splicing, the read-out may be the assessment of whether the aberrant splicing is still taking place, or not, or less. On the other hand, when the deamination of a target adenosine is wanted to introduce a splice site, then similar approaches can be used to check whether the required type of splicing is indeed taking place. A very suitable manner to identify the presence of an inosine after deamination of the target adenosine is of course RT-PCR and sequencing, using methods that are well-known to the person skilled in the art.

In general, mutations in any target RNA that can be reversed using oligonucleotide constructs according to the invention are G-to-A mutations, and oligonucleotide constructs can be designed accordingly. Mutations that may be targeted using oligonucleotide constructs according to the invention also include C to A, U to A (T to A on the DNA level) in the case of recruiting adenosine deaminases. Although RNA editing in the latter circumstances may not necessarily revert the mutation to wild-type, the edited nucleotide may give rise to an improvement over the original mutation. For example, a mutation that causes an in frame stop codon—giving rise to a truncated protein, upon translation—may be changed into a codon coding for an amino acid that may not be the original amino acid in that position, but that gives rise to a (full length) protein with at least some functionality, at least more functionality than the truncated protein.

The invention is particularly suitable for treating genetic diseases, such as cystic fibrosis, albinism, alpha-1-antitrypsin (A1AT) deficiency, Alzheimer disease, amyotrophic lateral sclerosis, asthma, 11-thalassemia, Cadasil syndrome, Charcot-Marie-Tooth disease, chronic obstructive pulmonary disease (COPD), distal spinal muscular atrophy (DSMA), Duchenne/Becker muscular dystrophy, dystrophic epidermolysis bullosa, epidermylosis bullosa, Fabry disease, Factor V Leiden associated disorders, familial adenomatous, polyposis, galactosemia, Gaucher's disease, glucose-6-phosphate dehydrogenase deficiency, haemophilia, hereditary hematochromatosis, Hunter syndrome, Huntington's disease, Hurler syndrome, inflammatory bowel disease (IBD), inherited polyagglutination syndrome, Leber congenital amaurosis, Lesch-Nyhan syndrome, Lynch syndrome, Marfan syndrome, mucopolysaccharidosis, muscular dystrophy, myotonic dystrophy types I and II, neurofibromatosis, Niemann-Pick disease type A, B and C, NY-ESO-1 related cancer, Parkinson's disease, Peutz-Jeghers syndrome, phenylketonuria, Pompe's disease, primary ciliary disease, prothrombin mutation related disorders (e.g., prothrombin G20210A mutation), pulmonary hypertension, retinitis pigmentosa, Sandhoff disease, severe combined immune deficiency syndrome (SCID), sickle cell anemia, spinal muscular atrophy, Stargardt's disease, Tay-Sachs disease, Usher syndrome, X-linked immunodeficiency, Sturge-Weber syndrome, Rett syndrome, and various forms of cancer (e.g. BRCA1 and 2 linked breast cancer and ovarian cancer).

Oligonucleotides of the invention may deaminate the adenosine mutation resulting in an increase in protein activity.

In certain embodiments, treatment is performed on a subject who has been diagnosed with a mutation in a gene, but does not yet have disease symptoms (e.g., an infant such as a subject that is 1 month to 12 months old or subject under the age of 2). In other embodiments, treatment is performed on an individual who has at least one symptom.

Treatment may be performed in a subject of any age, starting from infancy to adulthood. Subjects may begin treatment, for example, at birth, six months, or 1, 2, 3, 4, 5, 6, 7, 8, 9, 10, 11, 12, 13, 15, or 18 years of age.

In certain embodiments, the oligonucleotide increases (e.g., an increase by 100%, 150%, 200%, 300%, 400%, 500%, 600%, 700%, 800%, 900%, 1000% or more, or an increase by more than 1.2-fold, 1.4-fold, 1.5-fold, 1.8-fold, 2.0-fold, 3.0-fold, 3.5-fold, 4.5-fold, 5.0-fold, 10-fold, 15-fold, 20-fold, 30-fold, 40-fold, 50-fold, 100-fold, 1000-fold, or more) protein activity in vitro and/or in vivo.

In some embodiments, the oligonucleotide increases (e.g., an increase by 100%, 150%, 200%, 300%, 400%, 500%, 600%, 700%, 800%, 900%, 1000% or more, or an increase by more than 1.2-fold, 1.4-fold, 1.5-fold, 1.8-fold, 2.0-fold, 3.0-fold, 3.5-fold, 4.5-fold, 5.0-fold, 10-fold, 15-fold, 20-fold, 30-fold, 40-fold, 50-fold, 100-fold, 1000-fold, or more) protein activity in the brain.

II. Oligonucleotide Agents

The oligonucleotides of the invention are complementary to target mRNA with the exception of at least one mismatch capable of recruiting ADAR enzymes to deaminate selected adenosines on the target mRNA. In some embodiments, only one adenosine is deaminated. In some embodiments, 1, 2, or 3 adenosines is deaminated. The oligonucleotide includes a mismatch opposite the target adenosine, e.g., at $X^2$. The oligonucleotides of the invention may further include modifications (e.g., alternative nucleotides) to increase stability and/or increase deamination efficiency.

A. Alternative Oligonucleotides

In one embodiment, one or more of the nucleotides of the oligonucleotide of the invention, is naturally-occurring, and does not include, e.g., chemical modifications and/or conjugations known in the art and described herein. In another embodiment, one or more of the nucleotides of an oligonucleotide of the invention, is chemically modified to enhance stability or other beneficial characteristics (e.g., alternative nucleotides). Without being bound by theory, it is believed that certain modification can increase nuclease resistance and/or serum stability or decrease immunogenicity. For example, polynucleotides of the invention may contain nucleotides found to occur naturally in DNA or RNA (e.g., adenine, thymidine, guanosine, cytidine, uridine, or inosine) or may contain nucleotides which have one or more chemical modifications to one or more components of the nucleotide (e.g., the nucleobase, sugar, or phospho-linker moiety). Oligonucleotides of the invention may be linked to one another through naturally-occurring phosphodiester bonds or may be modified to be covalently linked through phosphorothioate, 3'-methylenephosphonate, 5'-methylenephosphonate, 3'-phosphoamidate, 2'-5' phosphodiester, guanidinium, S-methylthiourea, or peptide bonds.

In some embodiments, one or more of the nucleotides of the oligonucleotide of the invention has the structure of any one of Formula I-VI:

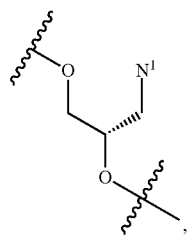
Formula I

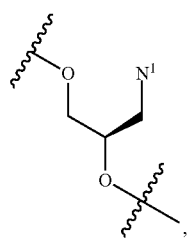
Formula II

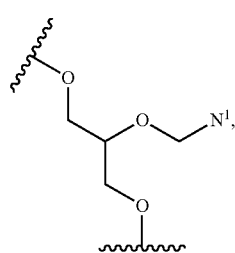
Formula III

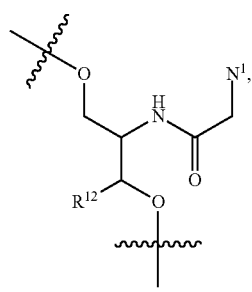
Formula IV

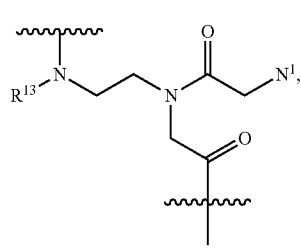
Formula V

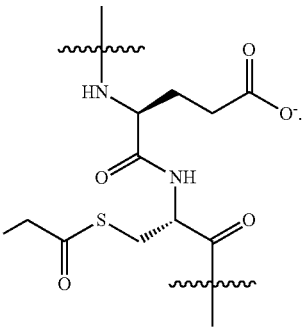
Formula VI

In some embodiments, one or more of the nucleotides of the oligonucleotide of the invention has the structure of any one of Formula I.

In some embodiments, one or more of the nucleotides of the oligonucleotide of the invention has the structure of any one of Formula II.

In some embodiments, one or more of the nucleotides of the oligonucleotide of the invention has the structure of any one of Formula III.

In some embodiments, one or more of the nucleotides of the oligonucleotide of the invention has the structure of any one of Formula IV, e.g., has the structure:

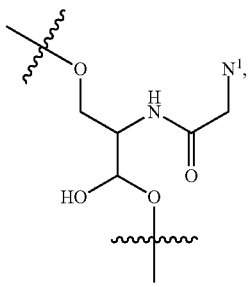

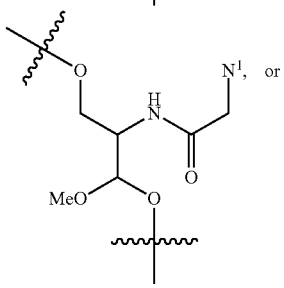
or

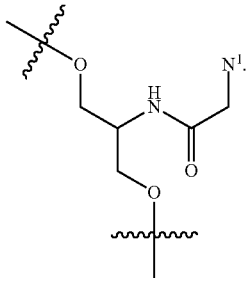

In some embodiments, one or more of the nucleotides of the oligonucleotide of the invention has the structure of any one of Formula V, e.g., has the structure:

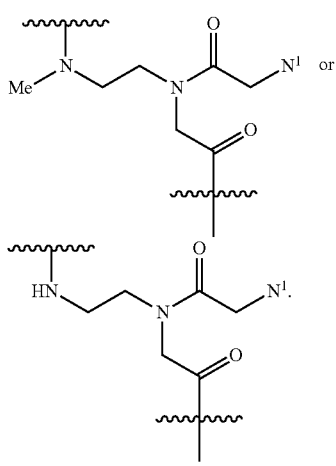

In some embodiments, one or more of the nucleotides of the oligonucleotide of the invention has the structure of any one of Formula VI, e.g., has the structure:

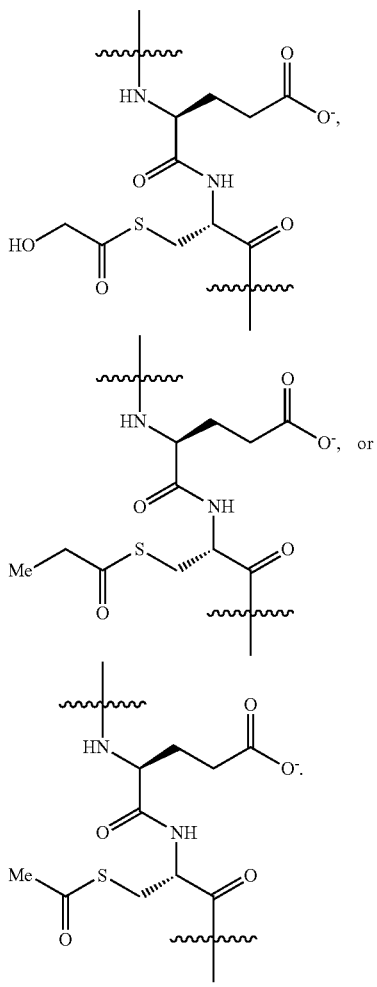

In certain embodiments of the invention, substantially all of the nucleotides of an oligonucleotide of the invention are alternative nucleotides. In other embodiments of the invention, all of the nucleotides of an oligonucleotide of the invention are alternative nucleotides. Oligonucleotides of the invention in which "substantially all of the nucleotides are alternative nucleotides" are largely but not wholly modified and can include no more than 5, 4, 3, 2, or 1 naturally-occurring nucleotides. In still other embodiments of the invention, oligonucleotides of the invention can include no more than 5, 4, 3, 2, or 1 alternative nucleotides.

In some embodiments of the invention, the oligonucleotides of the instant invention include the structure:

$[A_m]$-$X^1$—$X^2$—$X^3$—$[B_n]$ wherein each of A and B is a nucleotide; m and n are each, independently, an integer from 5 to 40; at least one of $X^1$, $X^2$, and $X^3$ has the structure of Formula I, Formula II, Formula III, or Formula IV, wherein $N^1$ is a nucleobase and each of $X^1$, $X^2$, and $X^3$ that does not have the structure of Formula I, Formula II, Formula III, or Formula IV is a ribonucleotide; $[A_m]$ and $[B_n]$ each include at least five terminal 2'-O-methyl-nucleotides and at least four terminal phosphorothioate linkages; and at least 20% of the nucleotides of $[A_m]$ and $[B_n]$ combined are 2'-O-methyl-nucleotides. In some embodiments, $X^1$ includes an adenine nucleobase, $X^2$ includes a cytosine, 5-methylcytosine, uracil, or thymine nucleobase or does not include a nucleobase, and $X^3$ includes an adenine nucleobase; $X^1$ includes an adenine nucleobase, $X^2$ includes a cytosine, 5-methylcytosine, uracil, or thymine nucleobase or does not include a nucleobase, and $X^3$ includes a guanine or hypoxanthine nucleobase; $X^1$ includes an adenine nucleobase, $X^2$ includes a cytosine, 5-methylcytosine, uracil, or thymine nucleobase or does not include a nucleobase, and $X^3$ includes a uracil or thymine nucleobase; $X^1$ includes an adenine nucleobase, $X^2$ includes a cytosine, 5-methylcytosine, uracil, or thymine nucleobase or does not include a nucleobase, and $X^3$ includes a cytosine or 5-methylcytosine nucleobase; $X^1$ includes a guanine or hypoxanthine nucleobase, $X^2$ includes a cytosine, 5-methylcytosine, uracil, or thymine nucleobase or does not include a nucleobase, and $X^3$ includes an adenine nucleobase; $X^1$ includes a guanine or hypoxanthine nucleobase, $X^2$ includes a cytosine, 5-methylcytosine, uracil, or thymine nucleobase or does not include a nucleobase, and $X^3$ includes a guanine or hypoxanthine nucleobase; $X^1$ includes a guanine or hypoxanthine nucleobase, $X^2$ includes a cytosine, 5-methylcytosine, uracil, or thymine nucleobase or does not include a nucleobase, and $X^3$ includes a uracil or thymine nucleobase; $X^1$ includes a guanine or hypoxanthine nucleobase, $X^2$ includes a cytosine, 5-methylcytosine, uracil, or thymine nucleobase or does not include a nucleobase, and $X^3$ includes a cytosine or 5-methylcytosine nucleobase; $X^1$ includes a uracil or thymine nucleobase, $X^2$ includes a cytosine, 5-methylcytosine, uracil, or thymine nucleobase or does not include a nucleobase, and $X^3$ includes an adenine nucleobase; $X^1$ includes a uracil or thymine nucleobase, $X^2$ includes a cytosine, 5-methylcytosine, uracil, or thymine nucleobase or does not include a nucleobase, and $X^3$ includes a guanine or hypoxanthine nucleobase; $X^1$ includes a uracil or thymine nucleobase, $X^2$ includes a cytosine, 5-methylcytosine, uracil, or thymine nucleobase or does not include a nucleobase, and $X^3$ includes a uracil or thymine nucleobase; $X^1$ includes a uracil or thymine nucleobase, $X^2$ includes a cytosine, 5-methylcytosine, uracil, or thymine nucleobase or does not include a nucleobase, and $X^3$ includes a cytosine or 5-methylcytosine nucleobase; $X^1$ includes a cytosine or 5-methylcytosine nucleobase, $X^2$ includes a cytosine, 5-methylcytosine, uracil, or thymine nucleobase or does not include a nucleobase, and $X^3$ includes an adenine nucleobase; $X^1$ includes a cytosine or 5-methylcytosine nucleobase, $X^2$ includes a cytosine, 5-methylcytosine, uracil, or thymine nucleobase or does not include a nucleobase, and $X^3$ includes a guanine or hypoxanthine nucleobase; $X^1$ includes a cytosine or 5-methylcytosine nucleobase, $X^2$ includes a cytosine, 5-methylcytosine, uracil, or thymine nucleobase or does not include a nucleobase, and $X^3$ includes a uracil or thymine nucleobase; or $X^1$ includes a cytosine or 5-methylcytosine nucleobase, $X^2$ includes a cytosine, 5-methylcytosine, uracil, or thymine nucleobase or does not include a nucleobase, and $X^3$ includes a cytosine or 5-methylcytosine nucleobase.

Exemplary oligonucleotides of the instant invention are shown in Table 3 below. In Table 3, A, C, G and U are ribonucleosides; mA, mC, mG and mU are 2'-O-methyl ribonucleosides; sgC represents (S)-(−)-GNA-C; rgC represents (R)-(+)-GNA-C; sC represents SNA-cytidine (SNA-C); fxC represents FNA-cytidine (FNA-C); and asterisks indicate phosphorothioate linkages (the remaining linkages are phosphodiester linkages).

TABLE 3

Exemplary Oligonucleotides of the Invention

| Sequence | SEQ ID NO. |
|---|---|
| 5'-mC*mA*mU*mA*mAUUCUUGUGUCUACUGUACAGAAUACUGCCGCCAGCUGGAUmU*mU*mC*mC*mC-3' | SEQ ID NO. 51 |
| 5'-mC*mA*mU*mA*mAUUCUUGUGUCUACUGUACAGAAUACUGCCGSgCCAGCUGGAUmU*mU*mC*mC*mC-3' | SEQ ID NO. 52 |
| 5'-mC*mA*mU*mA*mAUUCUUGUGUCUACUGUACAGAAUACUGCCGCSgCAGCUGGAUmU*mU*mC*mC*mC-3' | SEQ ID NO. 53 |
| 5'-mC*mA*mU*mA*mAUUCUUGUGUCUACUGUACAGAAUACUGCCGSgCSgCAGCUGGAUmU*mU*mC*mC*mC-3' | SEQ ID NO. 54 |
| 5'-mC*mA*mU*mA*mAUUCUUGUGUCUACUGUACAGAAUACUGCCGrgCCAGCUGGAUmU*mU*mC*mC*mC-3' | SEQ ID NO. 55 |
| 5'-mC*mA*mU*mA*mAUUCUUGUGUCUACUGUACAGAAUACUGCCGCrgCAGCUGGAUmU*mU*mC*mC*mC-3' | SEQ ID NO. 56 |
| 5'-mC*mA*mU*mA*mAUUCUUGUGUCUACUGUACAGAAUACUGCCGsCCAGCUGGAUmU*mU*mC*mC*mC-3' | SEQ ID NO. 57 |
| 5'-mC*mA*mU*mA*mAUUCUUGUGUCUACUGUACAGAAUACUGCCGCSCAGCUGGAUmU*mU*mC*mC*mC-3' | SEQ ID NO. 58 |
| 5'-mC*mA*mU*mA*mAUUCUUGUGUCUACUGUACAGAAUACUGCCGfxCCAGCUGGAUmU*mU*mC*mC*mC-3' | SEQ ID NO. 59 |
| 5'-mC*mA*mU*mA*mAUUCUUGUGUCUACUGUACAGAAUACUGCCGCfxCAGCUGGAUmU*mU*mC*mC*mC-3' | SEQ ID NO. 60 |
| 5'-mC*mA*mU*mA*mAUUCmUmUGUGmUmCUACmUmGUACmAmGAAUmAmCUGCmCmGCCAmGmCUGmGmAUmU*mU*mC*mC*mC-3' | SEQ ID NO. 61 |
| 5'-mC*mA*mU*mA*mAUUCmUmUGUGmUmCUACmUmGUACmAmGAAUmAmCUGCmCmGsgCCAmGmCUGmGmAUmU*mU*mC*mC*mC-3' | SEQ ID NO. 62 |
| 5'-mC*mA*mU*mA*mAUUCmUmUGUGmUmCUACmUmGUACmAmGAAUmAmCUGCmCmGCsgCAmGmCUGmGmAUmU*mU*mC*mC*mC-3' | SEQ ID NO. 63 |
| 5'-mC*mA*mU*mA*mAUUCmUmUGUGmUmCUACnnUmGUACmAmGAAUmAmCUGCmCmGsgCsgCAmGmCUGmGmAUmU*mU*mC*mC*mC-3' | SEQ ID NO. 64 |
| 5'-mC*mA*mU*mA*mAUUCmUmUGUGmUmCUACmUmGUACmAmGAAUmAmCUGCmCmGrgCCAmGmCUGmGmAUmU*mU*mC*mC*mC-3' | SEQ ID NO. 65 |
| 5'-mC*mA*mU*mA*mAUUCmUmUGUGmUmCUACmUmGUACmAmGAAUmAmCUGCmCmGCrgCAmGmCUGmGmAUmU*mU*mC*mC*mC-3' | SEQ ID NO. 66 |
| 5'-mC*mA*mU*mA*mAUUCmUmUGUGmUmCUACmUmGUACmAmGAAUmAmCUGCmCmGsCCAmGmCUGmGmAUmU*mU*mC*mC*mC-3' | SEQ ID NO. 67 |
| 5'-mC*mA*mU*mA*mAUUCmUmUGUGmUmCUACmUmGUACmAmGAAUmAmCUGCmCmGCsCAmGmCUGmGmAUmU*mU*mC*mC*mC-3' | SEQ ID NO. 68 |
| 5'-mC*mA*mU*mA*mAUUCmUmUGUGmUmCUACmUmGUACmAmGAAUmAmCUGCmCmGfxCCAmGmCUGmGmAUmU*mU*mC*mC*mC-3' | SEQ ID NO. 69 |
| 5'-mC*mA*mU*mA*mAUUCmUmUGUGmUmCUACmUmGUACmAmGAAUmAmCUGCmCmGCfxCAmGmCUGmGmAUmU*mU*mC*mC*mC-3' | SEQ ID NO. 70 |

In some embodiments, the oligonucleotides of the instant invention include a stem-loop structure that acts as a recruitment domain for the ADAR enzyme (e.g., an ADAR-recruiting domain). Such oligonucleotides may be referred to as 'axiomer AONs' or 'self-looping AONs.' The recruitment portion acts in recruiting a natural ADAR enzyme present in the cell to the dsRNA formed by hybridization of the target sequence with the targeting portion. The recruitment portion may be a stem-loop structure mimicking either a natural substrate (e.g. the glutamate ionotropic receptor AMPA type subunit 2 (GluR2) receptor; such as a GluR2 ADAR-recruiting domain) or a Z-DNA structure known to be recognized by the dsRNA binding regions of ADAR enzymes (e.g., a Z-DNA ADAR-recruiting domain). As GluR2 and Z-DNA ADAR-recruiting domains are high affinity binding partners to ADAR, there is no need for conjugated entities or presence of modified recombinant ADAR enzymes. A stem-loop structure can be an intromolecular stem-loop structure, formed by two separate nucleic acid strands, or an intramolecular stem loop structure, formed within a single nucleic acid strand. The stem-loop structure of the recruitment portion may be a step loop structure described in WO 2016/097212, US 2018/0208924, Merkle et al. Nature Biotechnology, 37: 133-8 (2019), Katrekar et al. Nature Methods, 16(3): 239-42 (2019), Fukuda et al. Scientific Reports, 7: 41478 (2017), the stem-loop structures of the ADAR recruitment portion of which are herein incorporated by reference. In some embodiments, the oligonucleotides include one or more ADAR-recruiting domains (e.g., 1 or 2 ADAR-recruiting domains).

In some embodiments, the oligonucleotides of the invention include those having a structure of any one of Formulas VII, VIII, X, or XI. In one embodiment, the oligonucleotides of the invention include those including an ADAR-recruiting domain having a structure of Formula XXV:

C-L$_1$-D,  Formula XXV, wherein C is a single-stranded oligonucleotide of about 10-50 linked nucleosides in length (e.g., about 10, 15, 20, 25, 30, 35, 40, 45, 46, 47, 48, 49, or 50 linked nucleosides in length), L$_1$ is a loop region, and D is a single-stranded oligonucleotide of about 10-50 linked nucleosides in length (e.g., about 10, 15, 20, 25, 30, 35, 40, 45, 46, 47, 48, 49, or 50 linked nucleosides in length).

In some embodiments, C includes a region that is complementary to D such that the two strands hybridize and form a duplex under suitable conditions. Generally, the duplex structure is between 5 and 50 linked nucleosides in length, e.g., between, 5-49, 5-45, 5-40, 5-35, 5-30, 5-25, 5-20, 5-15, 5-10, 5-6, 8-50, 8-45, 8-40, 8-35, 8-30, 8-25, 8-20, 8-15, 8-10, 15-50, 15-45, 15-40, 15-35, 15-30, 15-25, 15-20, 15-16, 20-50, 20-45, 20-40, 20-35, 20-30, 20-25, 25-50, 25-45, 25-40, 25-35, or 25-30 linked nucleosides in length. Ranges and lengths intermediate to the above-recited ranges and lengths are also contemplated to be part of the invention. In some embodiments, C is complementary to at least 5 contiguous nucleobases (e.g., 5, 10, 15, 20, 25, 30, or more contiguous nucleobases) of D, and the oligonucleotide forms a duplex structure of between 10-50 linked nucleosides in length (e.g., at least 10, 15, 20, 25, 30, 35, 40, 45, 46, 47, 48, 49, or 50 linked nucleosides in length).

In some embodiments, the duplex structure includes at least one mismatch between nucleotides of C and nucleotides of D (e.g., at least 1, 2, 3, 4, or 5 mismatches). In some embodiments, the mismatch is a paired A to C mismatch. In some embodiments, the A nucleoside of the A to C mismatch is on the C strand and the C nucleoside of the A to C mismatch is on the D strand. In some embodiments, the A nucleoside of the A to C mismatch is on the D strand and the C nucleoside of the A to C mismatch is on the C strand. In other embodiments, the mismatch is a paired G-to-G mismatch. In still yet other embodiments, the mismatch is a paired C to A mismatch. In some embodiments, the C nucleoside of the C to A mismatch is on the C strand and the A nucleoside of the C to A mismatch is on the D strand. In some embodiments, the C nucleoside of the C to A mismatch is on the D strand and the A nucleoside of the C to A mismatch is on the C strand. In some embodiments, the mismatch is a paired I to G mismatch. In some embodiments, the I nucleoside of the I to G mismatch is on the C strand and the G nucleoside of the I to G mismatch is on the D strand. In some embodiments, the I nucleoside of the I to G mismatch is on the D strand and the G nucleoside of the I to G mismatch is on the C strand. In some embodiments, the mismatch is a paired G to I mismatch. In some embodiments, the G nucleoside of the G to I mismatch is on the C strand and the I nucleoside of the G to I mismatch is on the D strand. In some embodiments, the G nucleoside of the G to I mismatch is on the D strand and the I nucleoside of the G to I mismatch is on the C strand. In some embodiments, the mismatch includes a nucleoside having an alternative nucleobase. In some embodiments, the alternative nucleobase has the structure:

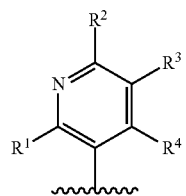

wherein R$^1$ is hydrogen, trifluoromethyl, optionally substituted amino, hydroxyl, or optionally substituted C$_1$-C$_6$ alkoxy;

R$^2$ is hydrogen, optionally substituted amino, or optionally substituted C$_1$-C$_6$ alkyl; and R$^3$ and R$^4$ are, independently, hydrogen, halogen, or optionally substituted C$_1$-C$_6$ alkyl, or a salt thereof. In some embodiments, R$^1$ is a hydrogen bond donor group (e.g., a hydroxyl group, an amino group). In some embodiments, R$^1$ is a hydrogen bond accepting group (e.g., an alkoxy group).

In some embodiments, the duplex structure includes two mismatches. In some embodiments, the mismatches are at least three linked nucleosides apart. For example, when mismatches are "separated by 3 nucleotides," the oligonucleotide includes the structure M$_1$-N$_1$—N$_2$—N$_3$-M$_2$, where M$_1$ is the first mismatch, N$_1$, N$_2$, and N$_3$ are paired nucleobases, and M$_2$ is the second mismatch. In some embodiments M$_1$ is a paired A to C mismatch and M$_2$ is a paired G-to-G mismatch.

In some embodiments, the loop region, L$_1$, includes linked nucleosides. In some embodiments, L$_1$ includes at least one alternative nucleobase, at least one alternative internucleoside linkage, and/or at least one alternative sugar moiety.

In other embodiments, the loop region has the structure of Formula IX:

F$^1$-(G$^1$)$_j$-(H$^1$)$_k$-(G$^2$)$_m$-(I)-(G$^3$)$_n$-(H$^2$)$_p$-(G$^4$)$_q$-F$^2$   Formula IX, wherein F$^1$ is a bond between the loop region and C; F$^2$ is a bond between D and a nucleotide or between D and, optionally, a linker; G$^1$, G$^2$, G$^3$, and G$^4$ each, independently, is selected from optionally substituted C$_1$-C$_2$ alkyl, optionally substituted C$_1$-C$_3$ heteroalkyl, O, S, and NR$^N$; R$^N$ is hydrogen, optionally substituted C$_{1-4}$ alkyl, optionally substituted C$_{2-4}$ alkenyl, optionally substituted C$_{2-4}$ alkynyl, optionally substituted C$_{2-6}$ heterocyclyl, optionally substituted C$_{6-12}$ aryl, or optionally substituted C$_{1-7}$ heteroalkyl; C$^1$ and C$^2$ are each, independently, selected from carbonyl, thiocarbonyl, sulphonyl, or phosphoryl; j, k, m, n, p, and q are each, independently, 0 or 1; and I is optionally substituted C$_{1-10}$ alkyl, optionally substituted C$_{2-10}$ alkenyl, optionally substituted C$_{2-10}$ alkynyl, optionally substituted C$_{2-6}$ heterocyclyl, optionally substituted C$_{6-12}$ aryl, optionally substituted $C_2$-$C_{10}$ polyethylene glycol, or optionally substituted $C_{1-10}$ heteroalkyl, or a chemical bond linking $F^1$-$(G^1)_j$-$(H^1)_k$-$(G^2)_m$-(I)-$(G^3)_n$-$(H^2)_p$-$(G^4)_q$-$F^2$. In some embodiments, the linker is optional In some embodiments, the loop region, $L_1$ includes a carbohydrate-containing linking moiety.

In one embodiment, one or more of the nucleotides of the oligonucleotides of the invention, is naturally-occurring, and does not include, e.g., chemical modifications and/or conjugations known in the art and described herein. In another embodiment, one or more of the nucleotides of an oligonucleotide of the invention is chemically modified to enhance stability or other beneficial characteristics (e.g., alternative nucleotides). Without being bound by theory, it is believed that certain modification can increase nuclease resistance and/or serum stability or decrease immunogenicity. For example, polynucleotides of the invention may contain nucleotides found to occur naturally in DNA or RNA (e.g., adenine, thymidine, guanosine, cytidine, uridine, or inosine) or may contain nucleotides which have one or more chemical modifications to one or more components of the nucleotide (e.g., the nucleobase, sugar, or phospho-linker moiety). Oligonucleotides of the invention may be linked to one another through naturally-occurring phosphodiester bonds or may be modified to be covalently linked through phosphorothioate, 3'-methylenephosphonate, 5'-methylenephosphonate, 3'-phosphoamidate, 2'-5' phosphodiester, guanidinium, S-methylthiourea, or peptide bonds.

In some embodiments, C includes at least one alternative nucleobase, at least one alternative internucleoside linkage, and/or at least one alternative sugar moiety. In other embodiments, D includes at least one alternative nucleobase, at least one alternative internucleoside linkage, and/or at least one alternative sugar moiety. In some embodiments, both C and D each include at least one alternative nucleobase, at least one alternative internucleoside linkage, and/or at least one alternative sugar moiety.

In certain embodiments of the invention, substantially all of the nucleotides of an oligonucleotide of the invention are alternative nucleotides. In other embodiments of the invention, all of the nucleotides of an oligonucleotide of the invention are alternative nucleotides. Oligonucleotides of the invention in which "substantially all of the nucleotides are alternative nucleotides" are largely but not wholly modified and can include no more than 5, 4, 3, 2, or 1 naturally-occurring nucleotides. In still other embodiments of the invention, an oligonucleotide of the invention can include no more than 5, 4, 3, 2, or 1 alternative nucleotides.

In one embodiment, the oligonucleotides of the invention include an ADAR-recruiting domain having the structure of Formula XXV, wherein C is a single-stranded oligonucleotide of 10-50 linked nucleosides in length, $L_1$ is a loop region, and D is a single-stranded oligonucleotide of 10-50 linked nucleosides in length. In some embodiments, C is complementary to at least 5 contiguous nucleobases of D, and the oligonucleotide includes a duplex structure formed by C and D of between 10-50 linked nucleosides in length. In some embodiments, the duplex structure includes at least one mismatch. In some embodiments, C or D includes at least one alternative nucleobase. In some embodiments, C and D each include at least one alternative nucleobase. In some embodiments, C and/or D, independently, further include at least one alternative internucleoside linkage and/or at least one alternative sugar moiety. In some embodiments, $L_1$ includes linked nucleotides. In other embodiments, $L_1$ consists of linked nucleosides. In some embodiments, $L_1$ includes at least one alternative nucleobase, at least one alternative internucleoside linkage, and/or at least one alternative sugar moiety.

In another embodiment, the oligonucleotides of the invention include an ADAR-recruiting domain having the structure of Formula XXV, wherein C is a single-stranded oligonucleotide of 10-50 linked nucleosides in length, $L_1$ is a loop region that does not consist of linked nucleosides, and D is a single-stranded oligonucleotide of 10-50 linked nucleosides in length. In some embodiments, C is complementary to at least 5 contiguous nucleobases of D, and the oligonucleotide includes a duplex structure formed by C and D of between 10-50 linked nucleosides in length. In some embodiments, the duplex structure includes at least one mismatch. In some embodiments, $L_1$ has the structure of Formula IX, as described herein. In some embodiments, $L_1$ includes a carbohydrate-containing linking moiety. In some embodiments, C and/or D, independently, include at least one alternative nucleobase, at least one alternative internucleoside linkage, and/or at least one alternative sugar moiety.

In another embodiment, the oligonucleotides of the invention include an ADAR-recruiting domain having the structure of Formula XXV, wherein C is a single-stranded oligonucleotide of 10-50 linked nucleosides in length, $L_1$ is a loop region including at least one alternative nucleobase or at least one alternative internucleoside linkage, and D is a single-stranded oligonucleotide of 10-50 linked nucleosides in length. In some embodiments, C is complementary to at least 5 contiguous nucleobases of D, and the oligonucleotide includes a duplex structure formed by C and D of between 10-50 linked nucleosides in length. In some embodiments, the duplex structure includes at least one mismatch. In some embodiments, $L_1$ includes at least one alternative nucleobase and at least one alternative internucleoside linkage.

In another embodiment, the oligonucleotides of the invention includes an ADAR-recruiting domain having the structure of Formula XXV, wherein C is a single-stranded oligonucleotide of 10-50 linked nucleosides in length, $L_1$ is a loop region including, at least one alternative sugar moiety that is not a 2' methyl sugar moiety (e.g., the alternative sugar moiety is selected from the group consisting of a 2'-O—$C_1$-$C_6$ alkyl-sugar moiety, a 2'-amino-sugar moiety, a 2'-fluoro-sugar moiety, a 2'-O-MOE sugar moiety, an LNA sugar moiety, an arabino nucleic acid (ANA) sugar moiety, a 2'-fluoro-ANA sugar moiety, a deoxyribose sugar moiety, and a bicyclic nucleic acid), and D is a single-stranded oligonucleotide of 10-50 linked nucleosides in length. In some embodiments, C is complementary to at least 5 contiguous nucleobases of D, and the oligonucleotide includes a duplex structure formed by C and D of between 10-50 linked nucleosides in length. In some embodiments, the duplex structure includes at least one mismatch. In some embodiments, C and/or D, independently, include at least one alternative nucleobase, at least one alternative internucleoside linkage, and/or at least one alternative sugar moiety.

In some embodiments, C includes a nucleobase sequence having at least 50% sequence identity (e.g., at least 50%, at least 60%, at least 70%, at least 80%, at least 85%, at least 90%, at least 95%, at least 96%, at least 97%, at least 98%, at least 99%, or 100% sequence identity) to a nucleobase sequence set forth in of any one of SEQ ID NOs. 1, 4, 7, 10, 13, 16, 19, 22, 25, 28, 31, and 34, and D includes a nucleobase sequence complementary to the nucleobase sequence of C, wherein the sequence includes at least one mismatch as described herein. In other embodiments, D includes a nucleobase sequence having at least 50% sequence identity (e.g., at least 50%, at least 60%, at least 70%, at least 80%, at least 85%, at least 90%, at least 95%, at least 96%, at least 97%, at least 98%, at least 99%, or 100% sequence identity) to a nucleobase sequence set forth in of any one of SEQ ID NOs. 2, 5, 8, 11, 14, 17, 20, 23, 26, 29, 32, and 35, and C includes a nucleobase sequence complementary to the nucleobase sequence of C, wherein the sequence includes at least one mismatch as described herein. In some embodiments, C-$L_1$-D includes a nucleobase sequence having at least 50% sequence identity (e.g., at least 50%, at least 60%, at least 70%, at least 80%, at least 85%, at least 90%, at least 95%, at least 96%, at least 97%, at least 98%, at least 99%, or 100% sequence identity) to a nucleobase sequence set forth in of any one of SEQ ID NOs. 3, 6, 9, 12, 15, 18, 21, 24, 27, 30, 33, and 36, wherein the sequence includes at least one mismatch as described herein.

Nucleobase sequences of SEQ ID NOs. 1-36 are provided below:

TABLE 4

| | |
|---|---|
| GGUGAAUAGUAUAACAAUAU | SEQ ID NO. 1 |
| AUGUUGUUAUAGUAUCCACC | SEQ ID NO. 2 |
| GGUGAAUAGUAUAACAAUAUGCUAAAUGUUGUUAUAGUAUCCACC | SEQ ID NO. 3 |
| GGUGAAGAGGAGAACAAUAU | SEQ ID NO. 4 |
| AUGUUGUUCUCGUCUCCACC | SEQ ID NO. 5 |
| GGUGAAGAGGAGAACAAUAUGCUAAAUGUUGUUCUCGUCUCCACC | SEQ ID NO. 6 |
| GGUGUCGAGAAGAGGAGAACAAUAU | SEQ ID NO. 7 |
| AUGUUGUUCUCGUCUCCUCGACACC | SEQ ID NO. 8 |
| GGUGUCGAGAAGAGGAGAACAAUAUGCUAAAUGUUGUUCUCGUCUCCUCGACACC | SEQ ID NO. 9 |
| GGGUGGAAUAGUAUAACAAUAU | SEQ ID NO. 10 |
| AUGUUGUUAUAGUAUCCCACCU | SEQ ID NO. 11 |
| GGGUGGAAUAGUAUAACAAUAUGCUAAAUGUUGUUAUAGUAUCCCACCU | SEQ ID NO. 12 |
| GUGGAAUAGUAUAACAAUAU | SEQ ID NO. 13 |
| AUGUUGUUAUAGUAUCCCAC | SEQ ID NO. 14 |
| GUGGAAUAGUAUAACAAUAUGCUAAAUGUUGUUAUAGUAUCCCAC | SEQ ID NO. 15 |
| GGUGUCGAGAAUAGUAUAACAAUAU | SEQ ID NO. 16 |
| AUGUUGUUAUAGUAUCCUCGACACC | SEQ ID NO. 17 |
| GGUGUCGAGAAUAGUAUAACAAUAUGCUAAAUGUUGUUAUAGUAUCCUCGACACC | SEQ ID NO. 18 |
| GGGUGGAAUAGUAUAACAAUAU | SEQ ID NO. 19 |
| AUGUUGUUAUAGUAUCCCACCU | SEQ ID NO. 20 |
| GGGUGGAAUAGUAUAACAAUAUGCUAAAUGUUGUUAUAGUAUCCCACCU | SEQ ID NO. 21 |
| GGGUGGAAUAGUAUACCA | SEQ ID NO. 22 |
| UGGUAUAGUAUCCCACCU | SEQ ID NO. 23 |
| GGGUGGAAUAGUAUACCAUUCGUGGUAUAGUAUCCCACCU | SEQ ID NO. 24 |
| GUGGGUGGAAUAGUAUACCA | SEQ ID NO. 25 |
| UGGUAUAGUAUCCCACCUAC | SEQ ID NO. 26 |
| GUGGGUGGAAUAGUAUACCAUUCGUGGUAUAGUAUCCCACCUAC | SEQ ID NO. 27 |
| UGGGUGGAAUAGUAUACCA | SEQ ID NO. 28 |
| UGGUAUAGUAUCCCACCUA | SEQ ID NO. 29 |
| UGGGUGGAAUAGUAUACCAUUCGUGGUAUAGUAUCCCACCUA | SEQ ID NO. 30 |
| GGUGGAAUAGUAUACCA | SEQ ID NO. 31 |
| UGGUAUAGUAUCCCACC | SEQ ID NO. 32 |
| GGUGGAAUAGUAUACCAUUCGUGGUAUAGUAUCCCACC | SEQ ID NO. 33 |
| GUGGAAUAGUAUACCA | SEQ ID NO. 34 |

TABLE 4-continued

| | |
|---|---|
| UGGUAUAGUAUCCCAC | SEQ ID NO. 35 |
| GUGGAAUAGUAUACCAUUCGUGGUAUAGUAUCCCAC | SEQ ID NO. 36 |

It will be understood that, although the sequences in SEQ ID NOs. 1-36 are described as unmodified and/or unconjugated sequences, the RNA of the oligonucleotides of the invention may include any one of the sequences set forth in SEQ ID NOs. 1-36 that is an alternative nucleoside and/or conjugated as described in detail below.

In some embodiments, the oligonucleotide of the invention may further include a 5' cap structure. In some embodiments, the 5' cap structure is a 2,2,7-trimethylguanosine cap.

An oligonucleotide of the invention can be synthesized by standard methods known in the art as further discussed below, e.g., by use of an automated DNA synthesizer, such as are commercially available from, for example, Biosearch, Applied Biosystems, Inc.

The oligonucleotide compound can be prepared using solution-phase or solid-phase organic synthesis or both. Organic synthesis offers the advantage that the oligonucleotide including unnatural or alternative nucleotides can be easily prepared. Single-stranded oligonucleotides of the invention can be prepared using solution-phase or solid-phase organic synthesis or both.

Further, it is contemplated that for any sequence identified herein, further optimization could be achieved by systematically either adding or removing linked nucleosides to generate longer or shorter sequences. Further still, such optimized sequences can be adjusted by, e.g., the introduction of alternative nucleosides, alternative sugar moieties, and/or alternative internucleosidic linkages as described herein or as known in the art, including alternative nucleosides, alternative sugar moieties, and/or alternative internucleosidic linkages as known in the art and/or discussed herein to further optimize the molecule (e.g., increasing serum stability or circulating half-life, increasing thermal stability, enhancing transmembrane delivery, targeting to a particular location or cell type, and/or increasing interaction with RNA editing enzymes (e.g., ADAR)).

In some embodiments, the oligonucleotides include one ADAR-recruiting domain. In some embodiments, the ADAR-recruiting domain is at the 5' end of the oligonucleotide. In some embodiments, the ADAR-recruiting domain is at the 3' end of the oligonucleotide. In some embodiments, the oligonucleotides include a first ADAR-recruiting domain and a second ADAR-recruiting domain. In some embodiments, the first ADAR-recruiting domain is at the 5' end of the oligonucleotide, wherein the second ADAR-recruiting domain is at the 3' end of the oligonucleotide. In some embodiments, the one or more ADAR-recruiting domains are GluR2 ADAR-recruiting domains. In some embodiments, the GluR2 ADAR-recruiting domain has the nucleotide sequence of SEQ ID NO. 37, as shown below in the 5' to 3' direction:

(SEQ ID NO. 37)
GGUGAAUAGUAUAACAAUAUGCUAAAUGUUGUUAUAGUAUCCACC

In some embodiments, the oligonucleotide includes the structure of Formula XII, as shown below:

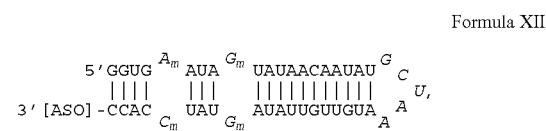

Formula XII wherein [ASO] includes any of the oligonucleotides of the instant invention, wherein m designates a mismatched nucleotide. In some embodiments, the GluR2 ADAR-recruiting domain has the nucleotide sequence of SEQ ID NO. 38, as shown below in the 5' to 3' direction:

(SEQ ID NO. 38)
GGUGAAGAGGAGAACAAUAUGCUAAAUGUUGUUCUCGUCUCCACC

In some embodiments, the oligonucleotide includes the structure of Formula XIII, as shown below:

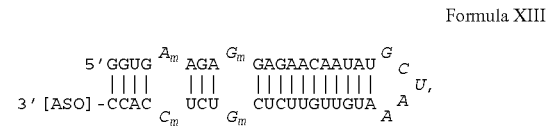

Formula XIII wherein [ASO] includes any of the oligonucleotides of the instant invention, wherein m designates a mismatched nucleotide. In some embodiments, the GluR2 ADAR-recruiting domain has the nucleotide sequence of SEQ ID NO. 39, as shown below in the 5' to 3' direction:

(SEQ ID NO. 39)
GGUGUCGAGAAGAGGAGAACAAUAUGCUAAAUGUUGUUCUCGUCUCCUCGACACC

In some embodiments, the oligonucleotide includes the structure of Formula XIV, as shown below:

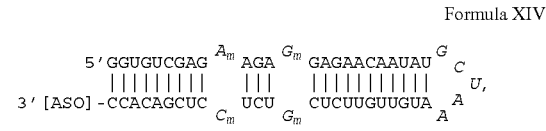

Formula XIV wherein [ASO] includes any of the oligonucleotides of the instant invention, wherein m designates a mismatched nucleotide.

In some embodiments, the GluR2 ADAR-recruiting domain has the nucleotide sequence of SEQ ID NO. 40, as shown below in the 5' to 3' direction:

(SEQ ID NO. 40)
s*s*G**GAGAAGAGGAGAA*AA*A*G**AAA*GG***G
******GA*A** wherein * is a 2'-O-methyl nucleotide and s is a phosphorothioate internucleoside linkage between two linked nucleotides. In some embodiments, the oligonucleotide includes the structure of Formula XV, as shown below:

Formula XV

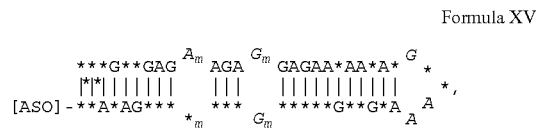

wherein [ASO] includes any of the oligonucleotides of the instant invention, wherein * is a 2'-O-methyl nucleotide, wherein s is a phosphorothioate internucleoside linkage, wherein m designates a mismatched nucleotide. In some embodiments, the ADAR-recruiting domains further include at least one nuclease-resistant nucleotide (e.g., 2-O-methyl nucleotide). In some embodiments, the ADAR-recruiting domains include at least one alternative internucleoside linkage (e.g., a phosphorothioate internucleoside linkage). In some embodiments, the GluR2 ADAR-recruiting domain has the nucleotide sequence of SEQ ID NO. 41, as shown below in the 5' to 3' direction:

(SEQ ID NO. 41)
GGGUGGAAUAGUAUAACAAUAUGCUAAAUGUUGUUAUAGUAUCCCACCU

In some embodiments, the oligonucleotide includes the structure of Formula XVI, as shown below:

Formula XVI

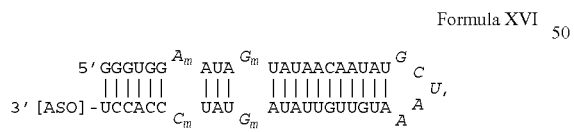

wherein [ASO] includes any of the oligonucleotides of the instant invention, wherein m designates a mismatched nucleotide. In some embodiments, the GluR2 ADAR-recruiting domain has the nucleotide sequence of SEQ ID NO. 42, as shown below in the 5' to 3' direction:

(SEQ ID NO. 42)
GUGGAAUAGUAUAACAAUAUGCUAAAUGUUGUUAUAGUAUCCCAC

In some embodiments, the oligonucleotide includes the structure of Formula XVII, as shown below:

Formula XVII

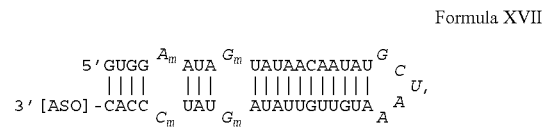

wherein [ASO] includes any of the oligonucleotides of the instant invention, wherein m designates a mismatched nucleotide. In some embodiments, the GluR2 ADAR-recruiting domain has the nucleotide sequence of SEQ ID NO. 43, as shown below in the 5' to 3' direction:

(SEQ ID NO. 43)
GGUGUCGAGAAUAGUAUAACAAUAUGCUAAAUGUUGUUAUAGUAUCCUC
GACACC

In some embodiments, the oligonucleotide includes the structure of Formula XVIII, as shown below:

Formula XVIII

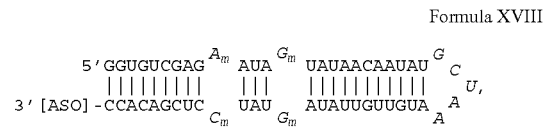

wherein [ASO] includes any of the oligonucleotides of the instant invention, wherein m designates a mismatched nucleotide. In some embodiments, the GluR2 ADAR-recruiting domain has the nucleotide sequence of SEQ ID NO. 44, as shown below in the 5' to 3' direction:

(SEQ ID NO. 44)
GGGUGGAAUAGUAUAACAAUAUGCUAAAUGUUGUUAUAGUAUCCCACCU

In some embodiments, the oligonucleotide includes the structure of Formula XIX, as shown below:

Formula XIX

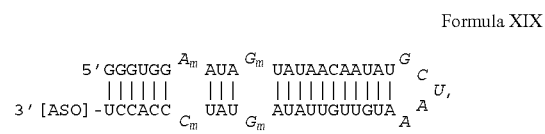

wherein [ASO] includes any of the oligonucleotides of the instant invention, wherein m designates a mismatched nucleotide. In some embodiments, the GluR2 ADAR-recruiting domain has the nucleotide sequence of SEQ ID NO. 45, as shown below in the 5' to 3' direction:

(SEQ ID NO. 45)
GGGUGGAAUAGUAUACCAUUCGUGGUAUAGUAUCCCACCU

In some embodiments, the oligonucleotide includes the structure of Formula XX, as shown below:

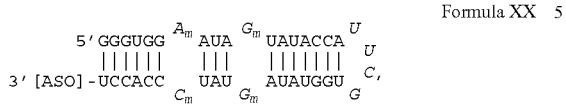

Formula XX wherein [ASO] includes any of the oligonucleotides of the instant invention, wherein m designates a mismatched nucleotide. In some embodiments, the GluR2 ADAR-recruiting domain has the nucleotide sequence of SEQ ID NO. 46, as shown below in the 5' to 3' direction:

(SEQ ID NO. 46)
GUGGGUGGAAUAGUAUACCAUUCGUGGUAUAGUAUCCCACCUAC

In some embodiments, the oligonucleotide includes the structure of Formula XXI, as shown below:

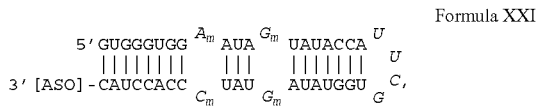

Formula XXI wherein [ASO] includes any of the oligonucleotides of the instant invention, wherein m designates a mismatched nucleotide. In some embodiments, the GluR2 ADAR-recruiting domain has the nucleotide sequence of SEQ ID NO. 47, as shown below in the 5' to 3' direction:

(SEQ ID NO. 47)
UGGGUGGAAUAGUAUACCAUUCGUGGUAUAGUAUCCCACCUA

In some embodiments, the oligonucleotide includes the structure of Formula XXII, as shown below:

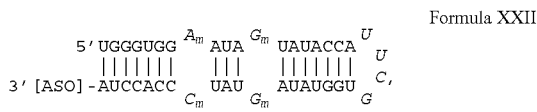

Formula XXII wherein [ASO] includes any of the oligonucleotides of the instant invention, wherein m designates a mismatched nucleotide. In some embodiments, the GluR2 ADAR-recruiting domain has the nucleotide sequence of SEQ ID NO. 48, as shown below in the 5' to 3' direction:

(SEQ ID NO. 48)
GGUGGAAUAGUAUACCAUUCGUGGUAUAGUAUCCCACC

In some embodiments, the oligonucleotide includes the structure of Formula XXIII, as shown below:

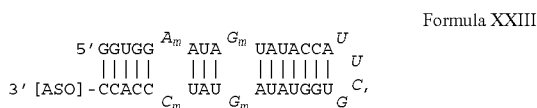

Formula XXIII wherein [ASO] includes any of the oligonucleotides of the instant invention, wherein m designates a mismatched nucleotide. In some embodiments, the GluR2 ADAR-recruiting domain has the nucleotide sequence of SEQ ID NO. 49, as shown below in the 5' to 3' direction:

(SEQ ID NO. 49)
GUGGAAUAGUAUACCAUUCGUGGUAUAGUAUCCCAC

In some embodiments, the oligonucleotide includes the structure of Formula XIV, as shown below:

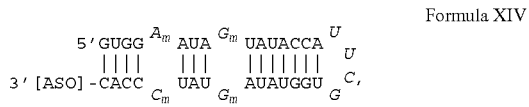

Formula XIV wherein [ASO] includes any of the oligonucleotides of the instant invention, wherein m designates a mismatched nucleotide.

In some embodiments, the ADAR-recruiting domains are Z-DNA ADAR-recruiting domains. In some embodiments, the ADAR-recruiting domains are MS2 ADAR-recruiting domains. In some embodiments, an MS2 bacteriophage stem-loop structure may be used as an ADAR-recruiting domain (e.g., and MS2 ADAR-recruiting domain). MS2 stem-loops are known to bind the MS2 bacteriophage coat protein, which when fused to the deaminase domain of ADAR (e.g. an ADAR fusion protein) can be used for target-specific deamination. In some embodiments, the MS2 ADAR-recruiting domain has the nucleotide sequence of SEQ ID NO. 50, as shown below in the 5' to 3' direction:

(SEQ ID NO. 50)
ACATGAGGATCACCCATGT

In some embodiments, an ADAR fusion protein is administered to the cell or to the subject using an expression vector construct including a polynucleotide encoding an ADAR fusion protein. In some embodiments, the ADAR fusion protein includes a deaminase domain of ADAR fused to an MS2 bacteriophage coat protein. In some embodiments, the deaminase domain of ADAR is a deaminase domain of ADAR1. In some embodiments, the deaminase domain of ADAR is a deaminase domain of ADAR2. The ADAR fusion protein may be a fusion protein described in Katrekar et al. Nature Methods, 16(3): 239-42 (2019), the ADAR fusion protein of which is herein incorporated by reference.

The nucleic acids featured in the invention can be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Alternative nucleotides and nucleosides include those with modifications including, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; and/or backbone modifications, including modification or replacement of the phosphodiester linkages. The nucleobase may also be an isonucleoside in which the nucleobase is moved from the C1 position of the sugar moiety to a different position (e.g. C2, C3, C4, or C5). Specific examples of oligonucleotide compounds useful in the embodiments described herein include but are not limited to alternative nucleosides containing modified backbones or no natural internucleoside linkages. Nucleotides and nucleosides having modified backbones include, among others, those that do not have a phosphorus atom in the backbone. For the purposes of this specification, and as sometimes referenced in the art, alternative RNAs that do not have a phosphorus atom in their internucleoside backbone can also be considered to be oligonucleosides. In some embodiments, an oligonucleotide will have a phosphorus atom in its internucleoside backbone.

Alternative internucleoside linkages include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boronophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts, and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, the entire contents of each of which are hereby incorporated herein by reference.

Alternative internucleoside linkages that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, the entire contents of each of which are hereby incorporated herein by reference.

In other embodiments, suitable oligonucleotides include those in which both the sugar and the internucleoside linkage, i.e., the backbone, of the nucleotide units are replaced. The base units are maintained for hybridization with an appropriate nucleic acid target compound. One such oligomeric compound, a mimetic that has been shown to have excellent hybridization properties, is referred to as a peptide nucleic acid (PNA). In PNA compounds, the sugar of a nucleoside is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the oligonucleotides of the invention are described in, for example, in Nielsen et al., Science, 1991, 254, 1497-1500.

Some embodiments featured in the invention include oligonucleotides with phosphorothioate backbones and oligonucleotides with heteroatom backbones, and in particular $—CH_2—NH—CH_2—$, $—CH_2—N(CH_3)—O—CH_2$- [known as a methylene (methylimino) or MMI backbone], $—CH_2—O—N(CH_3)—CH_2—$, $—CH_2—N(CH_3)—N(CH_3)—CH_2—$ and $—N(CH_3)—CH_2—CH_2—$ [wherein the native phosphodiester backbone is represented as $—O—P—O—CH_2—$] of the above-referenced U.S. Pat. No. 5,489,677, and the amide backbones of the above-referenced U.S. Pat. No. 5,602,240. In some embodiments, the oligonucleotides featured herein have morpholino backbone structures of the above-referenced U.S. Pat. No. 5,034,506. In other embodiments, the oligonucleotides described herein include phosphorodiamidate morpholino oligomers (PMO), in which the deoxyribose moiety is replaced by a morpholine ring, and the charged phosphodiester inter-subunit linkage is replaced by an uncharged phophorodiamidate linkage, as described in Summerton, et al., Antisense Nucleic Acid Drug Dev. 1997, 7:63-70.

Alternative nucleosides and nucleotides can also contain one or more substituted sugar moieties. The oligonucleotides, e.g., oligonucleotides, featured herein can include one of the following at the 2'-position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include $—O[(CH_2)_nO]_mCH_3$, $—O(CH_2)_nOCH_3$, $—O(CH_2)_n—NH_2$, $—O(CH_2)_nCH_3$, $—O(CH_2)_n—ONH_2$, and $—O(CH_2)_n—ON[(CH_2)_nCH_3]_2$, where n and m are from 1 to about 10. In other embodiments, oligonucleotides include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In some embodiments, the modification includes a 2'-methoxyethoxy (2'-O—$CH_2CH_2OCH_3$, also known as 2'-O-(2-methoxyethyl) or 2'-O-MOE) (Martin et al., Helv. Chin. Acta, 1995, 78:486-504) i.e., an alkoxy-alkoxy group. 2'-O-MOE nucleosides confer several beneficial properties to oligonucleotides including, but not limited to, increased nuclease resistance, improved pharmacokinetics properties, reduced non-specific protein binding, reduced toxicity, reduced immunostimulatory properties, and enhanced target affinity as compared to unmodified oligonucleotides.

Another exemplary alternative contains 2'-dimethylaminooxyethoxy, i.e., a —O(CH$_2$)$_2$ON(CH$_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—(CH$_2$)$_2$—O—(CH$_2$)$_2$—N(CH$_3$)$_2$. Further exemplary alternatives include: 5'-Me-2'-F nucleotides, 5'-Me-2'-OMe nucleotides, 5'-Me-2'-deoxynucleotides, (both R and S isomers in these three families); 2'-alkoxyalkyl; and 2'-NMA (N-methylacetamide).

Other alternatives include 2'-methoxy (2'-OCH$_3$), 2'-aminopropoxy (2'-OCH$_2$CH$_2$CH$_2$NH$_2$) and 2'-fluoro (2'-F). Similar modifications can also be made at other positions on the nucleosides and nucleotides of an oligonucleotide, particularly the 3' position of the sugar on the 3' terminal nucleotide or in 2'-5' linked oligonucleotides and the 5' position of 5' terminal nucleotide. Oligonucleotides can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

An oligonucleotide of the invention can also include nucleobase (often referred to in the art simply as "base") alternatives (e.g., modifications or substitutions). Unmodified or natural nucleobases include the purine bases adenine (A) and guanine (G), and the pyrimidine bases thymine (T), cytosine (C) and uracil (U). Alternative nucleobases include other synthetic and natural nucleobases such as 5-methylcytosine, 5-hydroxymethylcytosine, 5-formylcytosine, 5-carboxycytosine, pyrrolocytosine, dideoxycytosine, uracil, 5-methoxyuracil, 5-hydroxydeoxyuracil, dihydrouracil, 4-thiouracil, pseudouracil, 1-methyl-pseudouracil, deoxyuracil, 5-hydroxybutynl-2'-deoxyuracil, xanthine, hypoxanthine, 7-deaza-xanthine, thienoguanine, 8-aza-7-deazaguanine, 7-methylguanine, 7-deazaguanine, 6-aminomethyl-7-deazaguanine, 8-aminoguanine, 2,2,7-trimethylguanine, 8-methyladenine, 8-azidoadenine, 7-methyladenine, 7-deazaadenine, 3-deazaadenine, 2,6-diaminopurine, 2-aminopurine, 7-deaza-8-aza-adenine, 8-amino-adenine, thymine, dideoxythymine, 5-nitroindole, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 8-azaguanine and 8-azaadenine, and 3-deazaguanine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., (1991) Angewandte Chemie, International Edition, 30:613, and those disclosed by Sanghvi, Y S., Chapter 15, Antisense Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines, and N-2, N-6 and O-6 substituted purines, including 2-aminopropyladenine, 5-propynyluracil, and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., Antisense Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted alternative nucleobases as well as other alternative nucleobases include, but are not limited to, the above noted U.S. Pat. Nos. 3,687,808, 4,845,205; 5,130, 30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

In other embodiments, the sugar moiety in the nucleotide may be a ribose molecule, optionally having a 2'-O-methyl, 2'-O-MOE, 2'-F, 2'-amino, 2'-O-propyl, 2'-aminopropyl, or 2'-OH modification.

An oligonucleotide of the invention can include one or more bicyclic sugar moieties. A "bicyclic sugar" is a furanosyl ring modified by the bridging of two atoms. A "bicyclic nucleoside" ("BNA") is a nucleoside having a sugar moiety including a bridge connecting two carbon atoms of the sugar ring, thereby forming a bicyclic ring system. In certain embodiments, the bridge connects the 4'-carbon and the 2'-carbon of the sugar ring. Thus, in some embodiments an agent of the invention may include one or more locked nucleosides. A locked nucleoside is a nucleoside having a modified ribose moiety in which the ribose moiety includes an extra bridge connecting the 2' and 4' carbons. In other words, a locked nucleoside is a nucleoside including a bicyclic sugar moiety including a 4'-CH$_2$—O-2' bridge. This structure effectively "locks" the ribose in the 3'-endo structural conformation. The addition of locked nucleosides to oligonucleotides has been shown to increase oligonucleotide stability in serum, and to reduce off-target effects (Grunweller, A. et al., (2003) Nucleic Acids Research 31(12): 3185-3193). Examples of bicyclic nucleosides for use in the polynucleotides of the invention include without limitation nucleosides including a bridge between the 4' and the 2' ribosyl ring atoms. In certain embodiments, the polynucleotide agents of the invention include one or more bicyclic nucleosides including a 4' to 2' bridge. Examples of such 4' to 2' bridged bicyclic nucleosides, include but are not limited to 4'-(CH$_2$)—O-2' (LNA); 4'-(CH$_2$)—S-2'; 4'-(CH$_2$)$_2$—O-2' (ENA); 4'-CH(CH$_3$)—O-2' (also referred to as "constrained ethyl" or "cEt") and 4'-CH(CH$_2$OCH$_3$)—O-2' (and analogs thereof; see, e.g., U.S. Pat. No. 7,399,845); 4'-C(CH$_3$)(CH$_3$)—O-2' (and analogs thereof; see e.g., U.S. Pat. No. 8,278,283); 4'-CH$_2$—N(OCH$_3$)-2' (and analogs thereof; see e.g., U.S. Pat. No. 8,278,425); 4'-CH$_2$—O—N(CH$_3$)$_2$-2' (see, e.g., U.S. Patent Publication No. 2004/0171570); 4'-CH$_2$—N(R)—O-2', wherein R is H, C$_1$-C$_{12}$ alkyl, or a protecting group (see, e.g., U.S. Pat. No. 7,427,672); 4'-CH$_2$—C(H)(CH$_3$)-2' (see, e.g., Chattopadhyaya et al., J.

Org. Chem., 2009, 74, 118-134); and 4'-CH$_2$—C(=CH$_2$)-2' (and analogs thereof; see, e.g., U.S. Pat. No. 8,278,426). The entire contents of each of the foregoing are hereby incorporated herein by reference.

Additional representative U.S. Patents and US Patent Publications that teach the preparation of locked nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 2008/0039618; and US 2009/0012281, the entire contents of each of which are hereby incorporated herein by reference.

Any of the foregoing bicyclic nucleosides can be prepared having one or more stereochemical sugar configurations including for example α-L-ribofuranose and β-D-ribofuranose (see WO 99/14226).

An oligonucleotide of the invention can also be modified to include one or more constrained ethyl nucleotides. As used herein, a "constrained ethyl nucleotide" or "cEt" is a locked nucleic acid including a bicyclic sugar moiety including a 4'-CH(CH$_3$)—O-2' bridge. In one embodiment, a constrained ethyl nucleotide is in the S conformation referred to herein as "S-cEt."

An oligonucleotide of the invention may also include one or more "conformationally restricted nucleotides" ("CRN"). CRN are nucleotide analogs with a linker connecting the C2' and C4' carbons of ribose or the C3 and —C5' carbons of ribose. CRN lock the ribose ring into a stable conformation and increase the hybridization affinity to mRNA. The linker is of sufficient length to place the oxygen in an optimal position for stability and affinity resulting in less ribose ring puckering.

Representative publications that teach the preparation of certain of the above noted CRN include, but are not limited to, US Patent Publication No. 2013/0190383; and PCT publication WO 2013/036868, the entire contents of each of which are hereby incorporated herein by reference.

In some embodiments, an oligonucleotide of the invention includes one or more monomers that are UNA (unlocked nucleic acid) nucleotides. UNA is unlocked acyclic nucleic acid, wherein any of the bonds of the sugar has been removed, forming an unlocked "sugar" residue. In one example, UNA also encompasses monomer with bonds between C1'-C4' have been removed (i.e. the covalent carbon-oxygen-carbon bond between the C1' and C4' carbons). In another example, the C2'-C3' bond (i.e. the covalent carbon-carbon bond between the C2' and C3' carbons) of the sugar has been removed (see Nuc. Acids Symp. Series, 52, 133-134 (2008) and Fluiter et al., Mol. Biosyst., 2009, 10, 1039 hereby incorporated by reference).

Representative U.S. publications that teach the preparation of UNA include, but are not limited to, U.S. Pat. No. 8,314,227; and US Patent Publication Nos. 2013/0096289; 2013/0011922; and 2011/0313020, the entire contents of each of which are hereby incorporated herein by reference.

The ribose molecule may also be modified with a cyclopropane ring to produce a tricyclodeoxynucleic acid (tricyclo DNA). The ribose moiety may be substituted for another sugar such as 1,5,-anhydrohexitol, threose to produce a threose nucleoside (TNA), or arabinose to produce an arabino nucleoside. The ribose molecule can also be replaced with non-sugars such as cyclohexene to produce cyclohexene nucleoside or glycol to produce glycol nucleosides.

The ribose molecule can also be replaced with non-sugars such as cyclohexene to produce cyclohexene nucleic acid (CeNA) or glycol to produce glycol nucleic acids (GNA).

Potentially stabilizing modifications to the ends of nucleotide molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in PCT Publication No. WO 2011/005861.

Other alternatives chemistries of an oligonucleotide of the invention include a 5' phosphate or 5' phosphate mimic, e.g., a 5'-terminal phosphate or phosphate mimic of an oligonucleotide. Suitable phosphate mimics are disclosed in, for example US Patent Publication No. 2012/0157511, the entire contents of which are incorporated herein by reference.

Exemplary oligonucleotides of the invention include sugar-modified nucleosides and may also include DNA or RNA nucleosides. In some embodiments, the oligonucleotide includes sugar-modified nucleosides and DNA nucleosides. Incorporation of alternative nucleosides into the oligonucleotide of the invention may enhance the affinity of the oligonucleotide for the target nucleic acid. In that case, the alternative nucleosides can be referred to as affinity enhancing alternative nucleotides.

In some embodiments, the oligonucleotide includes at least 1 alternative nucleoside, such as at least 2, at least 3, at least 4, at least 5, at least 6, at least 7, at least 8, at least 9, at least 10, at least 11, at least 12, at least 13, at least 14, at least 15 or at least 16 alternative nucleosides. In other embodiments, the oligonucleotides include from 1 to 10 alternative nucleosides, such as from 2 to 9 alternative nucleosides, such as from 3 to 8 alternative nucleosides, such as from 4 to 7 alternative nucleosides, such as 6 or 7 alternative nucleosides. In an embodiment, the oligonucleotide of the invention may include alternatives, which are independently selected from these three types of alternative (alternative sugar moiety, alternative nucleobase, and alternative internucleoside linkage), or a combination thereof. Preferably the oligonucleotide includes one or more nucleosides including alternative sugar moieties, e.g., 2' sugar alternative nucleosides. In some embodiments, the oligonucleotide of the invention include the one or more 2' sugar alternative nucleoside independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, ANA, 2'-fluoro-ANA, and BNA (e.g., LNA) nucleosides. In some embodiments, the one or more alternative nucleoside is a BNA.

In some embodiments, at least 1 of the alternative nucleosides is a BNA (e.g., an LNA), such as at least 2, such as at least 3, at least 4, at least 5, at least 6, at least 7, or at least 8 of the alternative nucleosides are BNAs. In a still further embodiment, all the alternative nucleosides are BNAs.

In a further embodiment the oligonucleotide includes at least one alternative internucleoside linkage. In some embodiments, the internucleoside linkages within the contiguous nucleotide sequence are phosphorothioate or boronophosphate internucleoside linkages. In some embodiments, all the internucleotide linkages in the contiguous sequence of the oligonucleotide are phosphorothioate linkages. In some embodiments the phosphorothioate linkages are stereochemically pure phosphorothioate linkages. IN some embodiments, the phosphorothioate linkages are Sp phosphorothioate linkages. In other embodiments, the phosphorothioate linkages are Rp phosphorothioate linkages.

In some embodiments, the oligonucleotide of the invention includes at least one alternative nucleoside which is a 2'-O-MOE-RNA, such as 2, 3, 4, 5, 6, 7, 8, 9, or 10 2'-O-MOE-RNA nucleoside units. In some embodiments, the 2'-O-MOE-RNA nucleoside units are connected by phosphorothioate linkages. In some embodiments, at least one of said alternative nucleoside is 2'-fluoro DNA, such as 2, 3, 4, 5, 6, 7, 8, 9, or 10 2'-fluoro-DNA nucleoside units. In some embodiments, the oligonucleotide of the invention includes at least one BNA unit and at least one 2' substituted alternative nucleoside. In some embodiments of the invention, the oligonucleotide includes both 2' sugar modified nucleosides and DNA units. In some embodiments, the oligonucleotide of the invention or contiguous nucleotide region thereof is a gapmer oligonucleotide.

B. Oligonucleotide Conjugated to Ligands

Oligonucleotides of the invention may be chemically linked to one or more ligands, moieties, or conjugates that enhance the activity, cellular distribution, or cellular uptake of the oligonucleotide. Such moieties include but are not limited to lipid moieties such as a cholesterol moiety (Letsinger et al., (1989) Proc. Natl. Acad. Sci. USA, 86: 6553-6556), cholic acid (Manoharan et al., (1994) Biorg. Med. Chem. Let., 4:1053-1060), a thioether, e.g., beryl-S-tritylthiol (Manoharan et al., (1992) Ann. N.Y. Acad. Sci., 660:306-309; Manoharan et al., (1993) Biorg. Med. Chem. Let., 3:2765-2770), a thiocholesterol (Oberhauser et al., (1992) Nucl. Acids Res., 20:533-538), an aliphatic chain, e.g., dodecandiol or undecyl residues (Saison-Behmoaras et al., (1991) EMBO J, 10:1111-1118; Kabanov et al., (1990) FEBS Lett., 259:327-330; Svinarchuk et al., (1993) Biochimie, 75:49-54), a phospholipid, e.g., di-hexadecyl-rac-glycerol or triethyl-ammonium 1,2-di-O-hexadecyl-rac-glycero-3-phosphonate (Manoharan et al., (1995) Tetrahedron Lett., 36:3651-3654; Shea et al., (1990) Nucl. Acids Res., 18:3777-3783), a polyamine or a polyethylene glycol chain (Manoharan et al., (1995) Nucleosides & Nucleotides, 14:969-973), or adamantane acetic acid (Manoharan et al., (1995) Tetrahedron Lett., 36:3651-3654), a palmityl moiety (Mishra et al., (1995) Biochim. Biophys. Acta, 1264:229-237), or an octadecylamine or hexylamino-carbonyloxycholesterol moiety (Crooke et al., (1996) J. Pharmacol. Exp. Ther., 277:923-937).

In one embodiment, a ligand alters the distribution, targeting, or lifetime of an oligonucleotide agent into which it is incorporated. In some embodiments, a ligand provides an enhanced affinity for a selected target, e.g., molecule, cell or cell type, compartment, e.g., a cellular or organ compartment, tissue, organ, or region of the body, as, e.g., compared to a species absent such a ligand.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, N-acetylglucosamine, N-acetylgalactosamine, or hyaluronic acid); or a lipid. The ligand can also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly (2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic.

Other examples of ligands include dyes, intercalating agents (e.g. acridines), cross-linkers (e.g. psoralen, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid,O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a hepatic cell. Ligands can also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose.

The ligand can be a substance, e.g., a drug, which can increase the uptake of the oligonucleotide agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In some embodiments, a ligand attached to an oligonucleotide as described herein acts as a pharmacokinetic modulator (PK modulator). PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that include a number of phosphorothioate linkages are also known to bind to serum protein, thus short oligonucleotides, e.g., oligonucleotides of about 5 bases, 10 bases, 15 bases, or 20 bases, including multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

Ligand-conjugated oligonucleotides of the invention may be synthesized by the use of an oligonucleotide that bears a pendant reactive functionality, such as that derived from the attachment of a linking molecule onto the oligonucleotide (described below). This reactive oligonucleotide may be reacted directly with commercially-available ligands, ligands that are synthesized bearing any of a variety of protecting groups, or ligands that have a linking moiety attached thereto.

The oligonucleotides used in the conjugates of the present invention may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides, such as the phosphorothioates and alkylated derivatives.

In the ligand-conjugated oligonucleotides of the present invention, such as the ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

i. Lipid Conjugates

In one embodiment, the ligand or conjugate is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid-based ligand can be used to inhibit, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In another aspect, the ligand is a moiety, e.g., a vitamin, which is taken up by a target cell, e.g., a proliferating cell. Exemplary vitamins include vitamin A, E, and K.

ii. Cell Permeation Agents

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the oligonucleotide, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp, or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO. 71). An RFGF analogue (e.g., amino acid sequence AALLPVL-LAAP (SEQ ID NO. 72) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ; SEQ ID NO. 73) and the Drosophila Antennapedia protein (RQIKIWFQNRRMKWKK; SEQ ID NO. 74) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Examples of a peptide or peptidomimetic tethered to an oligonucleotide agent via an incorporated monomer unit for cell targeting purposes is an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods of the invention may be linear or cyclic, and may be modified, e.g., glycosylated or methylated, to facilitate targeting to a specific tissue(s). RGD-containing peptides and peptidomimetics may include D-amino acids, as well as synthetic RGD mimics. In addition to RGD, one can use other moieties that target the integrin ligand. Some conjugates of this ligand target PECAM-1 or VEGF.

A cell permeation peptide is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin, or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

iii. Carbohydrate Conjugates

In some embodiments of the compositions and methods of the invention, an oligonucleotide further includes a carbohydrate. The carbohydrate conjugated oligonucleotide is advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri- and oligosaccharides containing from about 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars; di- and trisaccharides include sugars having two or three monosaccharide units (e.g., C5, C6, C7, or C8).

In one embodiment, a carbohydrate conjugate for use in the compositions and methods of the invention is a monosaccharide.

In some embodiments, the carbohydrate conjugate further includes one or more additional ligands as described above, such as, but not limited to, a PK modulator and/or a cell permeation peptide.

Additional carbohydrate conjugates (and linkers) suitable for use in the present invention include those described in PCT Publication Nos. WO 2014/179620 and WO 2014/179627, the entire contents of each of which are incorporated herein by reference.

iv. Linkers

In some embodiments, the conjugate or ligand described herein can be attached to an oligonucleotide with various linkers that can be cleavable or non-cleavable.

Linkers typically include a direct bond or an atom such as oxygen or sulfur, a unit such as $NR^8$, C(O), C(O)NH, SO, $SO_2$, $SO_2NH$ or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, $N(R^8)$, C(O), substituted or unsubstituted aryl, substituted or unsubstituted heteroaryl, substituted or unsubstituted heterocyclic; where $R^8$ is hydrogen, acyl, aliphatic or substituted aliphatic. In one embodiment, the linker is between about 1-24 atoms, 2-24, 3-24, 4-24, 5-24, 6-24, 6-18, 7-18, 8-18 atoms, 7-17, 8-17, 6-16, 7-17, or 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least about 10 times, 20, times, 30 times, 40 times, 50 times, 60 times, 70 times, 80 times, 90 times, or more, or at least about 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential, or the presence of degradative molecules. Generally, cleavage agents are more prevalent or found at higher levels or activities inside cells than in serum or blood. Examples of such degradative agents include: redox agents which are selective for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissues. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In preferred embodiments, useful candidate compounds are cleaved at least about 2, 4, 10, 20, 30, 40, 50, 60, 70, 80, 90, or about 100 times faster in the cell (or under in vitro conditions selected to mimic intracellular conditions) as compared to blood or serum (or under in vitro conditions selected to mimic extracellular conditions).

a. Redox Cleavable Linking Groups

In one embodiment, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular oligonucleotide moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In one embodiment, candidate compounds are cleaved by at most about 10% in the blood. In other embodiments, useful candidate compounds are degraded at least about 2, 4, 10, 20, 30, 40, 50, 60, 70, 80, 90, or about 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

b. Phosphate-Based Cleavable Linking Groups

In another embodiment, a cleavable linker includes a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O—P(O)(OR$^k$)—O—, —O—P(S)(OR$^k$)—O—, —O—P(S)(SR$^k$)—O—, —S—P(O)(OR$^k$)—O—, —O—P(O)(OR$^k$)—S—, —S—P(O)(OR$^k$)—S—, —O—P(S)(OR$^k$)—S—, —S—P(S)(OR$^k$)—O—, —O—P(O)(R$^k$)—O—, —O—P(S)(R$^k$)—O—, —S—P(O)(R$^k$)—O—, —S—P(S)(R$^k$)—O—, —S—P(O)(R$^k$)—S—, —O—P(S)(R$^k$)—S—. These candidates can be evaluated using methods analogous to those described above.

c. Acid Cleavable Linking Groups. In another embodiment, a cleavable linker includes an acid cleavable linking group. An acid cleavable linking group is a linking group that is cleaved under acidic conditions. In preferred embodiments acid cleavable linking groups are cleaved in an acidic environment with a pH of about 6.5 or lower (e.g., about 6.0, 5.75, 5.5, 5.25, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

d. Ester-Based Linking Groups

In another embodiment, a cleavable linker includes an ester-based cleavable linking group. An ester-based cleavable linking group is cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

e. Peptide-Based Cleaving Groups

In yet another embodiment, a cleavable linker includes a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene, or alkynelene. A peptide bond is a special type of amide bond formed between amino acids to yield peptides and proteins. The peptide-based cleavage group is generally limited to the peptide bond (i.e., the amide bond) formed between amino acids yielding peptides and proteins and does not include the entire amide functional group. Peptide-based cleavable linking groups have the general formula —NHCHRAC(O)NHCHRBC(O)—, where RA and RB are the R groups of the two adjacent amino acids. These candidates can be evaluated using methods analogous to those described above.

In one embodiment, an oligonucleotide of the invention is conjugated to a carbohydrate through a linker. Linkers include bivalent and trivalent branched linker groups. Exemplary oligonucleotide carbohydrate conjugates with linkers of the compositions and methods of the invention include, but are not limited to, those described in formulas 24-35 of PCT Publication No. WO 2018/195165.

Representative U.S. patents that teach the preparation of oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; 8,106,022, the entire contents of each of which are hereby incorporated herein by reference.

In certain instances, the nucleotides of an oligonucleotide can be modified by a non-ligand group. A number of non-ligand molecules have been conjugated to oligonucleotides in order to enhance the activity, cellular distribution, or cellular uptake of the oligonucleotide, and procedures for performing such conjugations are available in the scientific literature. Such non-ligand moieties have included lipid moieties, such as cholesterol (Kubo, T. et al., Biochem. Biophys. Res. Comm, 2007, 365(1):54-61; Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-S-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such oligonucleotide conjugates have been listed above. Typical conjugation protocols involve the synthesis of an oligonucleotide bearing an amino linker at one or more positions of the sequence. The amino group is then reacted with the molecule being conjugated using appropriate coupling or activating reagents. The conjugation reaction can be performed either with the oligonucleotide still bound to the solid support or following cleavage of the oligonucleotide, in solution phase. Purification of the oligonucleotide conjugate by HPLC typically affords the pure conjugate.

III. Pharmaceutical Uses

The oligonucleotides of the invention may be used to treat any disorder which may be treated through deamination of an adenosine. For example, any disorder which is caused by a guanosine to adenosine mutation, the introduction of a premature stop codon, or expression of an undesired protein. In some embodiments, the oligonucleotides of the invention, when administered to a subject, can result in correction of a guanosine to adenosine mutation. In some embodiments, the oligonucleotides of the invention can result in turning off of a premature stop codon so that a desired protein is expressed. In some embodiments, the oligonucleotides of the invention can result in inhibition of expression of an undesired protein.

Particularly interesting target adenosines for editing using oligonucleotides according to the invention are those that are part of codons for amino acid residues that define key functions, or characteristics, such as catalytic sites, binding sites for other proteins, binding by substrates, localization domains, for co- or post-translational modification, such as glycosylation, hydroxylation, myristoylation, and protein cleavage by proteases (to mature the protein and/or as part of the intracellular routing).

A host of genetic diseases are caused by G-to-A mutations, and these are possible diseases to be treated by oligonucleotides of the invention because adenosine deamination at the mutated target adenosine will reverse the mutation to wild-type. However, reversal to wild-type may not always be necessary to obtain a beneficial effect. Modification of an A to a G in a target may also be beneficial if the wild-type nucleotide is other than a G. In certain circumstances this may be predicted to be the case, in others this may require some testing. In certain circumstances, the modification from an A in a target RNA to a G where the wild-type is not a G may be silent (not translated into a different amino acid), or otherwise non-consequential (for example an amino acid is substituted but it constitutes a conservative substitution that does not disrupt protein structure and function), or the amino acid is part of a functional domain that has a certain robustness for change. If the A-to-G transition brought about by editing in accordance with the invention is in a non-coding RNA, or a non-coding part of an RNA, the consequence may also be inconsequential or less severe than the original mutation. Those of ordinary skill in the art will understand that the applicability of the current invention is very wide and is not even limited to preventing or treating disease. The invention may also be used to modify transcripts to study the effect thereof, even if, or particularly when, such modification induces a diseased state, for example in a cell or a non-human animal model.

Examples of genetic diseases that can be prevented and/or treated with oligonucleotides according to the invention are any disease where the modification of one or more adenosines in a target RNA will bring about a (potentially) beneficial change.

The invention is not limited to correcting mutations, as it may instead be useful to change a wildtype sequence into a mutated sequence by applying oligonucleotides according to the invention. One example where it may be advantageous to modify a wild-type adenosine is to bring about skipping of an exon, for example by modifying an adenosine that happens to be a branch site required for splicing of said exon. Another example is where the adenosine defines or is part of a recognition sequence for protein binding or is involved in secondary structure defining the stability of the RNA. As noted above, therefore, the invention can be used to provide research tools for diseases, to introduce new mutations which are less deleterious than an existing mutation.

Deamination of an adenosine using the oligonucleotides disclosed herein includes any level of adenosine deamination, e.g., at least 1 deaminated adenosine within a target sequence (e.g., at least, 1, 2, 3, or more deaminated adenosines in a target sequence).

Adenosine deamination may be assessed by a decrease in an absolute or relative level of adenosines within a target sequence compared with a control level. The control level may be any type of control level that is utilized in the art, e.g., pre-dose baseline level, or a level determined from a similar subject, cell, or sample that is untreated or treated with a control (such as, e.g., buffer only control or inactive agent control).

Because the enzymatic activity of ADAR converts adenosines to inosines, adenosine deamination can alternatively be assessed by an increase in an absolute or relative level of inosines within a target sequence compared with a control level. Similarly, the control level may be any type of control level that is utilized in the art, e.g., pre-dose baseline level, or a level determined from a similar subject, cell, or sample that is untreated or treated with a control (such as, e.g., buffer only control or inactive agent control).

The levels of adenosines and/or inosines within a target sequence can be assessed using any of the methods known in the art for determining the nucleotide composition of a polynucleotide sequence. For example, the relative or absolute levels of adenosines or inosines within a target sequence can be assessed using nucleic acid sequencing technologies including but not limited to Sanger sequencing methods, Next Generation Sequencing (NGS; e.g., pyrosequencing, sequencing by reversible terminator chemistry, sequencing by ligation, and real-time sequencing) such as those offered on commercially available platforms (e.g., Illumina, Qiagen, Pacific Biosciences, Thermo Fisher, Roche, and Oxford Nanopore Technologies). Clonal amplification of target sequences for NGS may be performed using real-time polymerase chain reaction (also known as qPCR) on commercially available platforms from Applied Biosystems, Roche, Stratagene, Cepheid, Eppendorf, or Bio-Rad Laboratories. Additionally, emulsion PCR methods can be used for amplification of target sequences using commercially available platforms such as Droplet Digital PCR by Bio-Rad Laboratories.

In certain embodiments, surrogate markers can be used to detect adenosine deamination within a target sequence. For example, effective treatment of a subject having a genetic disorder involving G-to-A mutations with an oligonucleotide of the present disclosure, as demonstrated by an acceptable diagnostic and monitoring criteria can be understood to demonstrate a clinically relevant adenosine deamination. In certain embodiments, the methods include a clinically relevant adenosine deamination, e.g., as demonstrated by a clinically relevant outcome after treatment of a subject with an oligonucleotide of the present disclosure.

Adenosine deamination in a gene of interest may be manifested by an increase or decrease in the levels of mRNA expressed by a first cell or group of cells (such cells may be present, for example, in a sample derived from a subject) in which a gene of interest is transcribed and which has or have been treated (e.g., by contacting the cell or cells with an oligonucleotide of the present disclosure, or by administering an oligonucleotide of the invention to a subject in which the cells are or were present) such that the expression of the gene of interest is increased or decreased, as compared to a second cell or group of cells substantially identical to the first cell or group of cells but which has not or have not been so treated (control cell(s) not treated with an oligonucleotide or not treated with an oligonucleotide targeted to the gene of interest). The degree of increase or decrease in the levels of mRNA of a gene of interest may be expressed in terms of:

$$\frac{(mRNA \text{ in control cells}) - (mRNA \text{ in treated cells})}{(mRNA \text{ in control cells})} \times 100\%$$

In other embodiments, change in the levels of a gene may be assessed in terms of a reduction of a parameter that is functionally linked to the expression of a gene of interest, e.g., protein expression of the gene of interest or signaling downstream of the protein. A change in the levels of the gene of interest may be determined in any cell expressing the gene of interest, either endogenous or heterologous from an expression construct, and by any assay known in the art.

A change in the level of expression of a gene of interest may be manifested by an increase or decrease in the level of the protein produced by the gene of interest that is expressed by a cell or group of cells (e.g., the level of protein expressed in a sample derived from a subject). As explained above, for the assessment of mRNA suppression, the change in the level of protein expression in a treated cell or group of cells may similarly be expressed as a percentage of the level of protein in a control cell or group of cells.

A control cell or group of cells that may be used to assess the change in the expression of a 3 gene of interest includes a cell or group of cells that has not yet been contacted with an oligonucleotide of the present disclosure. For example, the control cell or group of cells may be derived from an individual subject (e.g., a human or animal subject) prior to treatment of the subject with an oligonucleotide.

The level of mRNA of a gene of interest that is expressed by a cell or group of cells may be determined using any method known in the art for assessing mRNA expression. In one embodiment, the level of expression of a gene of interest in a sample is determined by detecting a transcribed polynucleotide, or portion thereof, e.g., mRNA of the gene of interest. RNA may be extracted from cells using RNA extraction techniques including, for example, using acid phenol/guanidine isothiocyanate extraction (RNAzol B; Biogenesis), RNEASY™ RNA preparation kits (Qiagen) or PAXgene (PreAnalytix, Switzerland). Typical assay formats utilizing ribonucleic acid hybridization include nuclear run-on assays, RT-PCR, RNase protection assays, northern blotting, in situ hybridization, and microarray analysis. Circulating mRNA of the gene of interest may be detected using methods the described in PCT Publication WO2012/177906, the entire contents of which are hereby incorporated herein by reference. In some embodiments, the level of expression of the gene of interest is determined using a nucleic acid probe. The term "probe," as used herein, refers to any molecule that is capable of selectively binding to a specific sequence, e.g. to an mRNA or polypeptide. Probes can be synthesized by one of skill in the art or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or northern analyses, polymerase chain reaction (PCR) analyses, and probe arrays. One method for the determination of mRNA levels involves contacting the isolated mRNA with a nucleic acid molecule (probe) that can hybridize to the mRNA of a gene of interest. In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an AFFYMETRIX gene chip array. A skilled artisan can readily adapt known mRNA detection methods for use in determining the level of mRNA of a gene of interest.

An alternative method for determining the level of expression of a gene of interest in a sample involves the process of nucleic acid amplification and/or reverse transcriptase (to prepare cDNA) of for example mRNA in the sample, e.g., by RT-PCR (the experimental embodiment set forth in Mullis, 1987, U.S. Pat. No. 4,683,202), ligase chain reaction (Barany (1991) Proc. Natl. Acad. Sci. USA 88:189-193), self-sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, the level of expression of a gene of interest is determined by quantitative fluorogenic RT-PCR (i.e., the TAQMAN™ System) or the DUAL-GLO® Luciferase assay.

The expression levels of mRNA of a gene of interest may be monitored using a membrane blot (such as used in hybridization analysis such as northern, Southern, dot, and the like), or microwells, sample tubes, gels, beads or fibers (or any solid support including bound nucleic acids). See U.S. Pat. Nos. 5,770,722; 5,874,219; 5,744,305; 5,677,195; and 5,445,934, which are incorporated herein by reference. The determination of gene expression level may also include using nucleic acid probes in solution.

In some embodiments, the level of mRNA expression is assessed using branched DNA (bDNA) assays or real time PCR (qPCR). The use of this PCR method is described and exemplified in the Examples presented herein. Such methods can also be used for the detection of nucleic acids of the gene of interest.

The level of protein produced by the expression of a gene of interest may be determined using any method known in the art for the measurement of protein levels. Such methods include, for example, electrophoresis, capillary electrophoresis, high performance liquid chromatography (HPLC), thin layer chromatography (TLC), hyperdiffusion chromatography, fluid or gel precipitin reactions, absorption spectroscopy, a colorimetric assays, spectrophotometric assays, flow cytometry, immunodiffusion (single or double), immunoelectrophoresis, western blotting, radioimmunoassay (RIA), enzyme-linked immunosorbent assays (ELISAs), immunofluorescent assays, electrochemiluminescence assays, and the like. Such assays can also be used for the detection of proteins indicative of the presence or replication of proteins produced by the gene of interest. Additionally, the above assays may be used to report a change in the mRNA sequence of interest that results in the recovery or change in protein function thereby providing a therapeutic effect and benefit to the subject, treating a disorder in a subject, and/or reducing of symptoms of a disorder in the subject.

In some embodiments of the methods of the invention, the oligonucleotide of the present disclosure is administered to a subject such that the oligonucleotide is delivered to a specific site within the subject. The change in the expression of the gene of interest may be assessed using measurements of the level or change in the level of mRNA or protein produced by the gene of interest in a sample derived from a specific site within the subject.

In other embodiments, the oligonucleotide is administered in an amount and for a time effective to result in one of (or more, e.g., two or more, three or more, four or more of): (a) decrease the number of adenosines within a target sequence of the gene of interest, (b) delayed onset of the disorder, (c) increased survival of subject, (d) increased progression free survival of a subject, (e) recovery or change in protein function, and (f) reduction in symptoms.

Treating disorders associated with G-to-A mutations can also result in a decrease in the mortality rate of a population of treated subjects in comparison to an untreated population. For example, the mortality rate is decreased by more than 2% (e.g., more than 5%, 10%, or 25%). A decrease in the mortality rate of a population of treated subjects may be measured by any reproducible means, for example, by calculating for a population the average number of disease-related deaths per unit time following initiation of treatment with a compound or pharmaceutically acceptable salt of a compound described herein. A decrease in the mortality rate of a population may also be measured, for example, by calculating for a population the average number of disease-related deaths per unit time following completion of a first round of treatment with a compound or pharmaceutically acceptable salt of a compound described herein.

A. Delivery of Oligonucleotides

The delivery of an oligonucleotide of the invention to a cell e.g., a cell within a subject, such as a human subject (e.g., a subject in need thereof, such as a subject having a disorder) can be achieved in a number of different ways. For example, delivery may be performed by contacting a cell with an oligonucleotide of the invention either in vitro or in vivo. In vivo delivery may also be performed directly by administering a composition including an oligonucleotide to a subject. Alternatively, in vivo delivery may be performed indirectly by administering one or more vectors that encode and direct the expression of the oligonucleotide. Combinations of in vitro and in vivo methods of contacting a cell are also possible. Contacting a cell may be direct or indirect, as discussed above. Furthermore, contacting a cell may be accomplished via a targeting ligand, including any ligand described herein or known in the art. In some embodiments, the targeting ligand is a carbohydrate moiety, e.g., a GalNAc$_3$ ligand, or any other ligand that directs the oligonucleotide to a site of interest. Cells can include those of the central nervous system, or muscle cells. These alternatives are discussed further below.

Contacting of a cell with an oligonucleotide may be done in vitro or in vivo. can be adapted for use with an oligonucleotide of the invention (see e.g., Akhtar S. and Julian R L., (1992) Trends Cell. Biol. 2(5):139-144 and WO94/02595, which are incorporated herein by reference in their entireties). For in vivo delivery, factors to consider in order to deliver an oligonucleotide molecule include, for example, biological stability of the delivered molecule, prevention of non-specific effects, and accumulation of the delivered molecule in the target tissue. The non-specific effects of an oligonucleotide can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the oligonucleotide molecule to be administered.

For administering an oligonucleotide systemically for the treatment of a disease, the oligonucleotide can include alternative nucleobases, alternative sugar moieties, and/or alternative internucleoside linkages, or alternatively delivered using a drug delivery system; both methods act to prevent the rapid degradation of the oligonucleotide by endo- and exo-nucleases in vivo. Modification of the oligonucleotide or the pharmaceutical carrier can also permit targeting of the oligonucleotide composition to the target tissue and avoid undesirable off-target effects. Oligonucleotide molecules can be modified by chemical conjugation to lipophilic groups such as cholesterol to enhance cellular uptake and prevent degradation. In an alternative embodiment, the oligonucleotide can be delivered using drug delivery systems such as a nanoparticle, a lipid nanoparticle, a polyplex nanoparticle, a lipoplex nanoparticle, a dendrimer, a polymer, liposomes, or a cationic delivery system. Positively charged cationic delivery systems facilitate binding of an oligonucleotide molecule (negatively charged) and also enhance interactions at the negatively charged cell membrane to permit efficient uptake of an oligonucleotide by the cell. Cationic lipids, dendrimers, or polymers can either be bound to an oligonucleotide, or induced to form a vesicle or micelle that encases an oligonucleotide. The formation of vesicles or micelles further prevents degradation of the oligonucleotide when administered systemically. In general, any methods of delivery of nucleic acids known in the art may be adaptable to the delivery of the oligonucleotides of the invention. Methods for making and administering cationic oligonucleotide complexes are well within the abilities of one skilled in the art (see e.g., Sorensen, D R., et al. (2003) J. Mol. Biol 327:761-766; Verma, U N. et al., (2003) Clin. Cancer Res. 9:1291-1300; Arnold, A S et al., (2007) J. Hypertens. 25:197-205, which are incorporated herein by reference in their entirety). Some non-limiting examples of drug delivery systems useful for systemic delivery of oligonucleotides include DOTAP (Sorensen, D R., et al (2003), supra; Verma, U N. et al., (2003), supra), Oligofectamine, "solid nucleic acid lipid particles" (Zimmermann, T S. et al., (2006) Nature 441:111-114), cardiolipin (Chien, P Y. et al., (2005) Cancer Gene Ther. 12:321-328; Pal, A. et al., (2005) Int J. Oncol. 26:1087-1091), polyethyleneimine (Bonnet M E. et al., (2008) Pharm. Res. August 16 Epub ahead of print; Aigner, A. (2006) J. Biomed. Biotechnol. 71659), Arg-Gly-Asp (RGD) peptides (Liu, S. (2006) Mol. Pharm. 3:472-487), and polyamidoamines (Tomalia, D A. et al., (2007) Biochem. Soc. Trans. 35:61-67; Yoo, H. et al., (1999) Pharm. Res. 16:1799-1804). In some embodiments, an oligonucleotide forms a complex with cyclodextrin for systemic administration. Methods for administration and pharmaceutical compositions of oligonucleotides and cyclodextrins can be found in U.S. Pat. No. 7,427,605, which is herein incorporated by reference in its entirety. In some embodiments the oligonucleotides of the invention are delivered by polyplex or lipoplex nanoparticles. Methods for administration and pharmaceutical compositions of oligonucleotides and polyplex nanoparticles and lipoplex nanoparticles can be found in U.S. Patent Application Nos. 2017/0121454; 2016/0369269; 2016/0279256; 2016/0251478; 2016/0230189; 2015/0335764; 2015/0307554; 2015/0174549; 2014/0342003; 2014/0135376; and 2013/0317086, which are herein incorporated by reference in their entirety.

i. Membranous Molecular Assembly Delivery Methods

Oligonucleotides of the invention can also be delivered using a variety of membranous molecular assembly delivery methods including polymeric, biodegradable microparticle, or microcapsule delivery devices known in the art. For example, a colloidal dispersion system may be used for targeted delivery an oligonucleotide agent described herein. Colloidal dispersion systems include macromolecule complexes, nanocapsules, microspheres, beads, and lipid-based systems including oil-in-water emulsions, micelles, mixed micelles, and liposomes. Liposomes are artificial membrane vesicles that are useful as delivery vehicles in vitro and in vivo. It has been shown that large unilamellar vesicles (LUV), which range in size from 0.2-4.0 μm can encapsulate a substantial percentage of an aqueous buffer containing large macromolecules. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the oligonucleotide are delivered into the cell where the oligonucleotide can specifically bind to a target RNA and can mediate RNase H-mediated gene silencing. In some cases, the liposomes are also specifically targeted, e.g., to direct the oligonucleotide to particular cell types. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

A liposome containing an oligonucleotide can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The oligonucleotide preparation is then added to the micelles that include the lipid component. The cationic groups on the lipid interact with the oligonucleotide and condense around the oligonucleotide to form a liposome. After condensation, the detergent is removed, e.g., by dialysis, to yield a liposomal preparation of oligonucleotide.

If necessary, a carrier compound that assists in condensation can be added during the condensation reaction, e.g., by controlled addition. For example, the carrier compound can be a polymer other than a nucleic acid (e.g., spermine or spermidine). The pH can also be adjusted to favor condensation.

Methods for producing stable polynucleotide delivery vehicles, which incorporate a polynucleotide/cationic lipid complex as a structural component of the delivery vehicle, are further described in, e.g., WO 96/37194, the entire contents of which are incorporated herein by reference. Liposome formation can also include one or more aspects of exemplary methods described in Feigner, P. L. et al., (1987) Proc. Natl. Acad. Sci. USA 8:7413-7417; U.S. Pat. Nos. 4,897,355; 5,171,678; Bangham et al., (1965) M. Mol. Biol. 23:238; Olson et al., (1979) Biochim. Biophys. Acta 557:9; Szoka et al., (1978) Proc. Natl. Acad. Sci. 75: 4194; Mayhew et al., (1984) Biochim. Biophys. Acta 775:169; Kim et al., (1983) Biochim. Biophys. Acta 728:339; and Fukunaga et al., (1984) Endocrinol. 115:757. Commonly used techniques for preparing lipid aggregates of appropriate size for use as delivery vehicles include sonication and freeze-thaw plus extrusion (see, e.g., Mayer et al., (1986) Biochim. Biophys. Acta 858:161. Microfluidization can be used when consistently small (50 to 200 nm) and relatively uniform aggregates are desired (Mayhew et al., (1984) Biochim. Biophys. Acta 775:169. These methods are readily adapted to packaging oligonucleotide preparations into liposomes.

Liposomes fall into two broad classes. Cationic liposomes are positively charged liposomes which interact with the negatively charged nucleic acid molecules to form a stable complex. The positively charged nucleic acid/liposome complex binds to the negatively charged cell surface and is internalized in an endosome. Due to the acidic pH within the endosome, the liposomes are ruptured, releasing their contents into the cell cytoplasm (Wang et al. (1987) Biochem. Biophys. Res. Commun., 147:980-985).

Liposomes, which are pH-sensitive or negatively charged, entrap nucleic acids rather than complex with them. Since both the nucleic acid and the lipid are similarly charged, repulsion rather than complex formation occurs. Nevertheless, some nucleic acid is entrapped within the aqueous interior of these liposomes. pH sensitive liposomes have been used to deliver nucleic acids encoding the thymidine kinase gene to cell monolayers in culture. Expression of the exogenous gene was detected in the target cells (Zhou et al. (1992) Journal of Controlled Release, 19:269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Examples of other methods to introduce liposomes into cells in vitro and in vivo include U.S. Pat. Nos. 5,283,185; 5,171,678; WO 94/00569; WO 93/24640; WO 91/16024; Feigner, (1994) J. Biol. Chem. 269:2550; Nabel, (1993) Proc. Natl. Acad. Sci. 90:11307; Nabel, (1992) Human Gene Ther. 3:649; Gershon, (1993) Biochem. 32:7143; and Strauss, (1992) EMBO J. 11:417.

Non-ionic liposomal systems have also been examined to determine their utility in the delivery of drugs to the skin, in particular systems including non-ionic surfactant and cholesterol. Non-ionic liposomal formulations including NOVASOME™ I (glyceryl dilaurate/cholesterol/polyoxyethylene-10-stearyl ether) and NOVASOME™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporine A into different layers of the skin (Hu et al., (1994) S.T.P. Pharma. Sci., 4(6):466).

Liposomes may also be sterically stabilized liposomes, including one or more specialized lipids that result in enhanced circulation lifetimes relative to liposomes lacking such specialized lipids. Examples of sterically stabilized liposomes are those in which part of the vesicle-forming lipid portion of the liposome (A) includes one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., (1987) FEBS Letters, 223:42; Wu et al., (1993) Cancer Research, 53:3765).

Various liposomes including one or more glycolipids are known in the art. Papahadjopoulos et al. (Ann. N.Y. Acad. Sci., (1987), 507:64) reported the ability of monosialoganglio side $G_{M1}$, galactocerebroside sulfate, and phosphatidylinositol to improve blood half-lives of liposomes. These findings were expounded upon by Gabizon et al. (Proc. Natl. Acad. Sci. U.S.A., (1988), 85:6949). U.S. Pat. No. 4,837,028 and WO 88/04924, both to Allen et al., disclose liposomes including (1) sphingomyelin and (2) the ganglioside $G_{M1}$ or a galactocerebroside sulfate ester. U.S. Pat. No. 5,543,152 (Webb et al.) discloses liposomes including sphingomyelin. Liposomes including 1,2-sn-dimyristoylphosphatidylcholine are disclosed in WO 97/13499 (Lim et al).

In one embodiment, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver oligonucleotides to macrophages.

Further advantages of liposomes include: liposomes obtained from natural phospholipids are biocompatible and biodegradable; liposomes can incorporate a wide range of water and lipid soluble drugs; liposomes can protect encapsulated oligonucleotides in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of oligonucleotides (see, e.g., Feigner, P. L. et al., (1987) Proc. Natl. Acad. Sci. USA 8:7413-7417, and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. LIPOFECTIN™ Bethesda Research Laboratories, Gaithersburg, Md.) is an effective agent for the delivery of highly anionic nucleic acids into living tissue culture cells that include positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis (oleoyloxy)-3,3-(trimethylammonia)propane ("DOTAP") (Boehringer Mannheim, Indianapolis, Ind.) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (TRANSFECTAM™, Promega, Madison, Wis.) and dipalmitoylphosphatidylethanolamine 5-carboxyspermylamide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., (1991) Biochim. Biophys. Res. Commun. 179:280). Lipopolylysine, made by conjugating polylysine to DOPE, has been reported to be effective for transfection in the presence of serum (Zhou, X. et al., (1991) Biochim. Biophys. Acta 1065:8). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, Calif.) and Lipofectamine (DOSPA) (Life Technology, Inc., Gaithersburg, Md.). Other cationic lipids suitable for the delivery of oligonucleotides are described in WO 98/39359 and WO 96/37194.

Liposomal formulations are particularly suited for topical administration, liposomes present several advantages over other formulations. Such advantages include reduced side effects related to high systemic absorption of the administered drug, increased accumulation of the administered drug at the desired target, and the ability to administer oligonucleotides into the skin. In some implementations, liposomes are used for delivering oligonucleotides to epidermal cells and also to enhance the penetration of oligonucleotides into dermal tissues, e.g., into skin. For example, the liposomes can be applied topically. Topical delivery of drugs formulated as liposomes to the skin has been documented (see, e.g., Weiner et al., (1992) Journal of Drug Targeting, vol. 2, 405-410 and du Plessis et al., (1992) Antiviral Research, 18:259-265; Mannino, R. J. and Fould-Fogerite, S., (1998) Biotechniques 6:682-690; Itani, T. et al., (1987) Gene 56:267-276; Nicolau, C. et al. (1987) Meth. Enzymol. 149:157-176; Straubinger, R. M. and Papahadjopoulos, D. (1983) Meth. Enzymol. 101:512-527; Wang, C. Y. and Huang, L., (1987) Proc. Natl. Acad. Sci. USA 84:7851-7855).

Non-ionic liposomal systems have also been examined to determine their utility in the delivery of drugs to the skin, in particular systems including non-ionic surfactant and cholesterol. Non-ionic liposomal formulations including Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin. Such formulations with oligonucleotide are useful for treating a dermatological disorder.

The targeting of liposomes is also possible based on, for example, organ-specificity, cell-specificity, and organelle-specificity and is known in the art. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Additional methods are known in the art and are described, for example in U.S. Patent Application Publication No. 20060058255, the linking groups of which are herein incorporated by reference.

Liposomes that include oligonucleotides can be made highly deformable. Such deformability can enable the liposomes to penetrate through pore that are smaller than the average radius of the liposome. For example, transfersomes are yet another type of liposomes, and are highly deformable lipid aggregates which are attractive candidates for drug delivery vehicles. Transfersomes can be described as lipid droplets which are so highly deformable that they are easily able to penetrate through pores which are smaller than the droplet. Transfersomes can be made by adding surface edge activators, usually surfactants, to a standard liposomal composition. Transfersomes that include oligonucleotides can be delivered, for example, subcutaneously by infection in order to deliver oligonucleotides to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transfersomes can be self-optimizing (adaptive to the shape of pores, e.g., in the skin), self-repairing, and can frequently reach their targets without fragmenting, and often self-loading. Transfersomes have been used to deliver serum albumin to the skin. The transfersome-mediated delivery of serum albumin has been shown to be as effective as subcutaneous injection of a solution containing serum albumin.

Other formulations amenable to the present invention are described in U.S. provisional application Ser. No. 61/018,616, filed Jan. 2, 2008; 61/018,611, filed Jan. 2, 2008; 61/039,748, filed Mar. 26, 2008; 61/047,087, filed Apr. 22, 2008 and 61/051,528, filed May 8, 2008. PCT application No. PCT/US2007/080331, filed Oct. 3, 2007 also describes formulations that are amenable to the present invention.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general, their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines, and phosphatides.

The use of surfactants in drug products, formulations and in emulsions has been reviewed (Rieger, in Pharmaceutical Dosage Forms, Marcel Dekker, Inc., New York, N.Y., 1988, p. 285).

The oligonucleotide for use in the methods of the invention can also be provided as micellar formulations. Micelles are a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

ii. Lipid Nanoparticle-Based Delivery Methods

Oligonucleotides of in the invention may be fully encapsulated in a lipid formulation, e.g., a lipid nanoparticle (LNP), or other nucleic acid-lipid particles. LNPs are extremely useful for systemic applications, as they exhibit extended circulation lifetimes following intravenous (i.v.) injection and accumulate at distal sites (e.g., sites physically separated from the administration site). LNPs include "pSPLP," which include an encapsulated condensing agent-nucleic acid complex as set forth in PCT Publication No.

WO 00/03683. The particles of the present invention typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586, 410; 6,815,432; U.S. Publication No. 2010/0324120 and PCT Publication No. WO 96/40964.

In one embodiment, the lipid to drug ratio (mass/mass ratio) (e.g., lipid to oligonucleotide ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1. Ranges intermediate to the above recited ranges are also contemplated to be part of the invention.

Non-limiting examples of cationic lipid include N,N-dioleyl-N,N-dimethylammonium chloride (DODAC), N,N-distearyl-N,N-dimethylammonium bromide (DDAB), N-(I-(2,3-dioleoyloxy)propyl)-N,N,N-trimethylammonium chloride (DOTAP), N-(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)—N,N-dimethyl-2,2-di((9Z,12Z)-octadeca-9,12-dienyetetrahydro-3aH-cyclopenta[d][1,3]dioxol-5-amine (ALN100), (6Z,9Z,28Z,31Z)-heptatriaconta-6,9,28,31-tetraen-19-yl4-(dimethylamino)butanoate (MC3), 1,1'-(2-(4-(24(2-(bis(2-hydroxydodecyl)amino)ethyl)(2-hydroxydodecyl)amino)ethyl)piperazin-1-yeethylazanediyedidodecan-2-ol (Tech G1), or a mixture thereof. The cationic lipid can include, for example, from about 20 mol % to about 50 mol % or about 40 mol % of the total lipid present in the particle.

The ionizable/non-cationic lipid can be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid can be, for example, from about 5 mol % to about 90 mol %, about 10 mol %, or about 58 mol % if cholesterol is included, of the total lipid present in the particle.

The conjugated lipid that inhibits aggregation of particles can be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate can be, for example, a PEG-dilauryloxypropyl ($Ci_2$), a PEG-dimyristyloxypropyl ($Ci_4$), a PEG-dipalmityloxypropyl ($Ci_6$), or a PEG-distearyloxypropyl ($Ci_8$). The conjugated lipid that prevents aggregation of particles can be, for example, from 0 mol % to about 20 mol % or about 2 mol % of the total lipid present in the particle.

In some embodiments, the nucleic acid-lipid particle further includes cholesterol at, e.g., about 10 mol % to about 60 mol % or about 50 mol % of the total lipid present in the particle.

B. Combination Therapies

A method of the invention can be used alone or in combination with an additional therapeutic agent, e.g., other agents that treat the same disorder or symptoms associated therewith, or in combination with other types of therapies to the disorder. In combination treatments, the dosages of one or more of the therapeutic compounds may be reduced from standard dosages when administered alone. For example, doses may be determined empirically from drug combinations and permutations or may be deduced by isobolographic analysis (e.g., Black et al., Neurology 65:S3-S6 (2005)). In this case, dosages of the compounds when combined should provide a therapeutic effect.

In some embodiments, the second therapeutic agent is a chemotherapeutic agent (e.g., a cytotoxic agent or other chemical compound useful in the treatment of a disorder).

The second agent may be a therapeutic agent which is a non-drug treatment. For example, the second therapeutic agent is physical therapy.

In any of the combination embodiments described herein, the first and second therapeutic agents are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

IV. Pharmaceutical Compositions

The oligonucleotides described herein are preferably formulated into pharmaceutical compositions for administration to human subjects in a biologically compatible form suitable for administration in vivo.

The compounds described herein may be used in the form of the free base, in the form of salts, solvates, and as prodrugs. All forms are within the methods described herein. In accordance with the methods of the invention, the described compounds or salts, solvates, or prodrugs thereof may be administered to a patient in a variety of forms depending on the selected route of administration, as will be understood by those skilled in the art. The compounds described herein may be administered, for example, by oral, parenteral, intrathecal, intracerebroventricular, intraparenchymal, buccal, sublingual, nasal, rectal, patch, pump, intratumoral, or transdermal administration and the pharmaceutical compositions formulated accordingly. Parenteral administration includes intravenous, intraperitoneal, subcutaneous, intramuscular, transepithelial, nasal, intrapulmonary, intrathecal, intracerebroventricular, intraparenchymal, rectal, and topical modes of administration. Parenteral administration may be by continuous infusion over a selected period of time.

A compound described herein may be orally administered, for example, with an inert diluent or with an assimilable edible carrier, or it may be enclosed in hard- or soft-shell gelatin capsules, or it may be compressed into tablets, or it may be incorporated directly with the food of the diet. For oral therapeutic administration, a compound described herein may be incorporated with an excipient and used in the form of ingestible tablets, buccal tablets, troches, capsules, elixirs, suspensions, syrups, and wafers. A compound described herein may also be administered parenterally. Solutions of a compound described herein can be prepared in water suitably mixed with a surfactant, such as hydroxypropylcellulose. Dispersions can also be prepared in glycerol, liquid polyethylene glycols, DMSO, and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2012, 22nd ed.) and in The United States Pharmacopeia: The National Formulary (USP 41 NF 36), published in 2018. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe. Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form includes an aerosol dispenser, it will contain a propellant, which can be a compressed gas, such as compressed air or an organic propellant, such as fluorochlorohydrocarbon. The aerosol dosage forms can also take the form of a pump-atomizer. Compositions suitable for buccal or sublingual administration include tablets, lozenges, and pastilles, where the active ingredient is formulated with a carrier, such as sugar, acacia, tragacanth, gelatin, and glycerine. Compositions for rectal administration are conveniently in the form of suppositories containing a conventional suppository base, such as cocoa butter. A compound described herein may be administered intratumorally, for example, as an intratumoral injection. Intratumoral injection is injection directly into the tumor vasculature and is specifically contemplated for discrete, solid, accessible tumors. Local, regional, or systemic administration also may be appropriate. A compound described herein may advantageously be contacted by administering an injection or multiple injections to the tumor, spaced for example, at approximately, 1 cm intervals. In the case of surgical intervention, the present invention may be used preoperatively, such as to render an inoperable tumor subject to resection. Continuous administration also may be applied where appropriate, for example, by implanting a catheter into a tumor or into tumor vasculature.

The compounds described herein may be administered to an animal, e.g., a human, alone or in combination with pharmaceutically acceptable carriers, as noted herein, the proportion of which is determined by the solubility and chemical nature of the compound, chosen route of administration, and standard pharmaceutical practice.

V. Dosages

The dosage of the compositions (e.g., a composition including an oligonucleotide) described herein, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compositions described herein may be administered initially in a suitable dosage that may be adjusted as required, depending on the clinical response. In some embodiments, the dosage of a composition (e.g., a composition including an oligonucleotide) is a prophylactically or a therapeutically effective amount.

VI. Kit

The invention also features kits including (a) a pharmaceutical composition including an oligonucleotide agent that results in deamination of an adenosine in an mRNA in a cell or subject described herein, and (b) a package insert with instructions to perform any of the methods described herein. In some embodiments, the kit includes (a) a pharmaceutical composition including an oligonucleotide agent that results in deamination of an adenosine in an mRNA in a cell or subject described herein, (b) an additional therapeutic agent, and (c) a package insert with instructions to perform any of the methods described herein.

EXAMPLES

General Methods

All guide oligonucleotides were chemically synthesized on an automated RNA/DNA synthesizer using standard β-cyanoethylphosphoramidite chemistry and a universal solid support such as controlled pore glass (CPG). Phosphoramidites of N-protected GNA, FNA, and SNA were synthesized utilizing reported procedures. See Schlegel et al., (2017) J. Am. Chem Soc., 139: 8537-8546, Neuberger et al., (2008) J. Am. Chem Soc., 130: 412-413, Ogilvie et al., (1983) Can. J. Chem., 62: 241-252, Benhida et al., (1998) Tetrahedron Lett., 39: 6167-6170, Ramasamy et al., (1996) Bioorg. Med. Chem. Lett., 6: 1799-1804, and Kashida et al., (2011) Angew. Chem. Int. Ed., 50: 1285-1288. Other 5'-O-DMT-3'-phosphoramidites of RNA, 2'-O-methyl-RNA and DNA monomers, i.e., A, C, G, U, and T, were purchased from commercial sources. All oligonucleotides were synthesized by BioSpring GmbH (Frankfurt, Germany) at a 200 nmol scale. After synthesis, oligonucleotides were cleaved from the solid support, deprotected, and purified by a HPLC system using standard protocols. Oligonucleotides were desalted, dialyzed, and lyophilized. The purity of each lyophilized oligo was ≥95% as determined by analytical reversed-phase HPLC. The sequence integrity of the oligonucleotides was determined by ESI-MS.

Human ADAR2 sequence (NM_001112.4) was cloned into pcDNA3.1 plasmid under the control of the CMV promoter using BamHI and XbaI restriction sites (Quintara Bio, Berkeley, CA) and the correct insert was sequence verified. This plasmid henceforth will be denoted as ADAR2/pcDNA3.1. For editing experiments, 2 μg of ADAR2/pcDNA3.1 plasmid were transfected into $5 \times 10^6$ HEK293T cells (ATCC) using 25 μL of Lipofectamine 3000 and 24 μL of P3000 (Life Technologies) per 10 cm dish. After 4 hours, the culture media was replenished with fresh warmed media (DMEM High Glucose; Life Technologies). 12-16 hours after transfection, the transfected HEK293T cells were transfected with guide oligonucleotides such that the final concentration in the each well was 100 nM. All transfections were carried out with Lipofectamine 3000 (0.4 μL/per well) in a 96-well format, according to manufacturer's instructions. 12-16 hours after the second transfection, the cells were washed once with ice cold PBS and total mRNA isolation was performed using Dyna Beads mRNA Direct Kit (Life Technologies) adapted for KingFisher Flex Purification (Life Technologies), according to manufacturer's instructions. The samples were treated with TURBO DNase (Life Technologies) prior to elution. The resultant isolated mRNA was used for cDNA synthesis using SuperScript IV Vilo according to the manufacturer's instructions (Life Technologies). One μl of the cDNA was used as template for PCR (Platinum II Hot-Start PCR Master Mix; Life Technologies) using gene specific primers to generate an amplicon for Sanger sequencing (Table 5). Sanger sequencing was performed by Quintara Biosciences (Berkeley, CA). Adenosine to guanosine editing yields were quantified by measuring the peak height of adenosine and guanosine and dividing the guanosine peak height by the total peak height measurements of adenosine and guanosine combined.

TABLE 5

Primers Used for RT-PCR

| Name | Sequence (5' to 3') | SEQ ID NO. |
|---|---|---|
| RAB7A site 1 Forward | ACAGTATCCATTTATTATGTAATGCTTCTTAG | 75 |
| RAB7A site 1 Reverse | TGAAAGGAGCGCCTTCTAGAAC | 76 |

Example 1: Design of Guide Oligonucleotides with Novel Nucleotide Modifications Targeting Human RAB7A 3'-UTR Target (UAG)

Guide Oligonucleotide Targeting Human RAB7A (3'-UTR):

SEQ ID NO. 77
5'-CAGAGUGUUACUCAGAAUUGGGAAAUCCAGCU<u>A</u>GCGGCAGUAUUCUGUACAGUAGACACAAGAAUUAUGUACGCCUUUUAU<u>C</u>AAAGAC-3'

SEQ ID NO. 78
5'-CCCUUUAGGUCG<u>A</u>CCGCCGUCAUAAGACAUGUCAUCUGUGUUCUUAAUAC-5' (gRNA)

Shown in Table 6 below are exemplary modified guide oligonucleotides targeting human RAB7A with UAG triplet. In Table 6, A, C, G and U are ribonucleosides; underlined and bolded is the central triplet; mA, mC, mG and mU are 2'-O-methyl ribonucleosides; sgC represents (S)-(−)-GNA-C(Formula I, $N^1$=cytosine); rgC represents (R)-(+)-GNA-C (Formula II, $N^1$=cytosine); sC represents SNA-cytidine (SNA-C; Formula IV, $R^{12}$=hydrogen, $N^1$=cytosine); fxC represents FNA-cytidine (FNA-C; Formula III, $N^1$=cytosine); and asterisks indicate phosphorothioate linkages (the remaining linkages are phosphodiester linkages).

TABLE 6

Guide Oligonucleotides Targeting Human RAB7A 3'-UTR Target (UAG)

| SEQ ID NO. | Sequence with 20% 2'-O-Methyl Modifications (5' to 3') | Editing (%) | SD |
|---|---|---|---|
| 51 | 5'-mC*mA*mU*mA*mAUUCUUGUGUCUACUGUACAGAAUACUGCCG<u>CCA</u>GCUGGAUmU*mU*mC*mC*mC-3' | 22.35 | 7.42 |

TABLE 6-continued

Guide Oligonucleotides Targeting Human RAB7A 3'-UTR Target (UAG)

| | | | |
|---|---|---|---|
| 52 | 5'-mC*mA*mU*mA*mAUUCUUGUGUCUACUGUACAGAAUACUGCCGsgCCAGCUGGAUmU*mU*mC*mC*mC-3' | 20.41 | 3.01 |
| 53 | 5'-mC*mA*mU*mA*mAUUCUUGUGUCUACUGUACAGAAUACUGCCGCsgCAGCUGGAUmU*mU*mC*mC*mC-3' | 6.79 | 2.12 |
| 54 | 5'-mC*mA*mU*mA*mAUUCUUGUGUCUACUGUACAGAAUACUGCCGsgCsgCAGCUGGAUmU*mU*mC*mC*mC-3' | 8.01 | 1.53 |
| 55 | 5'-mC*mA*mU*mA*mAUUCUUGUGUCUACUGUACAGAAUACUGCCGrgCCAGCUGGAUmU*mU*mC*mC*C-3' | 15.99 | 4.27 |
| 56 | 5'-mC*mA*mU*mA*mAUUCUUGUGUCUACUGUACAGAAUACUGCCGCrgCAGCUGGAUmU*mU*mC*mC*mC-3' | 11.55 | 10.90 |
| 57 | 5'-mC*mA*mU*mA*mAUUCUUGUGUCUACUGUACAGAAUACUGCCGsCCAGCUGGAUmU*mU*mC*mC*mC-3' | 23.34 | 3.77 |
| 58 | 5'-mC*mA*mU*mA*mAUUCUUGUGUCUACUGUACAGAAUACUGCCGCsCAGCUGGAUmU*mU*mC*mC*mC-3' | 4.80 | 0.43 |
| 59 | 5'-mC*mA*mU*mA*mAUUCUUGUGUCUACUGUACAGAAUACUGCCGfxCCAGCUGGAUmU*mU*mC*mC*mC-3' | 20.52 | 3.92 |
| 60 | 5'-mC*mA*mU"mA'mAUUCUUGUGUCUACUGUACAGAAUACUGCCGCfxCAGCUGGAUmU*mU*mC*mC*mC-3' | 10.52 | 1.67 |

| Sequence with 50% 2'-O-Methyl Modifications (5' to 3') | | | |
|---|---|---|---|
| 61 | 5'-mC*mA*mU*mA*mAUUCmUmUGUGmUmCUACmUmGUACmAmGAAUmAmCUGCmCmGCCAmGmCUGmGmAUmU*mU*mC*mC*mC-3' | 17.17 | 5.26 |
| 62 | 5'-mC*mA*mU*mA*mAUUCmUmUGUGmUmCUACmUmGUACmAmGAAUmAmCUGCmCmGsgCCAmGmCUGmGmAUmU'mU*mC*mC*mC-3' | 25.76 | 6.50 |
| 63 | 5'-mC*mA*mU*mA*mAUUCmUmUGUGmUmCUACmUmGUACmAmGAAUmAmCUGCmCmGCsgCAmGmCUGmGmAUmU*mU*mC*mC*mC-3' | 3.81 | 1.08 |
| 64 | 5'-mC*mA*mU*mA*mAUUCmUmUGUGmUmCUACmUmGUACmAmGAAUmAmCUGCmCmGsgCsgCAmGmCUGmGmAUmU*mU*mC*mC*mC-3' | 9.87 | 4.58 |
| 65 | 5'-mC*mA*mU*mA*mAUUCmUmUGUGmUmCUACmUmGUACmAmGAAUmAmCUGCmCmGrgCCAmGmCUGmGmAUmU*mU*mC*mC*mC-3' | 18.31 | 5.37 |
| 66 | 5'-mC*mA*mU*mA*mAUUCmUmUGUGmUmCUACmUmGUACmAmGAAUmAmCUGCmCmGCrgCAmGmCUGmGmAUmU*mU*mC*mC*mC-3' | 5.13 | 3.11 |
| 67 | 5'-mC*mA*mU*mA*mAUUCmUmUGUGmUmCUACmUmGUACmAmGAAUmAmCUGCmCmGsCCAmGmCUGmGmAUmU*mU*mC*mC*mC-3' | 25.10 | 6.14 |
| 68 | 5'-mC*mA*mU*mA*mAUUCmUmUGUGmUmCUACmUmGUACmAmGAAUmAmCUGCmCmGCsCAmGmCUGmGmAUmU*mU*mC*mC*mC-3' | 5.05 | 2.51 |
| 69 | 5'-mC*mA*mU*mA*mAUUCmUmUGUGmUmCUACmUmGUACmAmGAAUmAmCUGCmCmGfxCCAmGmCUGmGmAUmU*mU*mC*mC*mC-3' | 22.89 | 5.83 |
| 70 | 5'-mC*mA*mU*mA*mAUUCmUmUGUGmUmCUACmUmGUACmAmGAAUmAmCUGCmCmGCfxCAmGmCUGmGmAUmU*mU*mC*mC*mC-3' | 4.90 | 2.63 |

Other Embodiments

All publications, patents, and patent applications mentioned in this specification are incorporated herein by reference in their entirety to the same extent as if each individual publication, patent, or patent application was specifically and individually indicated to be incorporated by reference in its entirety. Where a term in the present application is found to be defined differently in a document incorporated herein by reference, the definition provided herein is to serve as the definition for the term.

While the invention has been described in connection with specific embodiments thereof, it will be understood that invention is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

The invention claimed is:

1. An oligonucleotide comprising the structure:

[A$_m$]-X$^1$-X$^2$-X$^3$-[B$_n$]

wherein each of A and B is a nucleotide;

m and n are each, independently, an integer from 1 to 50;

X$^1$, X$^2$, and X$^3$ are each, independently, a nucleotide, wherein at least one of X$^1$, X$^2$, or X$^3$ has the structure of any one of Formula I-VI:

Formula I

Formula II

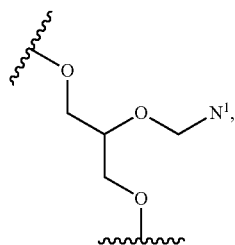

Formula III

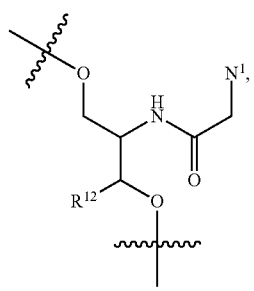

Formula IV

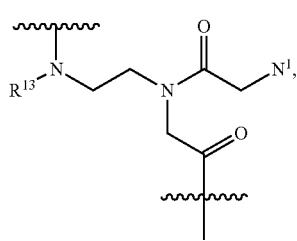

Formula V

-continued

Formula VI

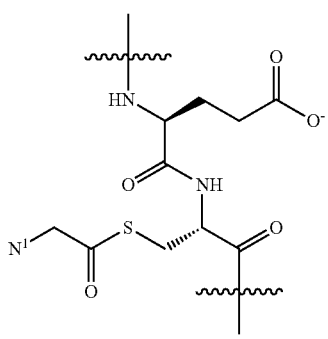

wherein N¹ is hydrogen or a nucleobase;
$R^{12}$ is hydrogen, hydroxy, halogen, $C_1$-$C_6$ alkyl, $C_1$-$C_6$ heteroalkyl, or $C_1$-$C_6$ alkoxy;
$R^{13}$ is hydrogen or $C_1$-$C_6$ alkyl,
wherein at least one of $X^1$, $X^2$, or $X^3$ has the structure of any one of Formula I-IV, and
wherein the oligonucleotide further comprises one or more adenosine deaminase acting on RNA (ADAR)-recruiting domains.

2. The oligonucleotide of claim 1, wherein at least 80% of the nucleotides of $[A_m]$ and/or $[B_n]$ include a nucleobase, a sugar, and an internucleoside linkage.

3. The oligonucleotide of claim 1, wherein $R^{12}$ is hydrogen, halogen, $C_1$-$C_6$ alkyl, or $C_1$-$C_6$ heteroalkyl.

4. The oligonucleotide of claim 1, wherein $R^{12}$ is fluoro.

5. The oligonucleotide of claim 1, wherein $R^{12}$ is hydrogen or $C_1$-$C_6$ alkyl.

6. The oligonucleotide of claim 1, wherein $R^{12}$ is hydrogen.

7. The oligonucleotide of claim 1, wherein at least one of $X^1$, $X^2$, and $X^3$ has the structure of Formula I, and N¹ is a nucleobase.

8. The oligonucleotide of claim 1, wherein at least one of $X^1$, $X^2$, and $X^3$ has the structure of Formula II, and N¹ is a nucleobase.

9. The oligonucleotide of claim 1, wherein at least one of $X^1$, $X^2$, and $X^3$ has the structure of Formula IV, and N¹ is a nucleobase.

10. The oligonucleotide of claim 1, wherein at least one of $X^1$, $X^2$, and $X^3$ has the structure of Formula III, and N¹ is a nucleobase.

11. The oligonucleotide of claim 1, wherein at least 20% of the nucleotides of $[A_m]$ and $[B_n]$ combined are 2'-O-methyl-nucleotides.

12. The oligonucleotide of claim 1, wherein A and B combined consist of 18 to 80 nucleotides.

13. The oligonucleotide of claim 1, wherein m and n are each, independently, an integer from 5 to 40; at least one of $X^1$, $X^2$, and $X^3$ has the structure of Formula I, Formula II, Formula III, or Formula IV, wherein N¹ is a nucleobase and each of $X^1$, $X^2$, and $X^3$ that does not have the structure of Formula I, Formula II, Formula III, or Formula IV is a ribonucleotide; $[A_m]$ and $[B_n]$ each include at least five terminal 2'-O-methyl-nucleotides and at least four terminal phosphorothioate linkages; and at least 20% of the nucleotides of $[A_m]$ and $[B_n]$ combined are 2'-O-methyl-nucleotides.

14. A conjugate comprising an oligonucleotide of claim 1 conjugated to a targeting moiety.

15. A complex comprising:
an oligonucleotide of claim 1; and
an mRNA,
wherein the oligonucleotide or conjugate and mRNA are hybridized to each other and the complex comprises a first mismatch at an adenosine of the mRNA.

16. A method of producing a complex, the method comprising contacting a cell with an oligonucleotide of claim 1.

17. A method for deamination of an adenosine in an mRNA, the method comprising contacting a cell with an oligonucleotide of claim 1.

* * * * *